United States Patent [19]

Tomlinson

[11] Patent Number: 5,121,443
[45] Date of Patent: Jun. 9, 1992

[54] NEURAL NET SYSTEM FOR ANALYZING CHROMATOGRAPHIC PEAKS

[75] Inventor: Barrett L. Tomlinson, Santa Clara, Calif.

[73] Assignee: Spectra-Physics, Inc., San Jose, Calif.

[21] Appl. No.: 410,552

[22] Filed: Sep. 21, 1989

Related U.S. Application Data

[62] Division of Ser. No. 343,111, Apr. 25, 1989, abandoned.

[51] Int. Cl.$^5$ .............................................. G06K 9/46
[52] U.S. Cl. ................................. 382/29; 73/23.23; 73/23.36; 210/656; 364/498; 382/14; 395/22
[58] Field of Search .................. 382/29, 17, 15, 14; 364/497, 498, 496, 513; 210/656; 73/23.22, 23.23, 23.35, 23.36

[56] References Cited

U.S. PATENT DOCUMENTS

| | | | |
|---|---|---|---|
| 4,468,742 | 8/1984 | Jenden et al. | 364/497 |
| 4,546,643 | 10/1985 | Bonneyrat et al. | 364/498 |
| 4,797,938 | 1/1989 | Will | 382/29 |
| 4,807,148 | 2/1989 | Lacey | 364/497 |
| 4,815,107 | 3/1989 | Kishimoto et al. | 382/29 |
| 4,837,726 | 6/1989 | Hunkapiller | 364/497 |
| 4,914,708 | 4/1990 | Carpenter et al. | 382/14 |

OTHER PUBLICATIONS

Spectra-Physics, "SP4270 Computing Integrator Operator's Manual, Section Seven-Principles of Integration", 1982, Spectra-Physics Part No. A 0099-110.
Joe P. Foley, "Systematic Errors in the Measurement of Peak Areas and Peak Height for Overlapping Peaks", J. of Chromatography, 384, 301-313 (1987).
D. E. Rumelhart & J. L. McClelland, "Learning Internal Representations By Error Propagation," parallel distributive processing: Explorations of the Micro Structures of Cognition, vol. 1, MIT Press, pp. 318-362 (1986).
"Chromatography Instruments and Systems," available from Spectra-Physics, Auto Lab Division, 3333 N. First Street, San Jose, Calif. 95134.
M. Abramowitz & I. A. Stegun (Editors), Handbook of Mathematical Functions, Applied Mathematical Series No. 55, National Bureau of Standards, Washington, D.C., p. 932 (Jun. 1964).
D. Rumelhart, G. Hinton, & R. Williams, "Learning Representation by back-propogating erors," Nature, 323, pp. 533-536 (1986).
J. Foley & J. Dorsey, "Equations for Calculation of Chromatographic Figures of Merit for Ideal and Skewed Peaks," Anal. Chem., 55, 730-737 (Apr. 1983).

*Primary Examiner*—Joseph Mancuso
*Attorney, Agent, or Firm*—Killworth, Gottman, Hagan & Schaeff

[57] ABSTRACT

A two-step process for characterization of peaks in a chromatogram is disclosed. Firstly, data corresponding to each peak or pair of peaks in the chromatogram is identified. A unique filter apparatus locates extrema of the curvature of the chromatographic data and a data file is generated containing characteristics of the extrema. A pattern recognition apparatus analyzes the characteristics of the located extrema and classifies the peak or peak combination represented by the data in the file as one peak or peak combination in a set of resolved peaks and selected combinations of resolved peaks. A portion of the chromatographic data, corresponding to the peak or peak combination identified by the pattern recognition apparatus, is identified. This portion includes the signal for said peak and the signal for the baseline upon which the peak is superimposed. In the second step, data for a peak or a peak combination identified as described above is processed and a set of characterizing parameters for the peak or the first peak in the peak combination is generated without a prior baseline correction to the data. The peak data including the baseline level upon which the peak is superimposed is analyzed using one of lookup-tables, neural nets, curve fitting, or combinations thereof. These characterization processes, using information about the peak crest and the peak inflection points, determines a set of characterizing parameters and a baseline estimate that best fit the identified data. The peak characterization is not biased by a prior baseline correction.

15 Claims, 17 Drawing Sheets

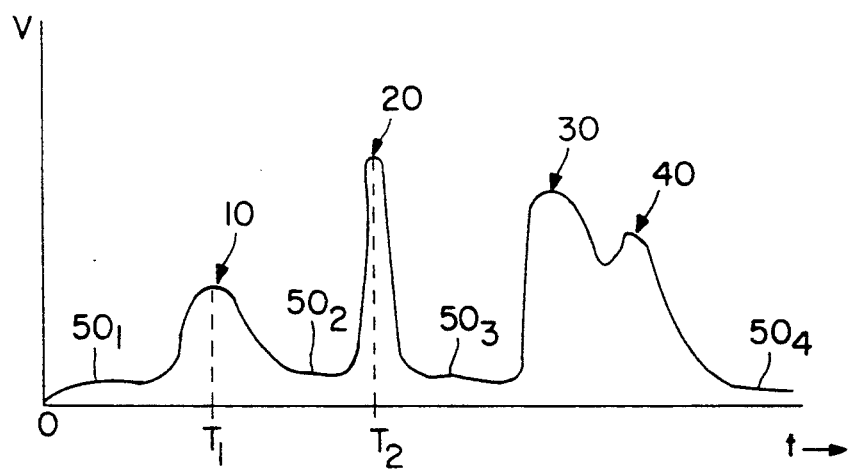
FIG. IA
PRIOR ART
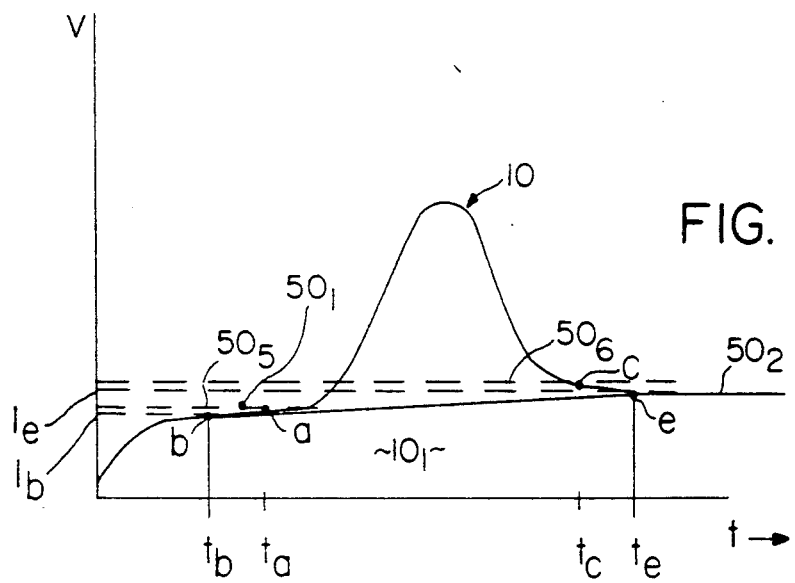
FIG. IB
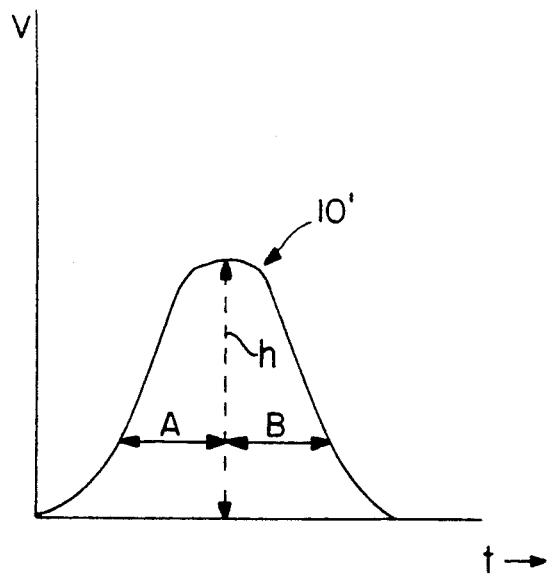
FIG. 2
PRIOR ART

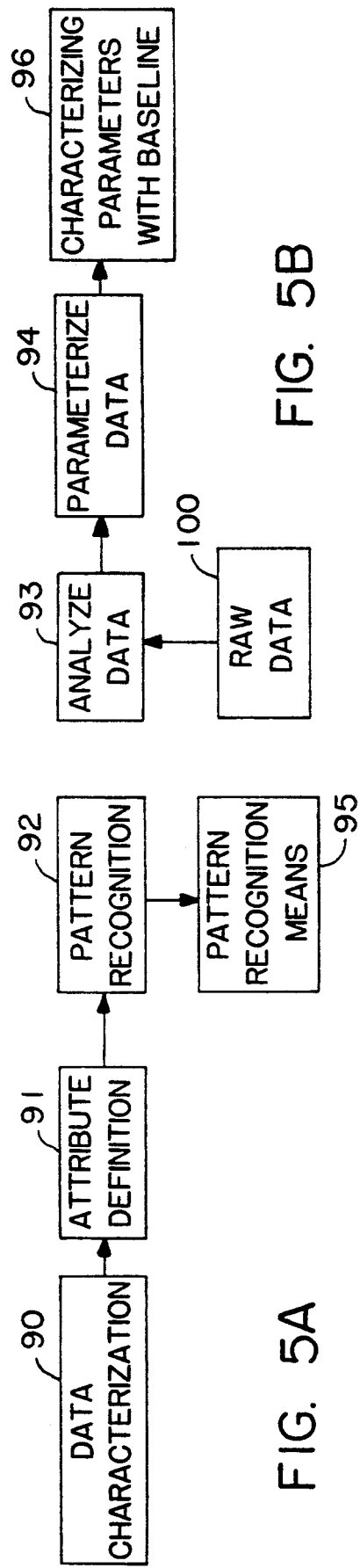

NEURAL NET SYSTEM FOR ANALYZING CHROMATOGRAPHIC PEAKS

This application is a division of application Ser. No. 07/343,111, filed Apr. 25, 1989 now abandon.

CROSS REFERENCE TO MICROFICHE APPENDICES

Appendix A, which is a part of the present disclosure, is a microfiche appendix consisting of 3 sheets of microfiche having a total of 161 frames. Microfiche Appendix A is a listing of computer programs and related data in one embodiment of this invention, which is described more completely below.

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD OF THE INVENTION

This invention relates generally to a method and apparatus for quantitatively defining gas and liquid chromatography data and more specifically to a method and apparatus for quantifying the signals from a detector used in gas and liquid chromatography so as to determine retention times, areas, widths, heights and skewness of measured chromatographic peaks.

BACKGROUND OF THE INVENTION

Gas and liquid chromatography are widely used analytic techniques for separation and quantitation of mixtures of chemical compounds. In chromatographic analyses, a small sample of a mixture is introduced initially at the top of a column coated or packed with an adsorbent. "Top" as used herein is a relative term and means the end or region of a chromatographic column where the sample is initially introduced to the column. The adsorbent reversibly adsorbs components of the mixture. Thus, initially the sample is bound to the adsorbent at the top of the column. A carrier gas or liquid, referred to as an eluent, is passed through the column. As the eluent passes through the column, the components of the sample are displaced from the adsorbent by the eluent and then the components are adsorbed at another point on the column.

The various components of the mixture migrate through the column at different rates. The rate of migration of each component depends upon the affinity of the adsorbent for the component and the ability of the eluent to displace the component from the adsorbent as well as other factors known to those skilled in the art. Accordingly, different components of the sample migrate down the column at different speeds. Thus, as the carrier gas or liquid emerges from the column, the components in the mixture are swept out of the column with the carrier gas or liquid at various time intervals, i.e. retention times, after the introduction of the sample at the top of the column.

To measure the retention times of the various components in the sample, a detector is placed at about the exit of the column so that the eluate emerging from the column passes through the detector. Typically in liquid chromatography, the detector employs either ultraviolet adsorbance, refractive index or florescence as the measurement means. In gas chromatography, flame ionization or thermal conductivity are frequently employed as the detection principle.

Independent of the detector used for the chromatographic measurement, the detector generates an electrical signal which changes as a function of time in response to the concentration of the components of the sample passing through the detector. FIG. 1A illustrates the features of a typical chromatogram. The vertical line at the left hand side of FIG. 1A represents the introduction of the sample at the top of the chromatographic column and the initiation of eluent flow through the column. A first resolved peak 10 reaches a maximum at a time T1 while a second resolved peak 20 reaches a maximum at a time T2. Time T1 is the retention time for peak 10 while time T2 is the retention time for peak 20. Peaks 30, 40 are fused peaks.

A baseline signal level, which is usually defined as the signal level associated with only eluent flow through a chromatographic column, is represented by the signal level $50_1$ prior to peak 10, the signal level $50_2$ between peak 10 and peak 20, and so forth. The signal level for peak 10 consists of a signal level associated with a component of the sample passing through the detector and a baseline signal level associated with eluent flow through the detector. As described more completely below, a central problem in interpretation of a chromatogram is determining the contribution of the base line signal level to the measured signal level for a peak. As shown in FIG. 1A, the baseline signal level is relatively constant, but in many chromatograms, the baseline signal level is not constant and in fact changes with time. The phase "baseline" is often used to refer to the baseline signal level of a chromatogram.

Analysis of peaks 10, 20, 30, 40 (FIG. 1A) provides information about the identity and quantity of specific components of the sample, as well as performance indicators on the operation of the chromatographic column. Information typically generated for each peak, as described more completely below, includes peak characteristics such as retention time, peak area, peak height, peak width and skewness.

To ascertain the characteristics of resolved chromatographic peaks 10, 20 as illustrated in FIG. 1A, the detector signal is analyzed by measuring attributes of the signal such as the level, slope, or curvature of the detector signal as a function of time. The level of the detector signal means the actual signal from the detector. The slope of the detector signal means the first derivative with respect to time of the detector signal (first derivative) and the curvature means the second derivatives with respect to time of the detector signal (second derivative).

To characterize a resolved peak 10, 20 (FIG. 1A), when one or more of these parameters (the level, slope or curvature of the detection signal) exceeds a threshold level, a first baseline reference point, as described below, is usually established at a predetermined time prior to the time when the threshold level was exceeded. The threshold level is typically determined by examination of a chromatogram. (The threshold level is generally selected as the level corresponding to the baseline signal level, e.g., signal level $50_1$ (FIG. 1A).) After establishment of the first baseline reference point, the detector signal is continuously integrated until the parameter being monitored falls below the threshold level for a selected period of time. When the parameter falls below the threshold level for the selected period of time, a second baseline reference point is established. A straight line is generally interpolated between the first baseline reference point and the second baseline reference point.

FIG. 1B illustrates a common application of this method. In FIG. 1B, a single resolved peak 10 is shown with baseline signal levels $50_1$, $50_2$. A first threshold level is represented by dashed line $50_5$. At point a, which occurs at time $t_a$, the detector signal level exceeds threshold level $50_5$. A first baseline reference point b is generally established at time $t_b$, which is a predetermined time prior to time $t_a$. The detector signal level is continuously integrated until time $t_e$. Time $t_e$ is a selected period after the detector signal level falls below a second threshold level $50_6$ at point c. A second baseline reference point e is defined at time $t_e$. In this example, the chromatogram of FIG. 1A was analyzed to establish the two different threshold levels used in the baseline correction.

Thus, the integrated signal, i.e., the total area under curve 10 between points $t_b$ and $t_e$, includes the area corresponding to the baseline signal. To obtain only the peak area, the area corresponding to the baseline signal must be subtracted from the total area. The problem is to accurately estimate the area corresponding to the baseline signal. In one case, the peak area is found by subtracting the area of the trapezoid [the shaded area $10_1$ in FIG. 1B] defined by $(t_b, 0)$, $(t_b, l_b)$, $(t_e, l_e)$, $(t_e, 0)$ where $l_b$ and $t_e$ are the detection signals at time $t_b$ and $t_e$ respectively. Here the terms within parenthesis are x, y coordinates with the x coordinate being time and the y coordinate being detector output signal. Peak 10 after subtraction of area $10_1$ is illustrated in FIG. 2 as peak 10'. The peak characteristics, i.e., peak height, width, skewness and the time of maximal/minimal signal, i.e., the retention time, are determined using the baseline corrected data of FIG. 2 as described below.

Thus, peak integration is generally done by (i) detecting a point of departure from baseline, i.e., detecting the time at which one or more of the detector signal level, the slope or curvature exceed a threshold level; (ii) establishing a first baseline reference point at some predefined time prior to the point of departure from baseline; and (iii) continuously integrating the chromatographic signal from the first baseline reference point until the signal again drops below the threshold level from a predetermined time, i.e., the second baseline reference point.

Conventional chromatographic peak quantitation apparatus require that parameters be set which control analysis of the detector signal, e.g., the baseline-threshold level, and sometimes small changes in the control settings or detector input signals can cause very large changes in the peak quantitation determination. Thus, present methods for analysis of chromatographic data are unstable.

An alternative to the above method for correcting the measured data for the baseline signal level is to obtain a blank chromatogram (a chromatographic run with no sample injection). The blank chromatogram is subtracted from the chromatogram of interest before peak integration so as to obtain a baseline corrected chromatogram. In either approach, the trapezoid subtraction or the blank chromatogram subtraction, the determination of peak parameters is dependent upon the accuracy of the baseline correction.

As previously described, peak 10' of FIG. 2 is a baseline corrected representation of peak 10 of FIGS. 1A and 1B. A first and a second baseline reference points b, e were determined and baseline corrected peak 10' was defined as the peak above the straight line between first and second baseline reference points b, e. The parameters characterizing peak 10 are determined using baseline corrected peak 10'.

The peak width is determined by measuring leading peak half width A (FIG. 2) and trailing peak half width B and adding the two half widths. A measure of peak skewness is a ratio of the two half widths. The vertical height h of the peak is represented by the vertical line from the peak maximum to the baseline, i.e., the x axis in FIG. 2, of peak 10. In one measurement of asymmetry, i.e., peak skewness, the asymmetry is determined by drawing a line horizontal to the x-axis at 10% of vertical height h. The distance A from vertical line h to the left edge of the peak is the leading peak half width and distance B from vertical line h to the right edge of the peak is the trailing peak half width. Other measures of asymmetry measure the peak half widths at different fractions of vertical height h.

If a peak is gaussian in shape, distance A, the leading peak half width, equals distance B, the trailing peak half width. If a peak is gaussian, the column efficiency in terms of the number of theoretical plates N is easily determined. The general definition of column efficiency in units of theoretical plates is:

$$N = \frac{T_r^2}{\sigma^2} \qquad (1)$$

where $T_r$ is the retention time for the peak and $\sigma^2$ is the variance or the second central moment of the peak measured in time units. For a gaussian curve, $$\sigma^2 = \frac{A^2}{2\pi h^2} \qquad (2)$$

where A is the area of the gaussian peak and h is the peak height. Substituting Equation 2 into Equation 1 gives $$N = \frac{2\pi (hT_r)^2}{A^2} . \qquad (3)$$

Therefore, column efficiency as measured by theoretical plates can be determined from the vertical peak height h, the retention time and the area of a gaussian curve.

Non-Gaussian peaks (nonsymmetric peaks) in which distance A (FIG. 2) is not equal to distance B are typically encountered in chromatographic measurements, as discussed more completely below. However, the use of an equation such as equation (3), which is based upon a symmetric peak, to determine theoretical plate numbers for nonsymmetric peaks can result in serious errors.

Several researchers have used an exponentially modified gaussian (EMG) model for quantitation of chromatographic peaks. The development, characterization and theoretical and experimental justification of the exponentially modified gaussian (EMG) model has been discussed in several different references. See for example, R, E. Pauls and L. B. Rogers, *Anal. Chem.* 49, 628, 1977, or E. Grushka et al., *Anal. Chem.* 41, 889–892, 1969.

The exponentially modified gaussian function G(t) is a convolution of a gaussian function and an exponential decay function and is expressed as:

$$G(t) = \frac{A}{\tau} e^{[\frac{1}{2}(\frac{\sigma}{\tau})^2 - (\frac{t-t_g}{\tau})]} \int_{-\infty}^{z} \frac{e^{-\frac{y^2}{2}}}{\sqrt{2\pi}} dy \quad (4)$$

where $$z = \frac{t - t_g}{\sigma} - \frac{\sigma}{\tau}$$

In Equation 4, A is an amplitude which corresponds to the peak height, $t_g$ is the time of maximum amplitude of the Gaussian function, $\sigma$ is a standard deviation of the gaussian function and $\tau$ is a time constant of the exponential decay function. The ratio $\tau/\sigma$ is a measure of peak asymmetry. As $\tau/\sigma$ increases, the chromatographic peak becomes more tailed. Conversely, as $\tau/\sigma$ approaches zero, the chromatographic peak approaches a gaussian peak. Thus, an EMG function can be used to describe both gaussian peaks and non-gaussian peaks. FIG. 3A illustrates an EMG peak. FIG. 3B illustrates the slope, first derivative with respect to time, of the MG peak and FIG. 3C illustrates the curvature, the second derivative with respect to time, of the EMG peak. The EMG peak in FIG. 3A is a positive resolved peak because the peak has a positive maximum. However, negative resolved peaks, i.e., peaks having a negative minimum, are also encountered in chromatograms.

Chromatographic peaks are often fused as shown in FIG. 1A. The analysis of fused peaks is much less straightforward and the results are dependent upon the means defined to separate the peaks as well as the baseline correction. In one method, (see, for example, Spectra Physics, "SP4270 Computing Integrator Operator's Manual, Section Seven—Principles of Integration," 1982, Spectra Physics Part No. A 0099-110), the areas are allocated by dropping a perpendicular line from the valley separating peaks to the interpolated baseline. In an alternative approach, the peaks are "skimmed" by taking baseline references at one or more valleys. The vertical drop method and skimming method are very inaccurate in their allocation of area between fused peaks. Errors in excess of 30% typically occur in area allocations for fused peaks using either of these methods. In these methods, the slope and/or the curvature of the detector signal have been used to identify the peak maximums and the valley between the maximum of two fused peaks.

Foley in "Systematic Errors in the Measurement of Peak Areas and Peak Height for Overlapping Peaks," *J. of Chromatography*, 384, 301-313 (1987) suggested methods of estimating EMG line shape parameters for fused peaks using retention time, front and rear half-widths, and amplitudes of baseline corrected peaks. The parameters used by these investigators, as illustrated in FIG. 4, are apparent peak heights $h_{p,1}$ and $h_{p,2}$, valley height, $h_v$, and peak widths a,b. These parameters are defined after the peaks have been baseline corrected. Therefore, as described below, while the method of Foley is better than the vertical drop and skimming methods described above, the method is limited by the accuracy of the baseline determination.

Foley suggests that a logical approach for quantitation of fused peaks is to develop a quantitative method based upon measurements in regions of minimum distortion. He further suggests that for two fused peaks there is much less distortion for the first peak than the second, as evidenced by the generally insignificant errors in peak height for the first peak. Foley derived the following empirical equation for the area of a peak:

$$A = 1.64 \, h_p W_{0.75}(b/a)^{0.717} \quad (5)$$

where A is the peak area, $h_p$ is the peak height and $W_{0.75}$ and (b/a) are the peak width and asymmetry measured at 75% of the peak height respectively.

Foley defines the relative valley as the ratio, expressed as a percentage, of the valley height $h_v$ to the apparent height $h_p$ of the peak in question. The investigator reported that the bias of Equation (5) is less than $\pm 1.1\%$ for well-resolved tailed (EMG) peaks having $\tau/\sigma$ in the range of 0.-4.2 and for well resolved symmetric (gaussian) peaks. For overlapping EMG peaks, or for an EMG peak overlapped by a gaussian peak with area ratios between 1:4 and 4:1, empirical equation (5) is reported to be accurate to $\pm 4\%$ for the first peak provided that the relative valley between peaks is less than 45%. For a symmetric peak overlapped by an EMG peak, empirical equation (5) is accurate to within $\pm 2\%$ for the second peak if the relative valley is less than 50%. For overlapping peaks with ratios outside the 1:4 and 4:1 range, equation (5) is described as being somewhat more accurate but only for the larger peak of the overlapped pair. Hence, not only is this method limited by the accuracy of the baseline correction, but also the method is limited to EMG peaks having specified relationships.

Equation (5) is used to quantitate only one peak of an overlapped pair. But if an integrator is used to measure the total area of the two overlapping peaks, the area of the remaining peak is determined by subtraction of the calculated area from the total measured area.

All of the prior art methods described above, including the work of Foley and Dorsey are dependent upon an accurate determination of the baseline. Inaccuracies in the baseline determination can cause significant errors in the derived properties for a peak. Since in practical chromatography a wandering baseline and large overlapping peaks atop a wandering and indeterminate baseline are frequently encountered, quantitation of either resolved or fused peaks using the prior art methods, described above, is often problematic. Baseline drift during a fused peak sequence causes sizeable errors and uncertainty in the determination of the prior position of the interpolated baseline. Moreover, a negative peak (a frequent occurrence in conductivity or refractive index detection) causes serious error in baseline determination particularly when coupled with a drifting baseline.

Hence, the methods described above are not suitable for analysis of chromatographic data without baseline resolution. In general terms, identification of individual chromatographic peaks in a chromatogram is a pattern recognition problem because the chromatogram typically consists of one or more peaks of a known shape superimposed on a baseline. Thus, a first problem is identifying each of the peaks from the pattern of resolved and fused peaks in the chromatogram. A second problem is determining a set of characterizing parameters for each identified peak. In other areas of science, methods have been developed for pattern recognition. For example, a neural net, sometimes called a neural network, has been taught to complete numerical sequences based upon training the net with other numerical sequences.

A neural net includes input units, internal units and output units. The input units are a first layer of the neural net. The internal units may be configured in one of more layers and the output units are the final layer in the net. Each of the input units supplies a signal to each of the internal units in the layer of the net adjacent to the inputs units. If the neural net has more than one layer of internal units, each unit in the first layer of internal units, i.e., the internal units receiving signals from the input units, generates an output signal that is provided to each internal unit in the second layer of internal units. Other layers of internal units are connected to adjacent layers of internal units in a similar manner. Each internal unit in the layer of internal units adjacent to the layer of output units provides a signal to each output unit. Each output unit provides an output signal.

For each neural net, the problem is to develop the internal units of the net so that for a given input pattern the net generates the appropriate output pattern. This requires that the net be trained to recognize the input patterns and generate the corresponding output patterns. For a specific example of configuring a neural net as an exclusive OR gate see D. E. Rumelhart, "Learning Internal Representations By Error Propagation," parallel distributive processing: "Explorations of the Micro Structures of Cognition, Volume 1," D. E. Rumelhart and J. L. McClelland (eds), Cambridge, M. A., MIT Press, pp. 3181 $\propto$ 362.

While pattern recognition methods, such as neural nets, are known, to the best of my knowledge such methods have not been used for either identification of chromatographic peaks in a chromatogram or characterization of identified chromatographic peaks. Accordingly, the prior art methods, as described above, for identification and characterization are limited by the requirement for a prior baseline determination which can bias the data. Moreover, the prior determination of a baseline for a fused peak sequence or a negative peak when the baseline is drifting is problematic. In addition to a prior baseline determination, the previously described prior art methods for analysis of fused peaks sequences require specific relationships between the peaks and an empirical relationship for evaluation of the peak area. Thus, a method and apparatus for analyzing a chromatogram without a prior baseline determination is needed to overcome the prior art limitations.

SUMMARY OF THE INVENTION

Unlike prior art methods for characterization of chromatograms which required prior determination of a baseline, the method and apparatus of this invention determine the retention time, peak width, peak area, and peak skewness for chromatographic data having resolved peaks, slightly fused peaks of the same sign, slightly fused peaks of opposite sign, strongly fused peaks of the same sign, and strongly fused peaks of opposite sign without a prior determination of a baseline. The retention time, peak width, peak area and peak skewness for each chromatographic peak, a set of characterizing parameters for a peak, and the baseline signal level for the peak are determined together.

The set of characterizing parameters for a chromatographic peak and a baseline for that peak are determined simultaneously, i.e., in the same process step. Accordingly, the baseline correction prior to characterization of the data, as in the prior art methods described above has been eliminated. Further, the above prior art methods used signals having about the same magnitude as the baseline signal to define the baseline. The signal-to-noise ratio in the baseline determination was small and the correction of the data for the baseline contribution was often difficult. In the system and method of this invention, information about the peak crest is used to estimate the peak shape and in turn the characterizing set of parameters for the peak and the baseline. Since the signal-to-noise ratio is typically the largest about the peak crest, the prior art problems associated with the small signal-to-noise ratio in baseline corrections are not encountered.

According to the principles of this invention, extreme of the curvature of the chromatographic signal are used to identify each peak in a chromatographic. The curvature further reduces the noise problems associated with a wandering baseline because if the baseline signal is constant or the baseline signal changes at about a constant rate, i.e., has about a constant slope, the curvature signal does not contain a contribution from the baseline so that the start and end of a peak are easily determined from the curvature signal. Further, curvature extrema for both positive and negative peaks are determined in the same manner so that, in contrast to prior art methods described above, characterization of negative peaks with a wandering baseline is fully equivalent to characterization of positive peaks.

According to the principles of this invention, characterization of peaks in a chromatogram is a two-step process. In a first step, data corresponding to each peak or each pair of peaks in the chromatogram is identified. A unique filter apparatus locates extrema of the curvature of the chromatographic data nd characteristics of the extrema are stored for further processing. A pattern recognition apparatus analyzes the stored characteristics of the extrema and classifies the the stored data as representing one peak or one peak combination in a seat of resolved peaks and selected combinations of resolved peaks. A portion of the chromatographic data, which corresponds to the peak or peak combination identified by the pattern recognition apparatus, is then selected for further analysis. This portion of the raw data includes both the signal for the peak and the signal for the baseline upon which the peak is superimposed.

In the second step, data for a peak or a peak combination identified as described above, or in the alternative, identified by some other process, is processed and a set of characterizing parameters for the peak or the first peak in the peak combination is generated without a prior baseline correction to the data. The peak data including the baseline level upon which the peak is superimposed is analyzed using one of lookup tables, neural nets, curve fitting, and combination of lookup tables, neural nets and curve fitting. Each of these characterization processes, using information about the peak crest and the peak inflection points, determines a set of characterizing parameters and a baseline estimate that best fit the identified data. Thus, the peak characterization according to the principles of this invention is not biased by a prior baseline correction.

In one embodiment, the process of this invention is used in an automated data system which includes a detector for providing a time varying output signal. The output signal includes a plurality of peaks superimposed on a baseline. The detector output signal is converted to a time series of digitized data by an analog-to-digital converter and the digitized data is stored for further processing.

The digitized data is retrieved from the storage means and a second time derivative of the digitized data is generated. As the second time derivative of the digitized data is generated, the extrema of the second time derivative are located. The characteristics of each extremum are stored for further processing.

After each extremum is stored, the number of stored extrema is tested to determine whether sufficient extrema are available for identification of a peak by a pattern recognition means. When either at least four extrema are stored, one of which is a baseline, or at least eight extrema and no baseline are stored, the pattern recognition means processes the stored extrema and identifies the extrema as representing either (i) one peak in a set of resolved peaks or (ii) one peak combination in a set fused peak combinations. In one embodiment, the pattern recognition means uses a set of empirical rules to classify the stored extrema as representing a peak or peak combination in the five groups of peaks including (i) resolved peaks, (ii) slightly fused peaks of the same sign, (iii) slightly fused peaks of opposite sign, (iv) strongly fused peaks of the same sign, and (v) strongly fused peaks of opposite sign.

The process used to identify each of the peaks in a measured chromatogram, represents a significant advancement in the analysis of chromatograms. In the prior art methods of Foley and Dorsey, assumptions were made about the fused peak sequences and empirical relationships used to identify the characteristics of the fused peaks. According to the principles of this invention, each peak in the measured data is identified so that only data for that peak can be selected from the raw data file and subsequently analyzed. The identification process provides the user with a powerful tool for analysis of chromatograms, because the identification process is not affected by a wandering or changing baseline.

After identification of the measured peak or measured peak combination, the identification in conjunction with the extrema for the peak or peak combinations are input to a data selection means which in turn selects a range of raw data, i.e., a portion of the measured data which includes the measured peak or peak combination. The automated system then calculates a characterizing set of parameters for the measured peak using only the selected portion of the raw data. Unlike the prior art methods described above, the raw data is not baseline corrected prior to processing by the peak characterizing means. Rather, the peak characterizing means of this invention calculates a set of characterizing parameters and a baseline estimate for the peak using raw data that includes the signal level associated with the peak and the baseline signal level.

Several alternative embodiments are described for calculating the characterizing set of parameters and the baseline estimate for a peak in a chromatogram. In one embodiment, a skewness parameter, called a signature ratio, is calculated for each measured peak and the signature ratio is used in combination with a lookup table, which contains sets of peak definition parameters for a range of signature ratios, to determine a characterizing set of parameters. In another embodiment, a neural network has been trained to generate a set of characterizing parameters based upon the second time derivative of the selected raw data which is provided as input signals to the neural network. In these embodiments, a peak shape is generated using the set of characterizing parameters and the peak shape is subtracted from the raw data to form the baseline estimate. Hence, in contrast to the prior art methods, which estimated a baseline, corrected the raw data for the baseline, and then determined the characterizing parameters, in these embodiments the baseline estimate is done only after the characterizing parameters are ascertained.

In yet another embodiment, a curve fitting procedure is used to determine the best fit of a set of peak characterizing parameters to the selected raw data. In the curve-fitting process, the best set of characterizing parameters for the selected raw data is iteratively determined in combination with a least squares estimate of the baseline.

Combinations of the lookup table, neural network and curve fitting are also used to generate a set of characterizing parameters for each peak. In another embodiment, a pair of neural networks are used to generate characterizing parameters for each resolved peak and a Simplex fit is used to generate a set of parameters for each peak in fused peak sequences.

Another feature of this invention includes a method for generating the pattern recognition means used in identification of the peak or peak combination described above. In this method, specified data types, for example peaks, in measured data are identified and each specified data type is characterized. For example, in chromatograms the peaks may be of a gaussian, exponentially modified gaussian or general shape. Moreover, the peaks in a chromatogram are often fused. Thus, each peak in the fused peak sequence must be classified as one of the specified data types so that a characterizing set of parameters can be obtained for each peak.

I have discovered that each peak in any fused peak sequence can be classified by sequentially processing the fused peak sequence as pairs of peaks and classifying each fused pair of peaks. The classification of pairs of fused peaks first requires determination of the possible combinations of pairs of a specified data type, for example EMG peaks. From all possible combinations of pairs of EMG peaks, in one embodiment, the minimum number N of combinations of pairs of EMG peaks required to reproduce the peak pair combinations in measured data are empirically determined. In this embodiment, the N combination of pairs of EMG peaks are (i) slightly fused peaks of the same sign, (ii) sightly fused peaks of opposite sign, (iii) highly fused peaks of the same sign, and (iv) highly fused peaks of opposite sign.

After determination of the specified data type and the minimum N combinations of pairs of the specified data type, the next step in the generation of pattern recognition means is to find an attribute which can be calculated for the specified data type and each of the N combinations of pairs of the specified data type. Preferably, the attribute is a waveform which has different characteristics for the specified data type and each of the N combinations of the specified data type. For example, when the specified data type was resolved EMG peaks, the attribute was the second derivative with respect to time and the different characteristics of the second derivative with respect to time were the extrema of the second time derivative.

After the attribute and the unique characteristics of the attribute for the specified data type and each of the minimum N combinations are ascertained, the final step in generation of a pattern recognition means is developing a means for uniquely identifying the characteristics of the attribute for each of the specified data types and each of the N combinations. This means comprises the pattern recognition means because the means for uniquely identifying the characteristics of the attribute can be used to classify measured characteristics of the attribute. For example, in one embodiment, an empirical set of rules was generated to classify extrema of the second time derivative of measured chromatographic data.

Another feature of this invention includes a method and apparatus for locating extrema, i.e., characteristics, of the second derivative, i.e., an attribute, of data bunches having a characteristic interval. Typically, the characteristic interval is a selected period of time, sometimes called a time width or time window. The method and apparatus includes at least two filters which are used in locating the characteristics of the second derivative. The first filter generates a curvature value for data bunches having the characteristic interval. A second data set is formed with each data bunch in the second set having a second characteristic interval that is an integer multiple of the first-mentioned characteristic interval. The second filter generates a curvature value for data bunches having the second characteristic interval. The first and second filters sequentially calculate a curvature for each data bunch in the first and second data set respectively.

To locate the extrema of the second derivative, the calculation of the curvature by the first and second filters is sequenced so that the filters are maintained in alignment with respect to the data bunches being processed. As each curvature is calculated, a measure of the curvature is compared with a stored measure of curvature, the stored measure being the best previously calculated estimate of an extremum of the curvature. The comparison identifies either the measure of the curvature of the stored measure of the curvature as (i) the measure best estimating an extremum or (ii) an extremum of the curvature.

BRIEF DESCRIPTION OF THE DRAWINGS

FIG. 1A illustrates a typical chromatographic trace.

FIG. 1B illustrates a prior art baseline connection for a resolved peak.

FIG. 2 illustrates a baseline corrected chromatographic peak and parameters used to characterize the corrected peak.

FIGS. 5A and 5B are a general block diagram illustrating the method for processing chromatographic data according to the principles of this invention.

DETAILED DESCRIPTION

Figure 3A:
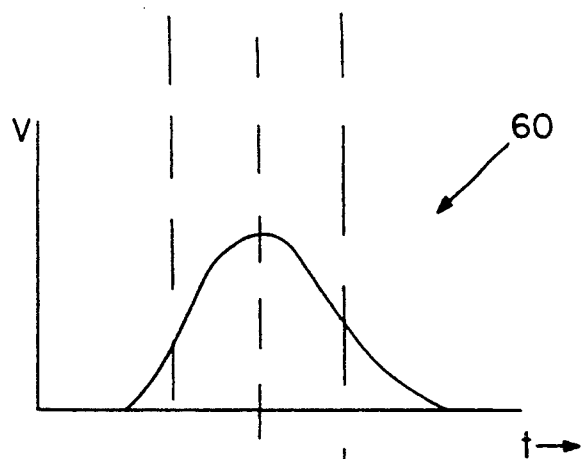
FIGS. 3A, 3B, and 3C illustrate an exponentially modified gaussian (EMG) chromatographic peak, the first derivative of the EMG peak, and the second derivative of the EMG peak, respectively.
Figure 3B:
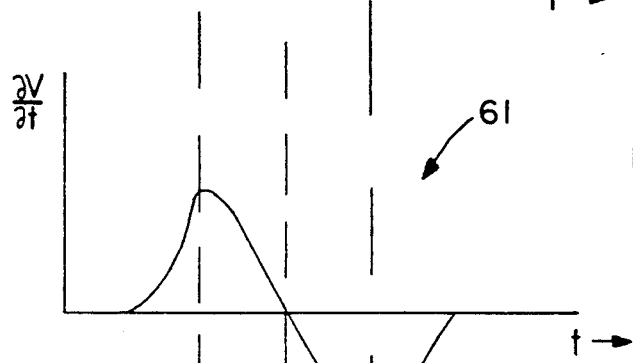

Unlike prior art methods for characterization of chromatograms which required prior determination of a baseline, the method and apparatus of this invention determine the retention time, peak width, peak area, and peak skewness for chromatographic data having resolved peaks, slightly fused peaks of the same sign, slightly fused peaks of opposite sign, strongly fused peaks of the same sign, and strongly fused peaks of opposite sign without a prior determination of a baseline. The retention time, peak width, peak area and peak skewness for each chromatographic peak, a set of characterizing parameters for a peak, and the baseline signal level for the peak are determined together.

The simultaneous determination of the set of characterizing parameters for a chromatographic peak and the baseline for that peak eliminates the baseline correction prior to characterization of the data as in the prior art methods described above. Further, the above prior art methods used signals having about the same magnitude as the baseline signal to define the baseline. Hence, the signal-to-noise ratio in the baseline determination was very small and accordingly the correction of the data for the baseline contribution was often difficult. As explained more completely below, the in system and method of this invention, information about the peak crest is used to estimate the peak shape and in turn the characterizing set of parameters for the peak and the baseline. Since the signal-to-noise ratio is typically the largest about the peak crest, the prior art problems associated with the small signal-to-noise ratio in baseline corrections are not encountered.

Moreover, according to the principles of this invention, extrema of the curvature of the chromatographic signal are used to identify each peak in a chromatogram.

The curvature further reduces the noise problems associated with a wandering baseline because if the baseline signal is constant or the baseline signal changes at about a constant rate, i.e. has about a constant slope, the curvature signal does not contain a contribution from the baseline so that the start and end of a peak are easily determined from the curvature signal. Further, curvature extrema for both positive and negative peaks are determined in the same manner so that, in contrast to prior art methods described above, characterization of negative peaks with a wandering baseline is fully equivalent to characterization of positive peaks.

As used herein, the "sign" of a peak, positive or negative, is determined by the peak amplitude. If the peak amplitude has a positive maximum, the peak is a positive peak. Conversely, if the peak amplitude has a negative minimum, the peak is a negative peak. In general terms for both positive and negative peaks, the phrases "Maximum/minimum amplitude" and "peak creat" are used hereinafter to characterize the maximum height, i.e., displacement, of the peak.

According to the principles of this invention, characterization of peaks in a chromatogram is a two-step process. In a first step, data corresponding to each peak or each pair of peaks in the chromatogram is identified. As explained more completely below, a unique filter apparatus locates extrema of the curvature of the chromatographic data and a file is generated containing characteristics of the extrema. A pattern recognition apparatus analyzes the characteristics of the located extrema and classifies the peak or peak combination represented by the data in the file as one peak or one peak combination in a set of resolved peaks and selected combinations of resolved peaks. A portion of the chromatographic data, which corresponds to the peak or peak combination identified by the pattern recognition apparatus, is then selected for further analysis. This portion of the data includes both the signal for the peak and signal for the baseline upon which the peak is superimposed.

In the second step, data for a peak or a peak combination identified as described above, or in the alternative, identified by some other process, is processed and a set of characterizing parameters for the peak or the first peak in the peak combination is generated without a prior baseline correction to the data. As explained more completely below, the peak data including the baseline level upon which the peak is superimposed is analyzed using one of lookup tables, neural nets, curve fitting, and combinations of lookup tables, neural nets and curve fitting. Each of these characterization processes, using information about the peak crest and the peak inflection points, determines a set of characterizing parameters and a baseline estimate that best fit the identified data. Thus, the peak characterization according to the principles of this invention is not biased by a prior baseline correction.

The determination of a set of characterizing a parameters and a baseline estimate that best fit the identified data is fundamentally different from the prior art methods described above. In those methods, a three step process was used to determine a set of characterizing parameters. The three steps were (i) estimate of baseline, (ii) correct the raw data using the estimated baseline and (iii) estimate a set of characterizing parameters for the baseline corrected data. Hence in this prior art process, a prior baseline determination was used and as previously described the prior baseline determination was often complicated by a wondering or an indeterminate baseline and a poor signal-to-noise ratio. In contrast, according to the principles of this invention, a baseline and a characterizing set of parameters are determined simultaneously, i.e., in the same processing step, so that a prior baseline determination is not necessary. Thus, any errors introduced by a prior baseline estimate are eliminated, and a set of parameters, which characterize the peak, and a baseline are estimated to achieve the best fit to the measured data.

The process of this invention is illustrated as a flow diagram in FIGS. 5A and 5B. As previously mentioned, the process of this invention is a two-step process and this is illustrated in FIG. 5B as analyze data 93, and parameterize data 94. Analyze data 93 includes a pattern recognition means for classification of peaks in a chromatogram. The process used to develop the pattern recognition means is illustrated in FIG. 5A.

Briefly, the process used to develop the pattern recognition means includes three steps. The first step, data characterization 90, defines the peaks and combinations of peaks that must be recognized. The second step, attribute definition 91, determines the attributes for each of the peaks and combinations of peaks identified by data characterization 90 that are subsequently used in development of pattern recognition means 95. Finally, the third step, pattern recognition 92, analyzes the attributes generated by attribute definition 91 and generates pattern recognition means 95. As described more completely below, pattern recognition means 95, when supplied with an attribute, classifies, i.e. identifies, the attribute as representing one of the peaks or one of the peak combinations generated by data characterization 90.

The principles of this invention are described using chromatographic data which includes, for example, gaussian and exponentially-modified gaussian (EMG) peaks. However, the method is applicable to any data having peaks with a characteristic shape. Thus, principles of this invention may be used, for example, to analyze peaks associated with neutron activation analysis or capillary zone electrophoresis.

Further, as described more completely below, a selected attribute, the second derivative of the chromatographic data, and characteristics of the selected attribute, extrema of the second derivative, are used in this embodiment. In view of this disclosure, other selected attributes and characteristics of the selected attributes can be used with the principles of this invention to characterize data having the selected attribute. Accordingly, the use of the second derivative and the extrema of the second derivative are illustrative only of the principles of this invention and are not intended to limit the scope of the invention.

The first step in data characterization 90 is to analyze measured chromatographic data to ascertain the types of peaks generally observed. For example, as described above in measured chromatographic data, the types of the peaks include gaussian, EMG and general shapes. Further, each type of peak may be either a positive peak or a negative peak. For each type of peak, a set of characterizing parameters, as previously described, is defined. Usually, this step can be accomplished by examining the prior art literature for the measurements of interest. Alternatively, measured data having resolved peaks cold be digitized and the resolved peaks statistically analyzed to define the types of peaks in the data and the parameters necessary to characterize the peaks.

Figure 19A:
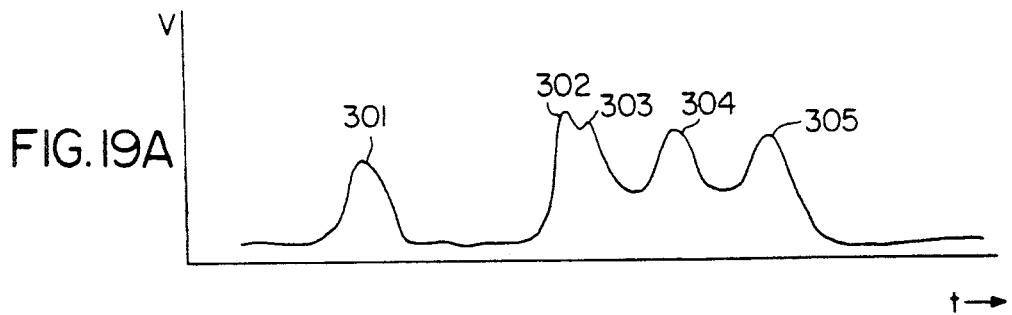
FIG. 19 illustrates one example of a portion of a chromatogram which is analyzed according to the principles of this invention.
Figure 19B:
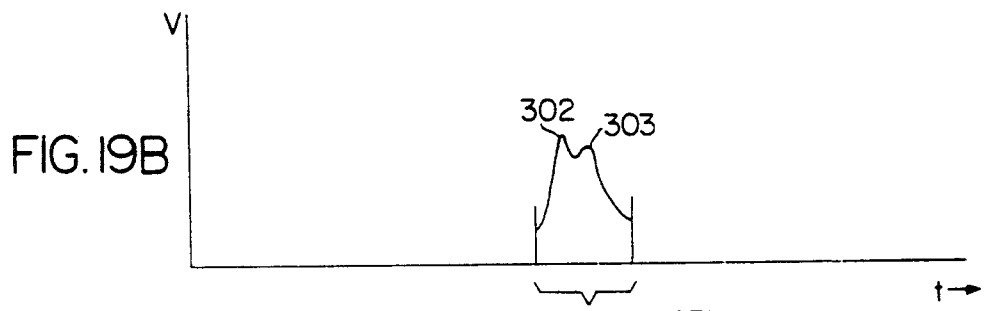

The second step in data characterization 90 uses the different peaks identified in the first step to define a minimum set of peaks including resolved peaks and combinations of resolved peaks so that each peak in a chromatogram can be classified by pattern recognition means 95. The important aspect of this step is to specify a first resolved peak and then identify the possible combinations of resolved peaks with this peak. I discovered that if chromatographic data is processed sequentially forward in time, each fused peak sequence in a chromatogram can be represented as sequential pairs of fused peaks. For example, as illustrated in FIGS. 19A to 19E, a fused peak sequence containing four peaks 302–305 can be analyzed by sequentially identifying (i) peaks 302, 303 (FIG. 19B), (ii) peaks 303, 304 (FIG. 19C) and (iii) peaks 304, 305 (FIG. 19D). The actual analysis is described below.

The possible combinations of pairs of resolved peaks include (i) a positive resolved peak with either another positive resolved peak or a negative resolved peak, or (ii) a negative resolved peak with either another negative resolved peak or a positive resolved peak pair. Each combination of resolved peaks creates a fused peak pair. In addition to the combinations of peaks, the degree of overlap, usually referred to as fusion, of the combinations of peaks must be defined. In a chromatogram, the peaks may be either slightly fused (FIG. 19D) or strongly fused (FIG. 19B). The degree of fusion between peaks, i.e. slightly or strongly fused, that must be considered is determined by the attributes used in pattern recognition, as discussed below.

Thus, for chromatograms, the minimum set includes (i) resolved peaks, (ii) slightly fused peaks of the same sign, (iii) slightly fused peaks of opposite sign, (iv) strongly fused peaks of the same sign, and (v) strongly fused peaks of opposite sign.

Hence, data characterization 90 first determines from measured data the characteristics of the data of interest, i.e., the types of peaks. Then a minimum set of resolved peaks and combinations of resolved peaks required to sequentially identify fused peak sequences in a chromatogram are determined.

After the measured data are characterized by data characterization 90, attribute definition 91 (FIG. 5A) determines a selected attribute of each peak and each fused peak combination in the minimum set. In one embodiment, the selected attribute is the second derivative with respect to time and so that second derivative for each resolved peak and each fused peak pair in the minimum set from data characterization 90 is calculated. Use of the second time derivative as the selected attribute places a limitation on the data that can be processed according to the principles of this invention. The characteristics (peaks) of the data that are analyzed must have a continuous second time derivative. Other pattern recognition means could be developed using other attributes of the measured data by one skilled in the art in view of this disclosure.

Figure 3C:
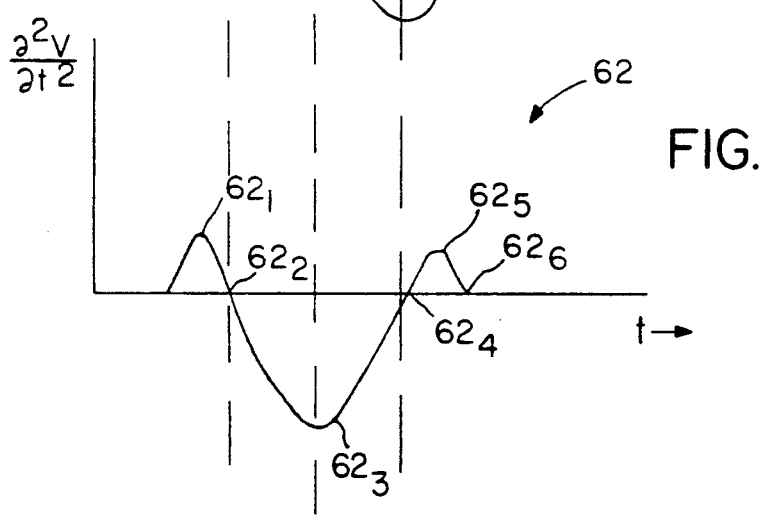
Figure 4:
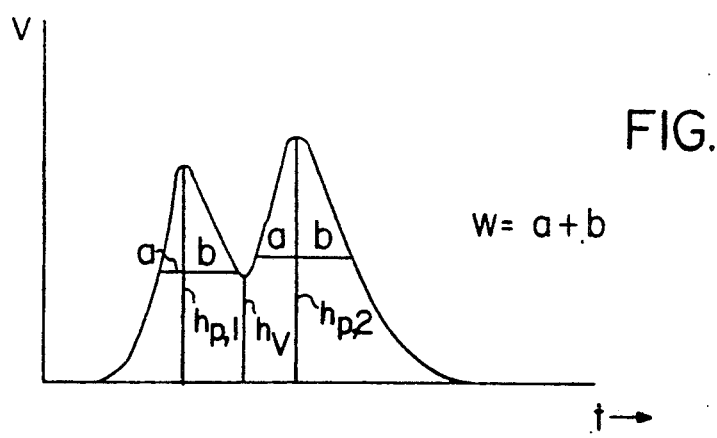
FIG. 4 illustrates the parameters used in one prior art method to characterize two fused chromatographic peaks.

For chromatograms, attribute definition 91 determines the second time derivative for each resolved peak and each fused peak combination in the minimum set of peaks. For example, as in FIG. 3C, the second derivative 62 with respect to time of positive resolved peak 60 starts to rise until the signal reaches a first positive maximum, a first extrema $62_1$. After the signal reaches the first positive maximum $62_1$, second derivative 62 decreases passing through zero. This is a first zero crossing $62_2$ of second derivative 62 and corresponds to a first inflection point of peak 60. After first zero crossing $62_2$, second derivative 62 continues to decrease until second derivative 62 reaches a maximum/minimum, a second extrema $62_3$. Second extrema $62_3$ of the second derivative 62 corresponds to the peak extremum of chromatographic peak 60. Hence, the time of second extrema $62_3$ is related to retention time $R_t$ for the component of the mixture represented by chromatographic peak 60. After passing through second extrema $62_3$, derivative 62 increases passing through a second zero point $62_4$, which corresponds to a second inflection point of peak 60, until derivative 62 reaches a second positive maximum, the third extrema $62_5$. After second derivative 62 passes through second positive maximum $62_5$, the signal decreases. After second derivative 62 goes to zero for a selected period of time, a fourth extrema $62_6$ for peak 60 is defined which corresponds to the end of the peak. A resolved negative peak also has four extrema.

Figure 6A:
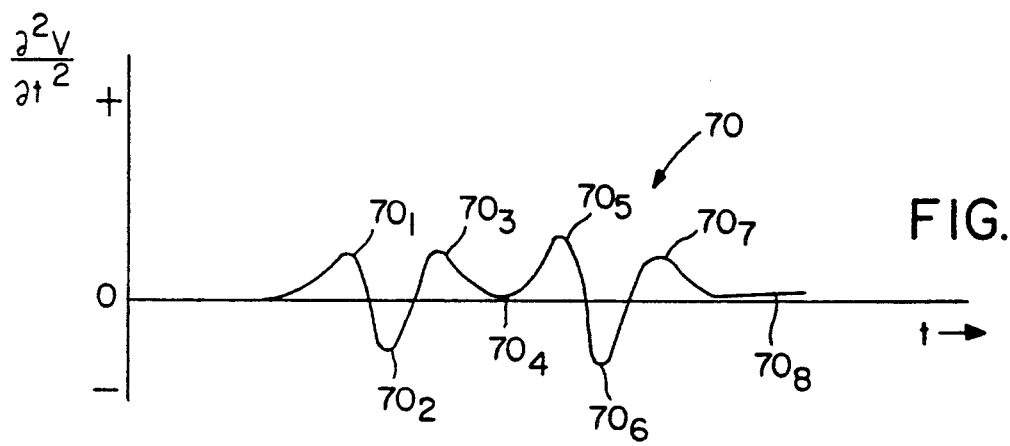
FIGS. 6A–6D illustrate the second time derivative for fused peak combinations encountered in chromatographic measurements.
Figure 6B:
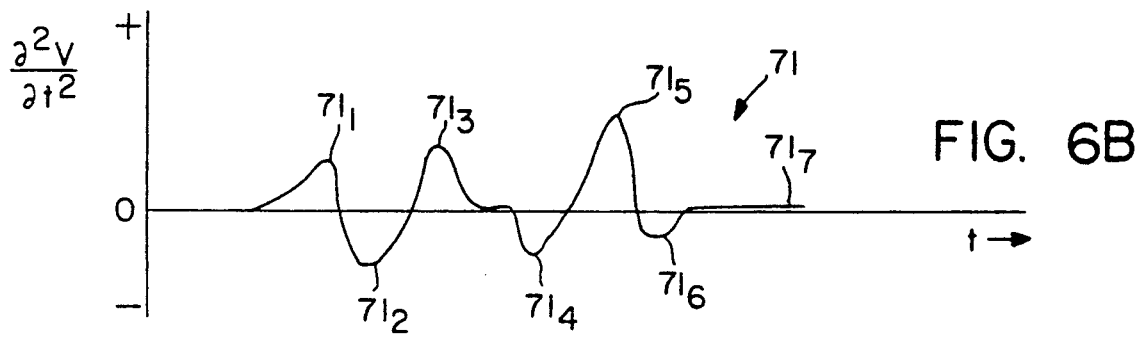
Figure 6C:
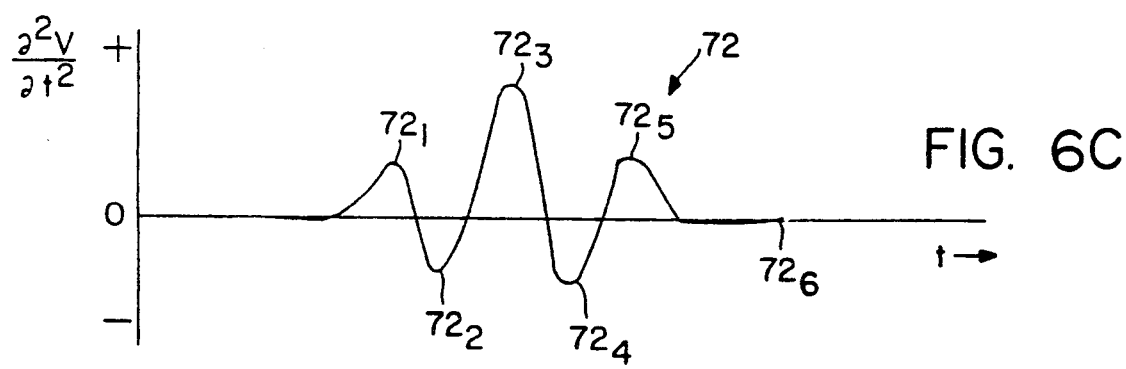
Figure 6D:
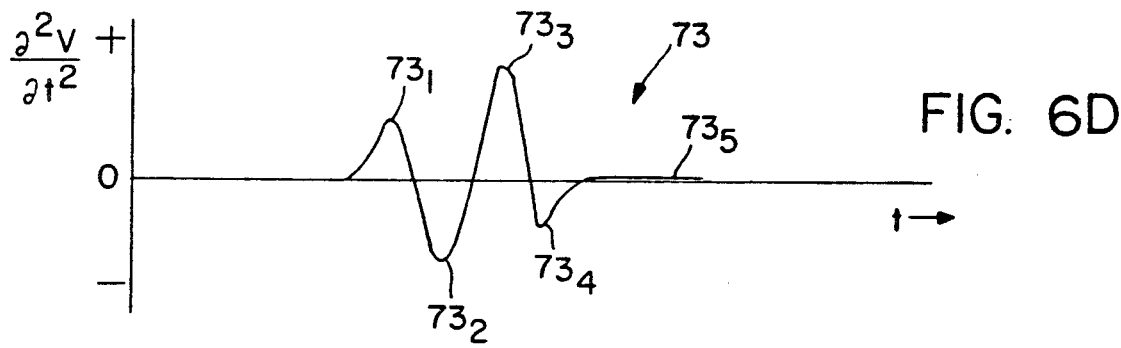

FIG. 6A illustrates the second time derivative 70 of slightly fused peaks of the same sign. The second derivative has eight extrema $70_1$–$70_8$. FIG. 6B illustrates the second time derivative 71 for slightly fused peaks of opposite sign, which has seven extrema $71_1$–$71_7$. FIGS. 6C and 6D illustrate the second time derivative 72 for strongly fused peaks of the same sign with five extrema $72_1$–$72_5$ and strongly fused peaks 73 of opposite signs with five extrema $73_1$–$73_5$ respectively. The waveforms in FIG. 3C and FIGS. 6A–6D represent calculated attributes of a resolved EMG peak and of combinations of pairs of EMG peaks.

Figure 7:
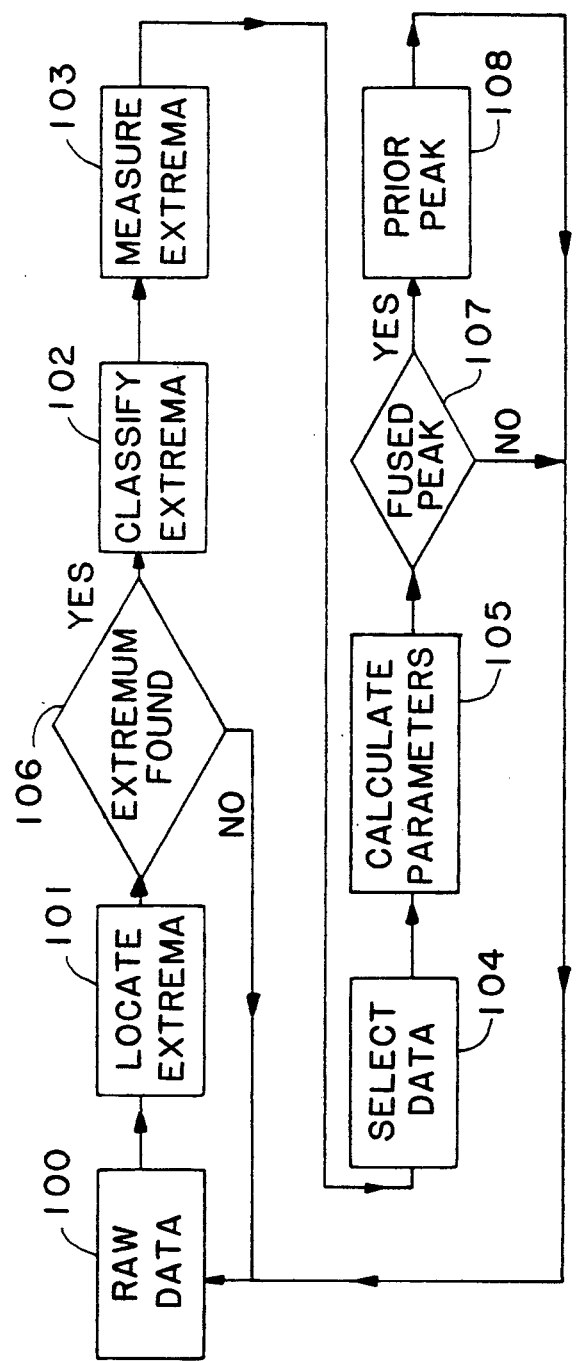
FIG. 7 is a more detailed block diagram illustrating one embodiment of a method for processing chromatographic data according to the principles of this invention.

In pattern recognition 92 (FIG. 5A), the characteristics of each second derivative from attribute definition 91 are analyzed, and a means for uniquely identifying each of the second derivatives is ascertained. In one embodiment of pattern recognition 92, an empirical set of rules for identifying each of the second time derivative traces was generated, as described more completely below with respect to classify extrema 102 (FIG. 7). These rules define relationships between the second derivative extrema for the various groups of peaks in the minimum set and thereby provides a means for identification of each of the second derivative traces. The features of the second derivative are used to distinguish between fused peaks, i.e., slightly and strongly fused, in the minimum set of peaks. Specifically, the unique characteristics of the second derivative of slightly fused peaks and strongly fused peaks are sufficient to uniquely identify the various degrees of of peak overlap that are encountered in chromatograms.

However, pattern recognition 92 (FIG. 5A) is not limited to a set of rules. A processing system, such as a neural network similar to those described more completely below, could be trained using second derivative extrema to identify each of the resolved peaks and combinations of resolved peaks in the minimum set. Alternatively, a neural net and a set of rules, similar to those described above, might be used. In this embodiment, the neural net is trained to generate a set of output signals, based upon input signals such as either the second time derivative or characteristics, e.g. extrema, extracted from the second time derivative. The neural net output signals are processed by the set of rules so as to identify the peak or peak combination represented by the input signals to the neural net.

The second derivative pattern recognition means 95 (FIG. 5A) generated by pattern recognition 92 provides, as described more completely below, a means for classification of measured data which does not require a prior baseline determination. While in this embodiment, the curvature for each resolved peak and each combination of resolved peaks in the minimum set has been used as the selected attribute for pattern recognition, in another embodiment another attribute can be selected.

With another attribute, iterations may be required between select attribute 91 and pattern recognition 92. For example, on a first iteration a selected attribute could be used in select attribute 91 and if a pattern recognition means cannot be successfully generated by pattern recognition means 92, a new selected attribute or a second selected attribute in combination with the first selected attribute must be generated by select attribute 91. This process continues until pattern recognition 92 produces a means for uniquely identifying the presence of each of the peaks and combinations of peaks in the minimum set.

Analyze data 93 and parameter set 94, as illustrated in FIG. 5B, are further subdivided, in one embodiment, into a five-step method that is used to generate a set of parameters which characterize each chromatographic peak detected. The five steps are: (1) locate extrema 101; (2) classify extrema 102; (3) measure extrema 103; (4) select data 104; and (5) calculate parameters 105. The first and second steps are included in analyze data 93 while the fourth and fifth steps are included in parameter set 94. As explained more completely below, measure extrema 103 is required for certain embodiments of calculate parameters 105 and can be considered as a part of either analyze data 93 or parameter set 94.

The principles of this invention are illustrated using chromatographic data which includes, for example, gaussian and exponentially modified gaussian (EMG) peaks. However, the method is applicable to any data having peaks with a characteristic shape. Accordingly, the principles of this invention may be used, for example, to determine a set of parameters which characterize generally chromatographic peaks, peaks associated with neutron activation analysis, or capillary zone electrophoresis peaks.

As illustrated in FIG. 7, digitized chromatographic data 100 are processed forward in time by locate extrema 101. Locate extrema 101 uses a series of digital filters, as described below, to calculate the characteristics of the second time derivative of data 100. Locate extrema 101 generates a data set, called an extrema file, which characterizes the second derivative extrema detected using the digital filters. The specific contents of the extrema file are also described more completely below. As used herein, the extrema file is a stored data set. In one embodiment, the data set is stored in the random access memory of a computer in which, as described more completely below, locate extrema 101 is an executing computer program. Alternatively, the data set can be stored on any storage device that is accessible by locate extrema 101 and by the subsequent operations that use the stored data.

Extrema found 106 performs two functions in this embodiment. The first function is to determine whether locate extrema 101 found an extremum. If no extremum was found, extrema found 106 returns control to raw data 100. If an extremum was found by locate extrema 101, the second function of extrema found 106 is to examine the extrema file and determine the number of extrema that have been detected. If less than four extrema have been detected, sufficient data are not available to identify a peak, because as shown in FIGS. 3C and 6A–6D the minimum number of extrema required to identify a peak is four. Accordingly, when less than four extrema have been detected, control is passed back to raw data 100 which supplies the next data bunch to locate extrema 101. Conversely, if a baseline and four or more extrema have been found, extrema found 106 passes the extrema file to classify extrema 102.

If a baseline has not been found, extrema found 106 passes the extrema file to classify extrema 102 when eight or more extrema have been found, because even if the raw data signal has not returned to baseline level, at least one peak must be included within the time range of the eight extrema. In one embodiment, as described below, extrema found 106 is included within classify extrema 102.

In this embodiment, when either a baseline and at least four extrema or more than eight extrema are contained in the extrema file, the extrema are processed by classify extrema 102, and classified as extrema representing either a resolved peak, sightly fused peaks of the same sign, slightly fused peaks of opposite sign, strongly fused peaks of the same sign, or strongly fused peaks of opposite sign. Classify extrema 102 classifies the characteristics of the second derivative extrema in the extrema file using the pattern recognition rules generated as described above. The specific rules are discussed more completely below.

In some prior art analyses, a second derivative of a chromatogram was used to identify the onset of a peak, and to detect the existence of peak shoulders. However, according to the principles of this invention, specific characteristics of the second derivative are used to classify peaks in a chromatogram as one of the peaks or combinations of peaks in the minimum set rather than to identify specific features of the peaks. Hence, more information is obtained about the chromatogram than in the prior art methods previously described.

After classify extrema 102 classifies the peak or peaks represented by the data in the extrema file, measure extrema 103 calculates the time and magnitude of the second derivative extrema for the identified peak or peaks. In a first embodiment which uses a neural net in calculate parameters 105, the precise location and magnitude of the second derivative extrema are an important aspect of the invention because the accuracy of subsequent processing of the data by the neural net is dependent upon the accuracy of the location and magnitude of the extrema. However, in another embodiment, subsequent processing is less sensitive to the exact location and magnitude of the extrema. In the first mentioned embodiment, a polynomial fit is used in measure extrema 103, but in the other embodiment, measure extrema 103 may possibly be eliminated. The important aspect is that a set of peak parameters containing characterizing information is provided for further analysis. This set of peak parameters includes the height of the peak crest, the time of the peak crest, the peak width, and a measure of the peak skewness. As explained more completely below, the set of peak parameters containing characterizing information is used to generate a characterizing set of parameters for each chromatographic peak.

After completion of measure extrema 103, select data 104 uses the information from classify extrema 102 and measure extrema 103 to prepare raw data 100 for processing by calculate parameters 105. The function of select data 104 is (i) to select a range of raw data 100 for processing by calculate parameters 105 based upon the classification of the data in the extrema file by classify extrema 102, and (ii) to remove contributions to the selected raw data from peaks other than the peak or peaks that are subsequently characterized by calculate parameters 105.

Figure 8A:
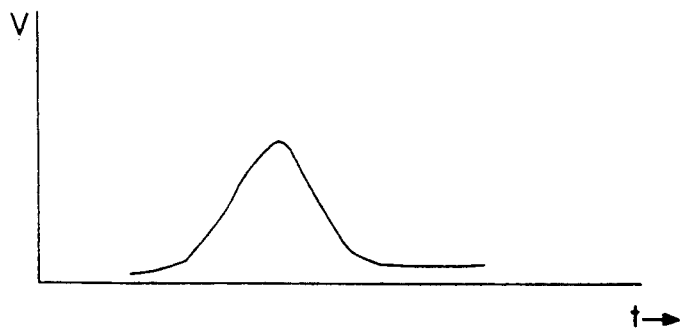
FIGS. 8A–8D illustrate resolved and fused peaks that are typical of chromatographic data.
Figure 8B:
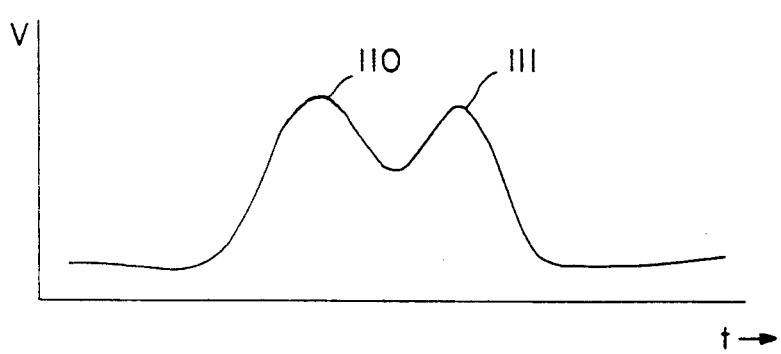
Figure 8C:
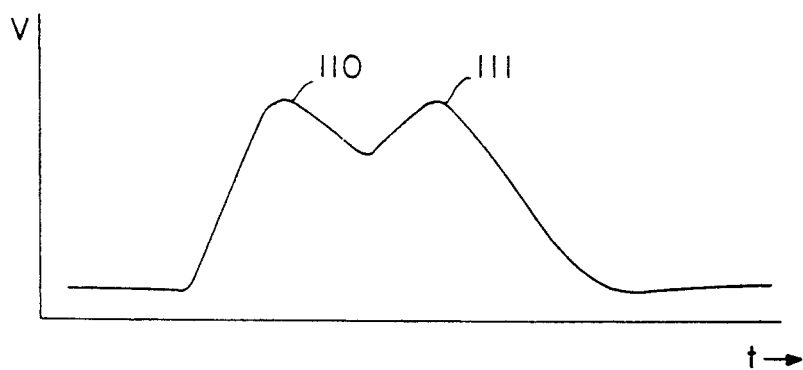
Figure 8D:
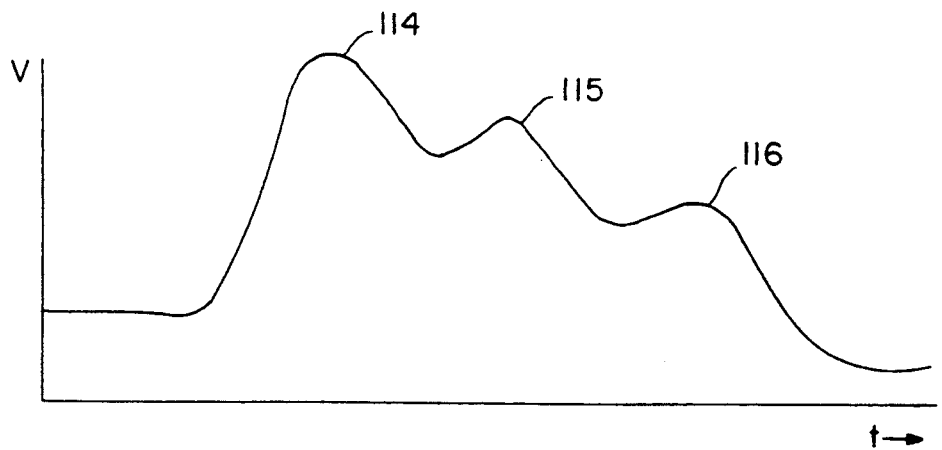

To illustrate the effect of classify extrema 102 upon select data unit 104, four different cases, illustrated in FIG. 8A through 8D, are considered. In the first case, peak 109 (FIG. 8A) is resolved. In the second case, as illustrated in FIG. 8B, two peaks 110, 111 overlap and first peak 110 is being analyzed. In the third case (FIG. 8C), two peaks 110, 111 again overlap but second peak 111 is being analyzed. In the fourth case (FIG. 8D), three peaks 114, 115, 116 overlap and middle peak 115 is being analyzed. In this embodiment, calculate parameters 105 processes only data corresponding to a resolved peak. Thus, select data 104 removes contributions from any adjacent peaks to the peak being analyzed.

While four cases are shown in FIGS. 8A through 8D, these cases are illustrative only of the principles of this invention and are not intended to limit the scope of the invention. In view of this disclosure, those skilled in the art can define additional or fewer cases, or alternative ways to process the data.

Since in this embodiment, calculate parameters 105 analyzes data for a single resolved peak and generates a set of parameters which characterize the single resolved peak and a baseline estimate, select data unit 104 must sequentially define the time range of the data corresponding to each of the peaks in FIGS. 8A-8D. In the first case (FIG. 8A), peak 109 is a resolved peak, and select data 104 determines the time range of data required by calculate parameters 105 and supplies only that data to calculate parameters 105. In the other cases, the contribution of the overlapping peak or peaks must be subtracted from the peak being analyzed, so that only data for a single peak remains.

Figure 9:
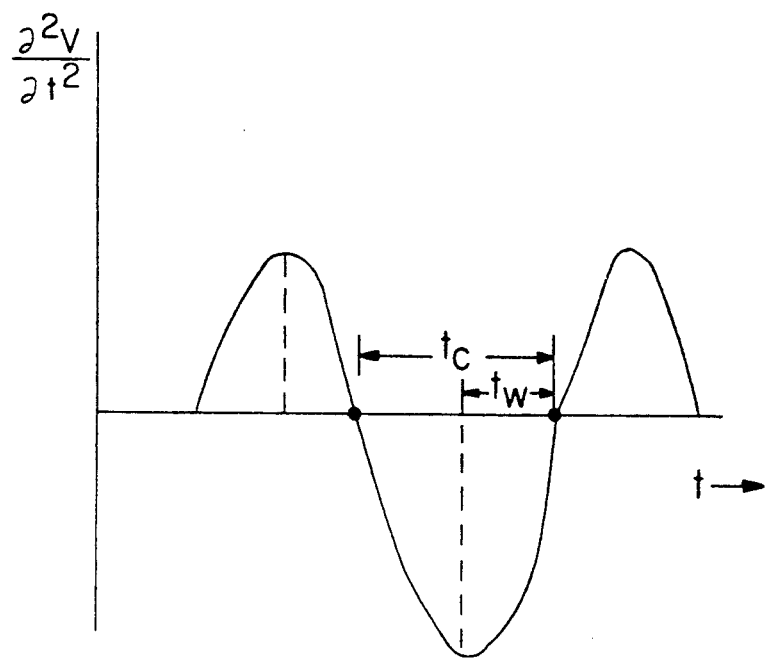
FIG. 9 illustrates the characteristics of the second time derivative of a positive resolved EMG peak which are used to calculate the signature ratio according to the principles of this invention.

In the second case (FIG. 8B), the shape of second peak 111 is estimated by select data 104 using the measured extrema for second peak 111. Specifically, a signature ratio CRATIO is formed for second peak 111. The signature ratio CRATIO is:

$$CRATIO = \frac{t_w}{t_c} \qquad (6)$$

where $t_w$ (FIG. 9) is the time difference between the time of the second extrema of the second derivative and the time of the second zero crossing and $t_c$ is the difference in time between the two zero crossings of the second derivative.

The time $t_c$ between the two zero crossings is a measure of the peak width at the inflection points of the peak. Time $t_w$ is the time from the peak crest to the trailing inflection point, which corresponds to the second zero crossing. Signature ratio CRATIO is a measure of the asymmetry of the peak. Consequently, signature ratio CRATIO uniquely defines the skewness of an EMG peak. Since signature ratio is defined using the time of the peak inflection peaks and the time of the maximum peak displacement, i.e. information about the peak crest, the signal-to-noise ratio for the data used to define the signature ratio is usually not affected by baseline level noise.

Signature ratio CRATIO is first used to estimate peak skewness. Peak skewness is used, as described more completely below, to provide an initial estimate of the peak width, the peak amplitude and the peak area. These estimated EMG peak parameters are used to calculate a trace for second peak 111 (FIG. 8C), i.e., the estimated EMG parameters are used in Equation 4 to generate an EMG curve as a function of time. The estimated trace for second peak 111 is subtracted from chromatographic data 100 so that corrected raw data corresponding to first chromatographic peak 110 is obtained. The data representing only first chromatographic peak 110 is passed to calculate parameters 105 which in turn determines the EMG parameters describing second peak 111.

In the third case (FIG. 8C), the second peak 111 of a pair of fused peaks 110, 111 is being analyzed. Accordingly, using the procedure described for case two (FIG. 8B), the EMG parameters describing first peak 110 have been ascertained by calculate parameters 105. Accordingly, the determined EMG parameters for peak 110 are used to define a trace of peak 110. This trace is subtracted from the raw data for fused peaks 110, 111 so that corrected raw data corresponding to second chromatographic peak 111 is obtained. The corrected data representing only second chromatographic peak 111 is passed to calculated parameters 105 which in turn determines the EMG parameters describing second peak 111.

In the four case (FIG. 8D), here the peak being analyzed 115 is overlapped by a prior peak 114 and a trailing peak 116, a combination of the second and third procedures, described above, is used. In this case, prior peak 114 has been characterized and a trace for peak 114 is generated using the determined parameters as described for the third case above. This trace is subtracted from the raw data so that data for second and third peaks 115, 116 remains. The signature ratio, defined above in the second case, is used to determine a trace for third peak 116, the trailing peak. The trace for peak 116 is subtracted from the raw data for second and third peaks 115, 116 to leave raw data corresponding to second chromatographic peak 115. Using these four cases, various combinations of fused chromatographic peaks can be successfully analyzed.

In the above description, combinations of fused peaks were separated into resolved peaks by select data 104. In another embodiment, select data 104 first determines whether a prior peak has been analyzed and, if so, select data 104 subtracts the contribution of the prior peak from any trailing peak or peaks. Calculate parameters 105 then analyzes either the remaining peak or the next pair of fused peaks. Accordingly, in this embodiment the fused peaks are not separated into a series of resolved peaks, but rather pairs of fused peaks are analyzed, as described more completely below, by calculate parameters 105.

Select data 104 and calculate parameters 105 may have several different embodiments. The important aspect of this invention is that select data 104 prepares the raw data and presents the data in a form that is appropriate for the processing used in calculate parameters 105 to generate a set of parameters which characterize the detected peak.

The processing used in calculate parameters 105 is broken into three general categories: (1) lookup tables, (2) neural network analysis, and (3) curve fitting analysis, e.g., Simplex fitting analysis. Lookup table analysis is equivalent to the signature ratio CRATIO analysis, described above, and is used to generate parameters for each resolved peak. A specific embodiment using the signature ratio CRATIO is described below. Neural network, Simplex analyses or other curve fitting methods may be used individually or in combination as described more completely below.

Independent of the method used to calculate parameters that characterize a peak, calculated parameters 105 is fundamentally different from the prior art methods described above. First, data including a baseline signal is processed by calculate parameters 105 to generate a set of characterizing parameters and a baseline estimate. In contrast, the prior art methods previously discussed estimated a baseline, corrected the raw data with the baseline estimate and than used the baseline corrected data to estimate a set of characterizing parameters. Thus, these prior art methods used a prior baseline correction while in my invention, the set of peak characterizing parameters and a baseline estimate are determined together. Thus, any errors introduces by a prior baseline estimate are eliminated, and a best fit to the data for a peak with a baseline is determined.

In a first embodiment, after identification of data representing the chromatographic peak by select data 104, calculate parameters 105 uses an iterative curve fitting process to adjust the EMG parameters until an optimal fit to the data is found. The optimality of the fit is measured by subtracting the currently estimated peak line shape, sometimes called the peak trace, plus baseline estimate from the selected raw data and assuming the squares of the differences between the estimated peak line shape plus baseline estimate and the selected raw data over the selected raw data region.

In one embodiment, the baseline is estimated at each of the iterations by selecting the baseline to insure that the error function is zero at the beginning and ending points of the selected raw data region. The baseline is linearly interpolated between the start and end points.

In another embodiment, the baseline is determined by finding the straight line fitting the difference of the raw data and the currently estimated peak line shape by the minimum least square criterion. The parameters describing the line $y = a + b*x$ are found by using:

$$a = \frac{\Sigma x_i \Sigma x_i y_i - \Sigma x_i x_i \Sigma y_i}{\Sigma x_i \Sigma x_i - \Sigma x_i x_i \Sigma 1_i} \quad (7)$$

$$b = \frac{\Sigma x_i y_i \Sigma 1_i - \Sigma x_i \Sigma y_i}{\Sigma x_i x_i \Sigma 1_i - \Sigma x_i \Sigma x_i}$$

where
$x_i$ = the integer index for the ith data point
$y_i$ = raw data value for ith data point minus candidate line shape value for the ith data point.

The summations in Equation 7 extend over the range of data identified by select data 104. In these embodiments, the baseline is determined as the parameters describing the peak are ascertained, unlike prior art methods, described above, which subtract the baseline from the raw data and then deduce the parameters describing the peak.

In another embodiment, calculate parameters 105 generates curvature data using the data provided by select data 104. The curvature data are input signals to a neural net. The neural net, which has been previously taught to determine EMG peak parameters based upon curvature input signals, generates output signals corresponding to the EMG peak parameters best describing the input signals. The neural net processing is more than thirty times faster than the iterative approach described above. After generation of the EMG peak parameters by the neural net, in one embodiment a Simplex fit process uses the neural net EMG peak parameters as an initial estimate, as described below, to obtain EMG parameters that accurately reproduce the raw data.

In yet another embodiment, calculate parameters 105 uses two neural nets for resolved peaks and a Simplex fit for all combinations of fused peaks. This embodiment provides the greatest degree of accuracy in the generation of the sets of parameters which describe the peaks while maintaining an optimal processing time.

After calculate parameters 105 determines an estimated set of parameters for the peak currently being analyzed, the extrema for that peak are removed from the extrema file and then fused peak 107 (FIG. 7) tests to determine whether classify extrema 102 indicated that the current peak was part of a fused peak sequence. If the peak was not part of a fused peak sequence, processing returns to raw data 100 which provides the next data point to locate extrema 101 and the process continues.

Alternatively, if the peak being analyzed by calculate parameters was part of a fused peak sequence, fused peak 107 passes control to prior peak 108. Prior peak 108 sets a flag indicating that a prior peak was analyzed and then returns control to raw data 100. The prior peak flag is used in select data 104 to ascertain whether a prior peak exists and the information from classify extrema 102 is used by select data 104 to ascertain whether a following peak is included in the sequence. The process, illustrated in FIG. 7, is repeated until all of the data in raw data file 100 have been analyzed.

The peak processing system of FIG. 7 is incorporated, in one embodiment, in an automated chromatographic data processing system. The system, illustrated in FIG. 10A, includes a chromatographic detector 105, an integrator 154, and a computer 153. Integrator 154 includes a analog-to-digital converter 151 and a processing unit 155. Analog-to-digital converter 151 includes voltage-to-frequency converter $151_1$, a counter $151_2$, and a timer $151_3$. Computer 153 includes a display terminal $153_1$, a central processing unit $153_2$, keyboard $153_3$, and a storage medium 152.

In a typical chromatographic analysis, a sample 142 is introduced to chromatographic column 144 through control valve 143. After the sample introduction, control valve 143 is positioned so that an eluent provided from eluent storage tank 140 by pump 141 is passed through column 144. As described previously, the eluent causes the components of the sample to move through column 144 at varying rates. Detector 150 generates an output signal that varies with time, i.e., a time varying voltage, as the components in the sample migrate through detector 150.

The detector output signal is processed by a voltage-to-frequency converter $151_1$. Converter $151_1$ is an oscillator which pulses at a rate proportional to the voltage signal from detector 150. Counter $151_2$ counts the number of pulses from converter $151_1$ for a period of time which is selected by timer $151_3$. The output signal from counter $151_3$ is the number of counts in the selected time interval.

The output of converter $151_1$ is processed by processing unit 155 to form data bunches, as described below, and the data bunches are passed to CPU $153_2$ which in turn stores the data on storage medium 152 such as a computer floppy disk, a computer hard disk, a computer tape, or perhaps a punched paper tape or some other means for saving the data so that the data can be recovered and analyzed.

Selection and operation of detector 150, integrator 154 and computer 153 as well as chromatographic column 144 are known to those skilled in the art. For example, as described above, detector 150 may be a fluorescence detector, an absorbance detector, or a detector which measures refractive index.

Figure 10B:
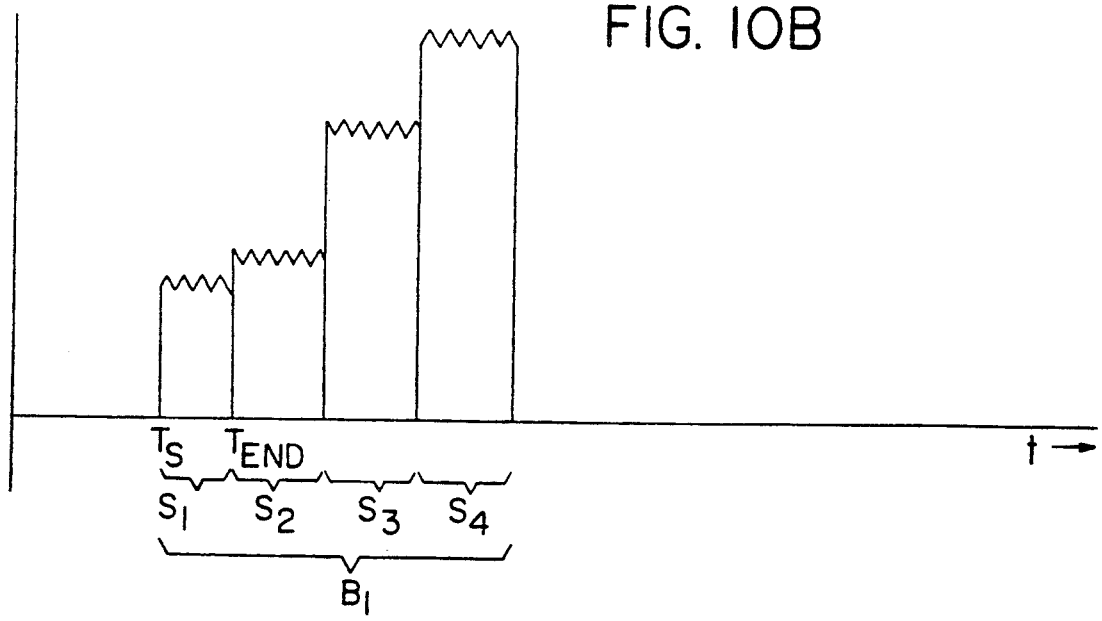
FIG. 10B illustrates data samples and data bunches as used in this invention.

FIG. 18B illustrates in more detail the conversion of the detector voltage versus time signal to a data sample which is stored on storage medium 152. Each data sample starts at a time $T_s$ and end sat a time $T_{end}$ and the number of oscillations of voltage-to-frequency converter $151_1$ is counted over this period and is represented by the vertical area between $T_s$ and $T_{end}$ in FIG. 10B. In one embodiment, the duration of the data sample, i.e., the time interval between $T_s$ and $T_{end}$, is equal to the period of the power line frequency. Thus at 60 Hz, the data sample is for 16 170 milliseconds while at 50 Hz the data sample is for 20 milliseconds. Data samples $S_1$, $S_2$, $S_3$, $S_4$ are contiguous as shown in FIG. 10B. A selected number of data samples, for example, samples $S_1$, $S_2$, $S_3$, $S_4$ are summed to form a data bunch $B_1$ for the selected time interval.

Hence, in a preferred embodiment, the data processed according to the principles of this invention consists of a time series of contiguous data bunches with each data bunch having an area which is related to the material passing through the chromatographic column during that period of time. As explained more completely below, the data samples are summed to form data bunches, because this allows improvement in the signal-to-noise ratio.

More importantly, data bunching is used to optimize the data sample size for characterization of individual chromatographic peaks. For example, the optimal data bunch size for characterization of a one-second duration peak obtained using a gas chromatographic capillary column is not the same as the optimal data bunch size for n amino acid peak which may be as much as five minutes wide. According to the principles of this invention, the number of data bunches between the inflection points of a chromatographic peak is a constant irrespective of the peak width. This constant is in the range of about 6–12 data bunches because empirical results have indicated that the best estimate of a set of parameters which described each peak is obtained with such a grouping of the data.

To analyze a time series of digital data representing a chromatographic trace according to the principles of this invention requires knowledge of: (i) the total number of data bunches, (ii) the number of data samples in each data bunch, (iii) the time width of the minimum bunch size, (iv) a threshold value, (v) the number of filters used in locate extrema 101 (FIG. 7), and (vi) time base information including a) whether the A/D conversion was based upon 50 Hz or 60 Hz, b) whether the retention times are in minutes or seconds and c) a scale factor to convert the indices for the data to a time. These six items are collectively referred to hereinafter as "initialization data".

In one embodiment, chromatographic data is obtained using a Spectra-Physics gradient liquid chromatography pump solid under Spectra-Physics part No. SP8800-01. The pump is used with a chromatographic column and a Spectra-Physics liquid chromatography UV-visible detector with single/dual wavelength and scanning modes, ratio output, timed wavelength changes, and automatic fraction collector advance and sold under part No. SP8490-010. The detector is connected to Spectra-Physics computing integrator model No. SP4270, Part No. SP4270-010. The computer integrator performs the A/D conversion and data sample generation, explained previously, and is connected to a microcomputer having WINner workstation software package, supplied by Spectra-Physics under part No. WINner-010, installed and operating.

The specific Spectra-Physics components and software described herein are not essential to this invention and are provided only to indicate commercially available apparatus that may be used to generate data for processing according to the principles of this invention. These instruments are described in a publication entitled "Chromatography Instruments and Systems," available from Spectra-Physics, Auto Lab Division, 3333 North First Street, San Jose, Calif., 95134.

The above Spectra-Physics automated chromatography system provides (i) compressed data and (ii) method files which specify data need for integration and generation of summary reports from the compressed raw data. Typically, the compressed raw data are stored in data bunches having a width of about 0.1 seconds.

Since the automated system generates compressed raw data, prior to processing the data according to the principles of this invention the compressed raw data are retrieved from the hard disk by preprocessing software and processed to form a series of contiguous data bunches with each data bunch having the same time interval. The time interval of the data bunch is referred to as a time window. Each data bunch has a single index to identify the bunch.

In addition to defining the total number of data bunches, the number of data samples in a bunch, and the time width of the minimum bunch size, the preprocessing software also requires the user to specify the threshold value and the number of filters, sometimes called detectors, to be used. One embodiment of the preprocessing software is provided in Microfiche Appendix A and incorporated herein by reference. The preprocessing software is dependent upon the measurement apparatus and therefore is probably different for different apparatus. The important aspect of any preprocessing package is that the package provides the data initialization items described above.

Figure 10A:
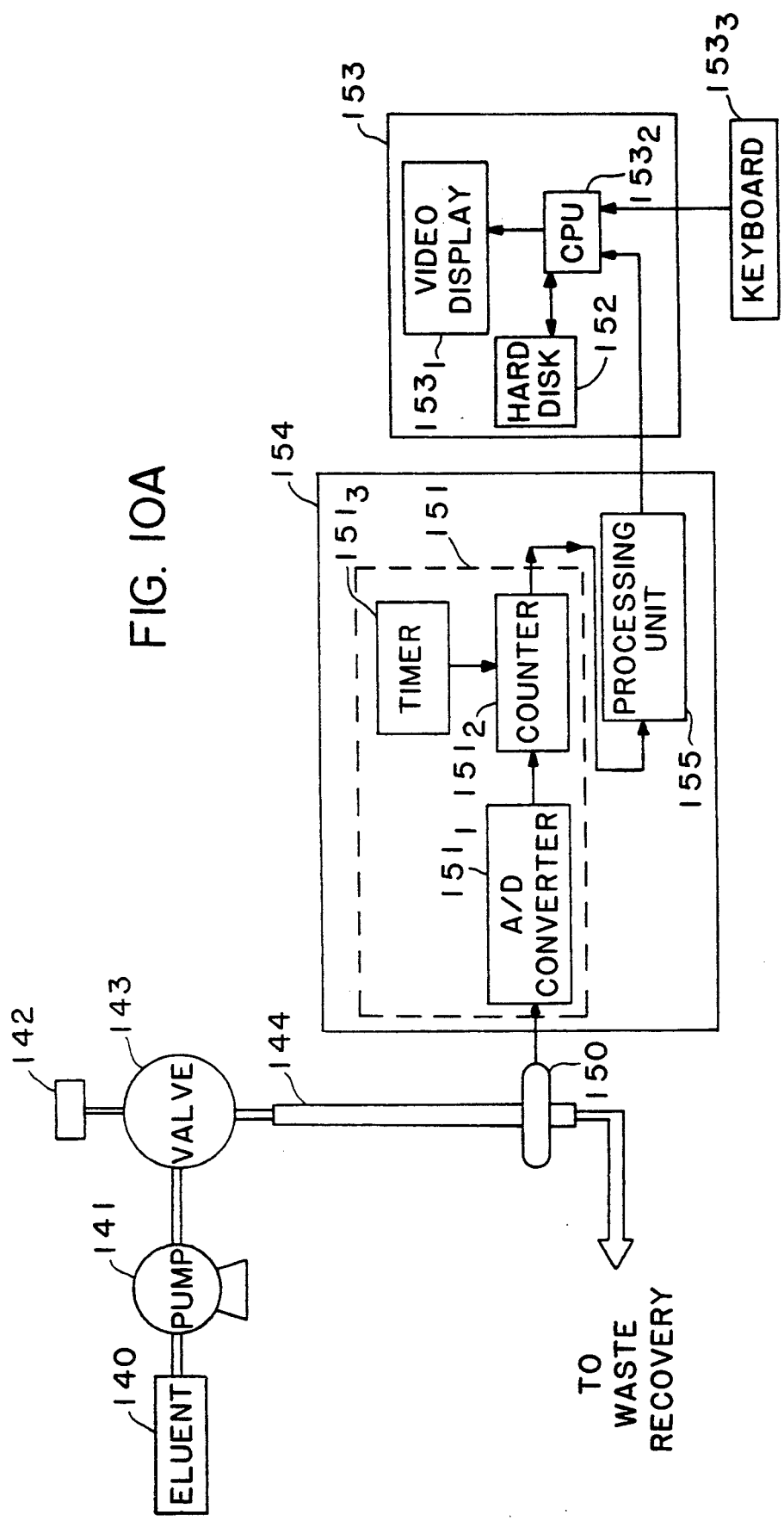
FIG. 10A is an illustration of one ebodiment of an automated chromatographic system suitable for generating raw data 100 which is processed according to the principles of this invention.

While this invention may be implemented with hardware to process the digitized time series data representing the chromatogram, in one embodiment the processing is performed by a computer program in microcomputer 153 (FIG. 10A). Microfiche Appendix A, incorporated herein by reference, also includes one embodiment of the peak processing system of this invention. The computer program listing in Microfiche Appendix A is written in the C programming language. However, the specific language used is unimportant and any high level computer language or even assembly language for a specific microprocess could be used to implement the principles of this invention as described herein.

The five steps in the peak characterization process, as illustrated in FIG. 7, are included within a main program which controls the input data and the overall processing. As previously described, the time series of digital data is initially processed by locate extrema 101 (FIG. 7). However, prior to initiation of locate extrema 101, several variables, which are used in the analysis, are initialized in the main program. Specifically, a threshold level is obtained from the preprocessing routines. A preprocessing package is not required to provide the initialization data for the main program. The initialization data, in another embodiment is coded directly in the main program.

When the digitized data has a value less than the threshold level for a selected period of time, a baseline is defined. The threshold level is not a fixed number which can be used for all analyzes of chromatographic data, but rather the threshold must be determined for each series of chromatographic measurements obtained with a specified experimental apparatus.

Typically, a level portion of a chromatogram may be used to define the threshold level as previously described. Alternatively, a threshold level is defined by passing an eluent through a chromatographic column, a blank run, and quantifying the detector output signal for the blank run. Other means for defining a threshold level are known to those skilled in the art.

To calculate the second derivative of raw data 100 (FIG. 7) each data point in raw data 100 is sequentially processed. After processing each data point, locate extrema 101 indicates either that an extremum has been found or that no extremum has been found. If no extremum has been found, the next data point is analyzed. Alternatively, if an extremum has been found, an extrema file, described more completely below, is passed to classify extrema 102.

As previously described, according to the principles of this invention, locate extrema 101 uses a series of digital filters to identify extrema of the second time derivative of the digitized data. Each of the digital filters determines the second time derivative of the data at a selected data point, data index, using a constant number of data points on either side of the selected data point.

Conceptually, a shift register holds the data points for each filter. The time span of adjacent shift registers differ by a factor of two. After calculation of the curvature for the data in a shift register, a new data point is shifted into the shift register, and the earliest data point in time is shifted out of the shift register.

The embodiment of the digital filters described herein is not intended to limit the scope of the invention but rather is illustrative only of the principles of the invention. In one embodiment, the digital filter was $$G_i''(t) = 2''g(t-2) - g(t-1) + 2^*g(t+2) \qquad (8)$$

Digital filter $G_i''(t)$ requires five data bunches, e.g., data from a five bunch shift register, to generate curvature $G_i''(t)$ for point t. As used herein, the indices t-2, t-1, t, t+1 and t+2, are integers used to denote data bunches. Each data bunch has a corresponding time window. The subscript i is used to denote the filter. For i=0, the filter time window has the smallest size and in one embodiment, for i=6 the filter time window has the largest size which is sixty-four times greater than the smallest time window. The time windows of adjacent filters differ by a power of two. In one embodiment, the number of filters used is provided by the data preprocessing package, e.g., the number is user selected.

FIG. 1 illustrates the relationship between digital filters $G_i''(t)$ used to identify extrema of the curvature according to the principles of this invention. The data bunches for filters $G_0''(t)$, $G_1''(t)$ are represented by the dashed lines 160, 161, 162. The length of each segment in a line, for example segments $160_1$, $160_2$, $160_3$, ..., of line 160, are the same and each segment represents the time size of the data bunch for the filter. The time size of the data bunch for the filter is a characteristic interval for the filter. The length of the segments in adjacent lines, for example $160_1$ in line 160 and segment $161_1$ in line 161, differ by a factor of two. In fact, the data bunch for segment $161_1$ is obtained by adding data bunches $160_1$ and $160_2$ together. The other data bunches in line 161 are obtained from the data bunches in line 160, and similarly the data bunches in line 162 are obtained from the data bunches in line 161.

In this embodiment, the minimum time window size is $t_i$ and the maximum window size (not shown) is $64^*t_i$ for a total of seven different filter sizes. In FIG. 10, only the data bunches for the first three filters $G_0''(t)$, $G_1''(t)$, $G_2''(t)$ are represented. The first filter has a time window width $t_i$. The second filter window has a width of $2^*t_i$ and the third a width of $4^*t_i$. Thus, each filter has a different characteristic interval and the characteristic intervals differ by an integer multiple.

In one embodiment, minimum time window $t_i$ for line 160 is defined by the preprocessing package. Typically, a system such as that in FIG. 10A uses a default of about 0.1 second for the minimum bunch size. If 60 Hz is used in A/D converter 151 (FIG. 10A) so that each data sample is 16 ⅔ milliseconds, the number of data samples is about 6 in the 0.1 second minimum bunch size. This embodiment is illustrative only and is not intended to limit the scope of the invention. The important aspect is that the peak processing system of this invention is provided the minimum time width for the data which is being processed by the system.

For each set of data, as represented by lines 160, 161, 162 (FIG. 11), the curvature is not calculated until filter $G_i''(t)$ is centered on the third data bunch $G_i''(3)$ because there are not sufficient data bunches to calculate curvature $G_i''(t)$ until the third data bunch. Since chromatographic data scans typically have a baseline preceding the first peak, this limitation should not result in the loss of any information. However, with other filters or other applications of the curvature, average values or some other representation for two data bunches to the left of the initial data bunch, $160_1$, $161_1$, $162_1$ could be used so as to determine the curvature for each of the measured data bunches. Similarly, the curvature is not calculated for the last two data bunches in raw data 100 (FIG. 7). As used herein, the phrase "calculate the curvature for each data point in a data set" means calculating the curvature for the data points for which the curvature is defined, i.e., all the data points except the first two and last two in the data set.

As described more completely below, locate extrema 101 first calculates curvature $G_0''(t)$, and then sequentially $G_1''(t)$ to $G_6(t)$. The processing by locate extrema 101 is terminated when (i) all the filters have processed the current data bunch and no extremum was found; (ii) an extremum is located; (iii) a filter is encountered for which sufficient data bunches are not available to use the filter; or (iv) the index of the current data bunch times the minimum bunch size is not evenly divisible by the time window for the current filter.

The tests for terminating processing by locate extrema 101 are straightforward with the possible exception of test (iv). The fourth test is used to maintain proper alignment of the filters. A brief example will more clearly demonstrate the operation of the fourth test. In this example, only tests (i) and (iv) are used. Assume that the data bunch index is currently pointing at the seventeenth data bunch $160_{17}$ (FIG. 11) in the raw data file. Since $17t_i$ divided by $t_i$ is 17, the current data bunch $160_{17}$ is evenly divisible by the time window for filter $G_0''(t)$. Hence, the current data bunch is loaded in the data shift register for filter $G_0''(t)$ and curvature $G_0''(15)$ is calculated.

After locate extrema 101 processes curvature $G_0''(15)$ locate extrema 101 shifts to the next filter $G_1''(t)$ with a time window $2t_i$. The current data bunch remains $17t_i$ and $17t_i$ is not evenly divisible by $2t_i$ so that test (iv) returns processing to the main program indicating that no extremum was found. The reason for returning processing is that, in this embodiment, the leading edges of the filters are kept aligned and sufficient data is not yet available to define data bunch $161_9$.

The main program again calls locate extrema 101 and the data bunch index is pointing at the eighteenth data bunch $160_{18}$. Since $18t_i$ is evenly divisible by $t_i$, data bunch $160_{18}$ is loaded in the data shift register for filter $G_0''(t)$ and curvature $G_0''(16)$ is calculated. After locate extrema 101 processes curvature $G_0''(16)$, locate extrema shifts to the next filter $G_0''(t)$ with a time window $2t_i$. Since $18t_i$ is evenly divisible by $2t_i$, data bunch $161_9$ is loaded in the data shift register for filter $G_1''(t)$ and curvature $G_1''(7)$ is calculated. Notice that the forward time edge for curvature $G_1''(7)$ is aligned with the forward time edge for curvature $G_0''(16)$.

After locate extrema 101 processes curvature $G_1''(7)$, locate extrema shifts to the next filter $G_2''(t)$. However, $18t_i$ is not evenly divisible by $4t_i$ so that filter $G_2''(t)$ is not processed, and test (iv) returns processing to the main program indicating that no extremum was found.

The main program again calls locate extrema 101 with the data bunch index pointing at the nineteenth data bunch $160_{19}$. Since $19t_i$ is evenly divisible by $t_i$, curvature $G_0''(17)$ is calculated. However, $19t_i$ is not evenly divisible by $2t_i$ so that processing is again transferred back to the main program by test (iv).

Upon the subsequent call to locate extrema 101, the data bunch index is pointing at the twentieth data bunch $160_{20}$. Since $20t_i$ is evenly divisible by $t_i$, $2t_i$ and $4t_i$, curvatures $G_0''(18)$, $G_1''(8)$ and $G_2''(3)$ are each sequentially calculated by locate extrema 101. Again the forward time edge for $G_0''(18)$ is aligned with the forward edge of the curvature calculated by filter $G_1''(8)$ which is also aligned with the forward edge for curvature $G_2''(3)$.

The purpose of the fourth test as demonstrated in the above example is to keep the filters used in locate extrema 101 properly aligned so that the leading edge of each filter remains aligned. This alignment results in the most reliable means for locating curvature extrema of the data. However, extrema can also be located by maintaining alignment of the centers of each filter used. Thus, according to the principle of this invention a portion of each digital filter is aligned with a portion of each of the other digital so as to locate and identify extrema of the second derivative, as explained below. Moreover, as previously explained, the second time derivative is an attribute of the chromatogram and the extrema of the second time derivative are characteristics of that attribute. Thus, the digital filters as described herein, determine characteristics of an attribute of measured data.

The data bunching and the time windows used for curvature filter $G_i''(t)$ are important aspects of this invention. If only a very small time window, i.e. narrow data bunches, was used, any noise on the chromatographic trace would be effectively amplified and the analysis of the data would be difficult. Similarly, if only a very board window was utilized, information would be effectively averaged over the window and information may be lost. Accordingly, curvature filter $G_i''(t)$ is used sequentially with an increasing window size, as illustrated in FIG. 11, and the curvature calculated by adjacent filters is compared to identify extrema of the curvature.

Figure 11:
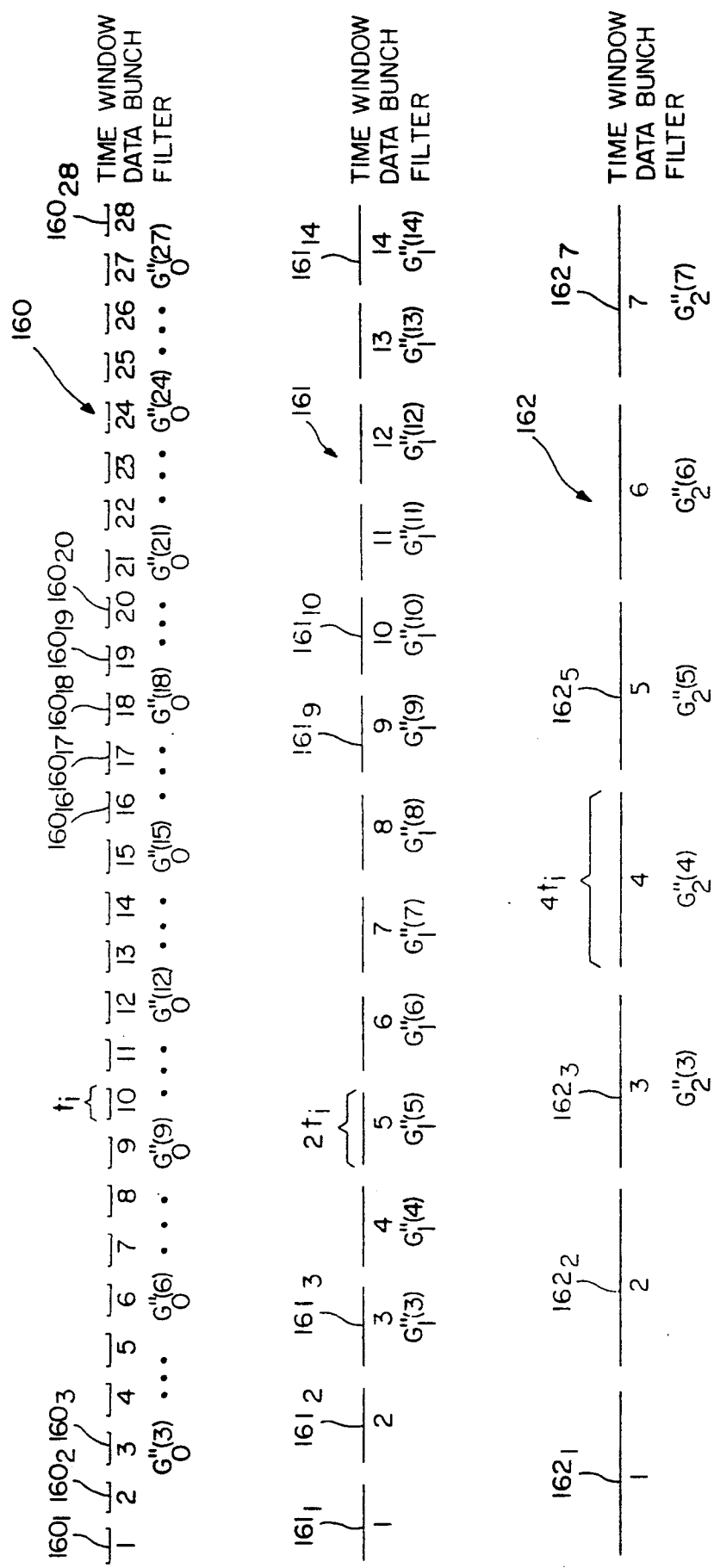
FIG. 11 is an illustration of the data filter in locate extrema 101 according to the principles of this invention.

For example, in FIG. 11, a calculated curvature for five data bunches in line 161 is compared with a curvature calculated for five data bunches in line 160 and with a curvature calculated for five data bunches in line 162. The output signal from each of the filters, the curvature, is scaled as described below so that the filter output signals can be compared directly. Specifically, measures of the curvatures produced by the different filters are compared.

Two comparisons of the curvature measures are made. A first comparison determines whether the measure calculated for the group of data bunches being processed by the filter is a better estimate of an extremum of the curvature than the prior best estimate of the extremum of the curvature which has been stored. A second comparison determines whether the stored best estimate of an extremum represents an extremum of the curvature. For example, in FIGS. 3A and 3C as the filters process the data corresponding to peak 60 the stored best estimate of first extremum $62_1$ increases as the data bunches being processed move towards the first extremum but when the calculated curvature moves past the first extremum the curvature decreases which indicates that stored value represents first extremum $62_1$ of the curvature.

Figure 12:
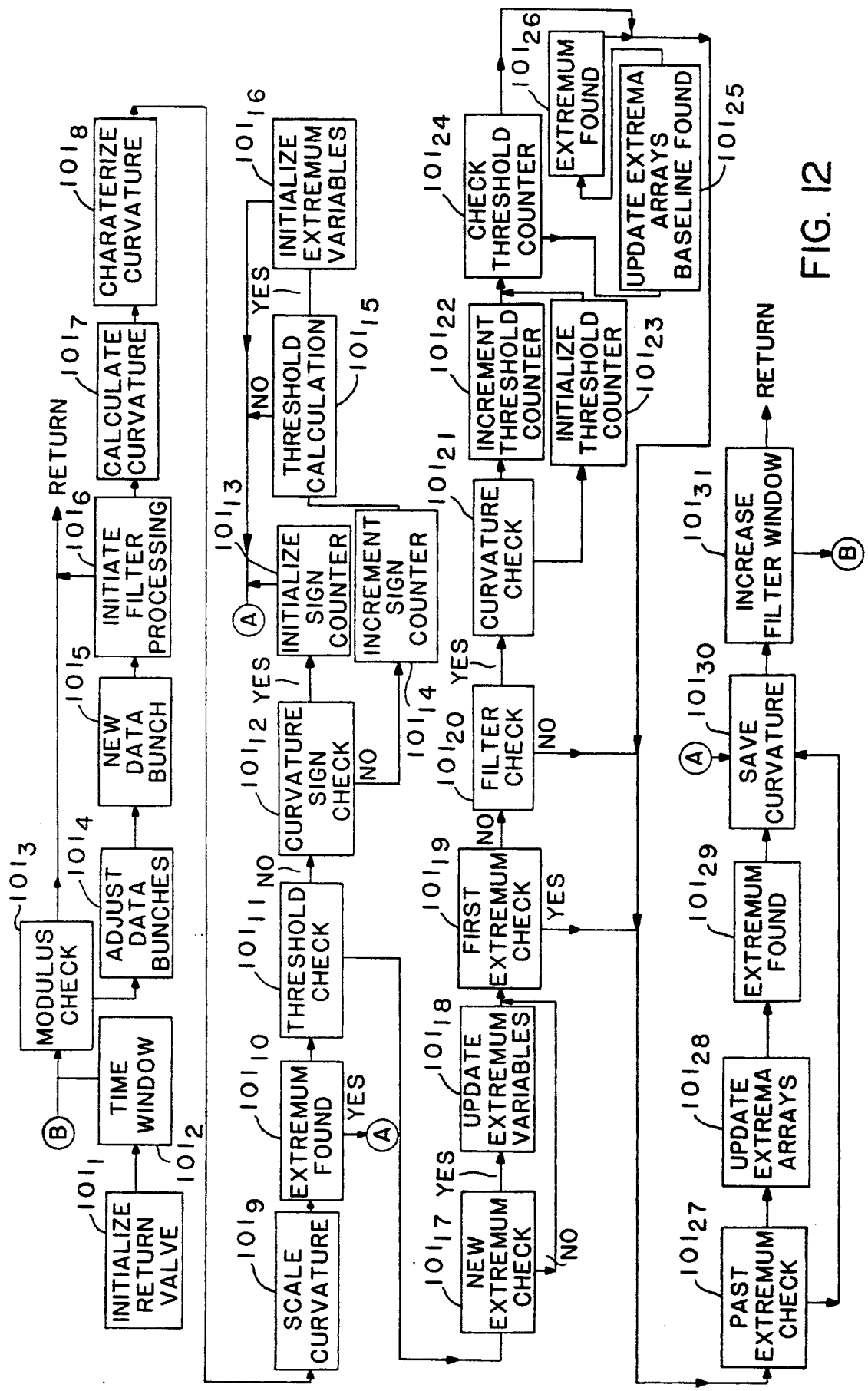
FIG. 12 is a detailed block diagram illustrating on embodiment of locate extrema 101 according to the principles of this invention.

One embodiment of the process used in locate extrema 101 is shown in FIG. 12. (See Appendix A). In the initialization of the main program prior to locate extrema 101 processing, the last two terms, $G(t+1)$ and $g(t+2)$, on the right hand side of Equation 8 are initialized to the zeroth and the first data bunch respectively for each filter. This operation corresponds to initializing the data shift register, described previously, for each filter. This initialization is not an essential aspect of the invention, but, as described below, storing data used in Equation 8 minimizes data input and output to locate extrema 101.

Upon entry to locate extrema 101 from the main program, an extremum found flag is set to indicate that no extremum was found by initialize return value $101_1$. Time window $101_2$ sets the first filter time window to the minimum bunch size. Modulus check $101_3$ determines whether the index for the current data bunch is an integer multiple of the time window for the current filter, a described above. If the data bunch is not an integer multiple of the time window, processing returns to the main program. Otherwise, the data bunches for the last four terms on the right hand side of Equation 8 are shifted one position to the left so that $G_i(t-1)$ becomes $G_i(t-2)$, $G_i(t)$ becomes $G_i(t-31\ 1)$, $G_i(t+1)$ becomes $G_i(t)$ and $G_i(t+2)$ becomes $G_i(t+1)$ by adjust data bunches $101_4$. This operation prepares the current filter data shift register for updating with the most recent data bunch. This manipulation of the terms used in the filter eliminates retrieving all five terms from an external storage device each time locate extrema 101 calculates a curvature. New data bunch $101_5$ retrieves a new data bunch which is assigned to $G_i(t+2)$ (See Equation (8)).

After the terms in $G_i''(t)$ are defined, the index for the data bunch being processed is checked by initiate filter processing $101_6$ to determine whether the data bunch is the third or greater data bunch for the current filter. If the data bunch is the first or second data bunch for the filter, processing returns to the main program. In this case, unless an extremum was found, as described below, the main program increments the data bunch index to the next data bunch and then returns to locate extrema 101.

If the data bunch is the third or greater data bunch for the filter, all the terms in $G_i''(t)$ are defined. Thus, calculate curvature $101_7$ determines the value of $G_i''(t)$.

After calculate curvature $101_7$, characterize curvature $101_8$ determines the sign of the curvature and the magnitude of the curvature. The magnitude of the curvature is processed by scale curvature $101_9$.

Scale curvature $101_9$ scales the curvature magnitude so that the magnitude of the output signal for each filter is the same for the same average curvature. Recall that the curvature filter time window for each filter is a power of two times the minimum bunch size. The scale factor is $2^{(6-p)*2}$ where $p=\ln(\text{working bunch size}/t_i)$ and $t_i$ is the minimum bunch size.

In subsequent steps, described more completely below, the scaled curvature is used with the sign of the curvature to identify extrema of the second time derivative. After calculation of a scaled magnitude by scale curvature $101_9$, extremum found $101_{10}$ checks the status of the extremum found flag. If an extremum has been found, control passes to save curvature $101_{30}$. Otherwise, a curvature threshold flag is checked by threshold check $101_{11}$ to determine whether the curvature has moved above the threshold for a selected time period.

If the curvature threshold flag is zero, the sign of the curvature for the previous data bunch is compared with the sign of the curvature for the current data bunch by curvature sign check $101_{12}$. If curvature sign check $101_{12}$ detects a difference in the sign of the curvature between adjacent data bunches, a sign counter is initialized by initialize sign counter $101_{13}$ and processing transfers to save curvature $101_{30}$ which stores the magnitude and the sign of the curvature for the current filter.

If curvature sign check $101_{12}$ does not detect a change in the sign of the curvature between adjacent data bunches, the sign counter is incremented by increment sign counter $101_{14}$. After increment sign counter $101_{14}$, threshold calculation $101_{15}$ compares the magnitude of the curvature with the threshold. The magnitude of the curvature for the previous data bunch is also compared with the threshold. If both the current and the previous curvatures are greater than the threshold, and the value of the sign counter is greater than two, processing transfers to initialize extremum variables $101_{16}$, other wise processing transfers to save curvature $101_{30}$.

In initialize extremum variables $101_{16}$, several counters and other variables are initialized because the raw data has risen above the threshold level for a specified period of time and so the process of determining the location of the extremum must be initialized. Specifically, an extrema counter and a threshold counter are set to zero. The curvature threshold flag is set to indicate that the curvature has exceeded the threshold for a specified time period. The initial position in the zero crossing array and in the extrema bunch array are set to the index for the current data bunch. The zero crossing array is used to store the indices of the data bunches when the curvature passes through zero. Similarly, the extrema bunch array is used to store the indices of data bunches corresponding to the extrema of the curvature. The initial position in the extrema curvature array is set to the magnitude of the curvature because at this point, the magnitude of the curvature best characterized an extremum of the second derivative. The initial position in the minimax array and the sign array are both set to the sign of the curvature. As used herein, current data bunch means the data bunch located at the center of a filter when a selected condition is satisfied.

The extrema counter, which was set to zero by initialized extremum variables $101_{16}$, is used to identify the storage position in the extrema arrays for the extrema of the second time derivative found by locate extrema 101. The first extremum is located at the zero position in the extrema arrays, the second extremum at the first position and so forth. After an extremum is found and data characterizing the extremum are stored in the extrema arrays at the location corresponding to the current value of the extrema counter, the extrema counter is incremented so that the next extremum which is found is stored in the appropriate location.

The threshold counter, which is also set to zero by initialize extremum variables $101_{16}$, is used, as described more completely below, to determine when the raw data remains at or below the threshold level for a selected period of time. The minmax array is used in identification of the extrema by classify extrema. Briefly, as shown in FIGS. 6A–6D, the minimum and maximum of the second time derivative oscillate between a negative and a positive value. For each extremum after the first, the value stored in the minmax array is the value in the minmax array for the previous extremum multiplied by $-1$. After initialized extremum variables $101_{16}$, processing transfers to save curvature $101_{30}$ which stores the magnitude and the sign of the curvature for the filter being processed.

As previously described, if the curvature is not greater than the threshold for a selected period of time, processing transfer directly from threshold calculation $101_{15}$ to save curvature $101_{30}$ without initialization of the extrema variables.

If the curvature was greater than the threshold for at least two time intervals so that initialize extremum variables $101_{16}$ has set the threshold flag, processing passes from threshold check $101_{11}$ to new extremum check $101_{17}$ rather than to curvature sign check $101_{12}$. New extremum check $101_{17}$ calculates the difference in the curvature from calculate curvature $101_7$ and the curvature stored in the extrema arrays at the current value of the extrema counter. This difference is multiplied by the value stored in the minmax array at the current value of the extrema counter. If the resulting product is greater than the scaled threshold and if the stored curvature was generated by the same filter as the current filter or an adjacent filter, processing transfers to update extremum variables $101_{18}$, otherwise processing transfers to first extremum check $101_{19}$.

Update extremum variables $101_{18}$ stores the current curvature from calculate curvature $101_7$ in the extrema array at the position indicated by the value of the extrema counter. Similarly, the index of the data bunch and the sign of the curvature are stored in the extrema bunch array and the sign array respectively. If the value stored in the minmax array at the location having the same index as the current value of the extrema counter is not equal to the sign of the curvature, the data bunch index is stored in the zero crossing array.

Hence, new extremum check $101_{17}$ determines (i) whether the current value of the curvature has exceeded the previously stored value of the curvature by a significant amount, i.e., the current value of the curvature is a better estimate of a second derivative extrema than the stored curvature and (ii) whether the current curvature was generated by a filter with a specified relationship to the filter that generated the stored curvature. If both these conditions are true, the current value of the curvature represents a better estimate of a second derivative extrema and hence the stored extrema estimate is updated by update extremum variables $101_{18}$.

First extremum check $101_{19}$ ascertains whether the value of the extrema counter is greater than zero, indicating the one or more extrema have been located. If the first extremum is being processed, i.e., the extrema counter has the value zero, processing passes to post extremum check $101_{27}$, otherwise processing passes to filter check $101_{20}$. Filter check $101_{20}$ determines whether the current filter is the same filter that detected the last stored extremum. If the current filter is not the same filter which detected the last stored extremum, processing passes to post extremum check $101_{27}$. However, if the filters are the same, processing transfers from filter check $101_{20}$ to curvature check $101_{21}$. If the magnitude of the curvature is less than the threshold, curvature check $101_{21}$ transfers to increment threshold counter $101_{22}$ which in turn increments the threshold counter. Conversely, processing transfers to initialize threshold counter $101_{23}$, wherein the threshold counter is initialized to zero.

Threshold counter check $101_{24}$ determines whether the curvature for eight consecutive data bunches has remained below the threshold. If the value of the threshold counter is greater than eight, a baseline has been detected. As previously described, the baseline is considered an extremum, and so an extremum has been found. Thus, update extrema arrays-baseline found $101_{25}$ stores the characteristics of the extremum corresponding to the baseline. Specifically, the extrema counter is increased, the sign of the curvature is set to zero and then an extremum found flag is set by extremum found $101_{26}$ and processing transfers to post extremum check $101_{27}$. If the threshold counter has a value less than 8, processing transfers from threshold counter check $101_{24}$ to post extremum check $101_{27}$.

Post extremum check $101_{27}$ determines whether (i) the calculated curvature is less than the stored curvature; (ii) the current filter is the same as the one which detected the stored curvature; and (iii) an extremum has been detected. If an extremum has not been detected, and conditions (i) and (ii) are true, an extremum has been found, i.e., an extremum is found when the signal from the filter which generated the currently stored extremum value changes direction significantly. Hence, the extrema arrays are updated by update extrema arrays $101_{28}$ and the extremum found flag is set by extremum found $101_{29}$.

If the three conditions are not satisfied, post extremum check $101_{27}$ passes to save curvature $101_{30}$. Save curvature $101_{30}$ stores the curvature and the sign of the curvature so that these values are available for the next filter. Finally, the filter window is increased by a factor of 2 by increase filter window $101_{31}$. If the new time window is less than the maximum, increase filter window $101_{31}$ transfers to modulus check $101_3$. If the maximum time window has been exceeded, processing transfers to the main program from increase filter window $101_{31}$.

When processing transfers from locate extrema 101 (FIG. 7) back to the main program and an extremum has been found, the main program passes control to classify extrema 102. Locate extrema 101 has generated an extrema file consisting of the arrays of extrema data. The extrema file contains information for each extremum which has been detected and not yet identified as belonging to a peak. For each extremum in the file the curvature, the sign of the curvature, the flag to indicate whether the extremum should be a positive or negative extremum, and the index of the data bunch for the extremum are stored.

Figure 13:
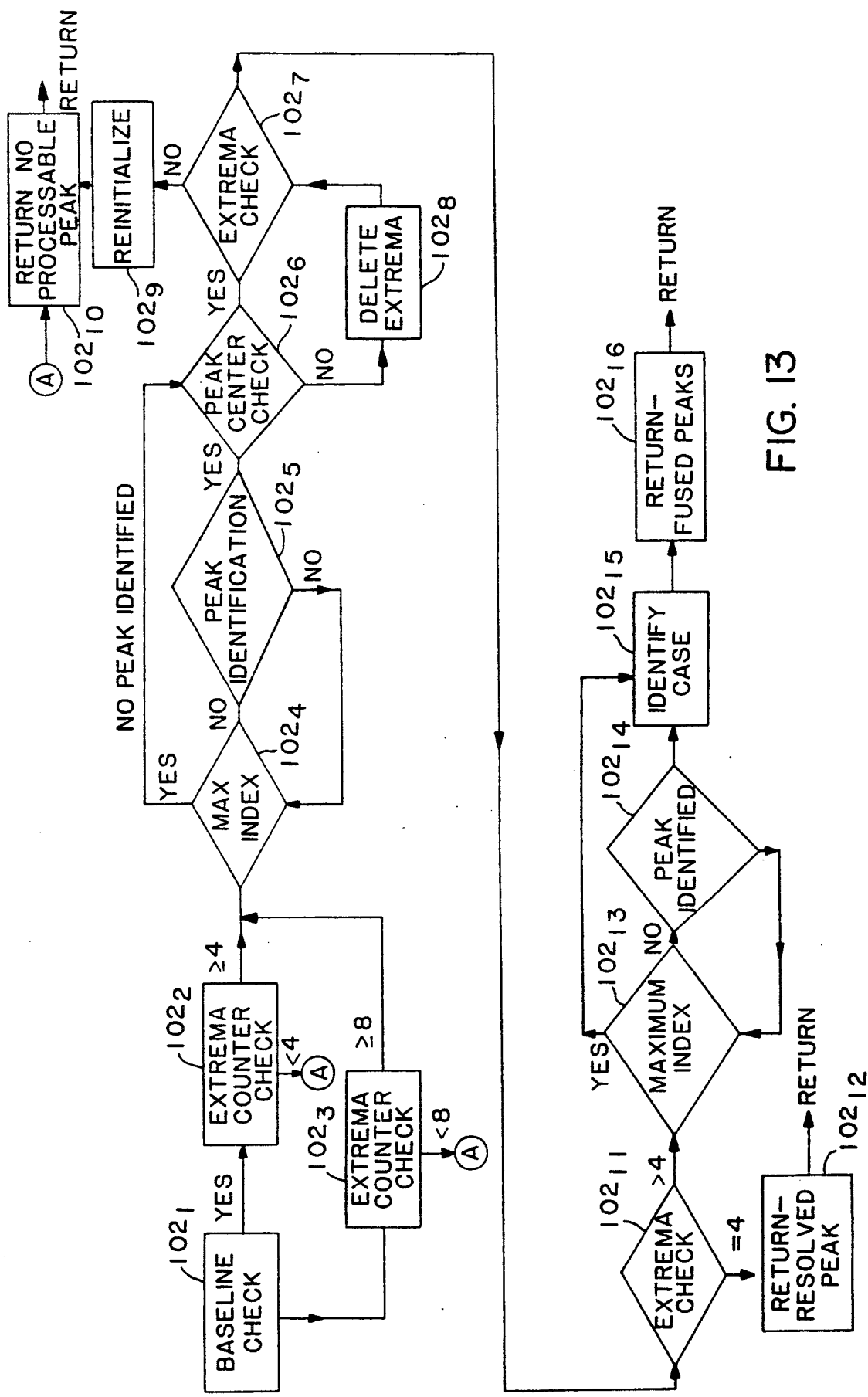
FIG. 13 is a block diagram of determine case 102 according to the principles of this invention.

Baseline check $102_1$ (FIG. 13) in classify extrema 102 establishes whether locate extrema 101 found a baseline. If a baseline has been detected, a first extrema counter check $102_2$ ascertains whether the value of the extrema counter is greater than or equal to four. If less than four extrema have been detected, sufficient data are not available to identify a peak, as previously explained. Thus, when less the four extrema have been detected, processing transfers to return to no processable peak $102_{10}$ and subsequently back to the main program and the next data point is supplied to locate extrema 101.

If a baseline has not been found, baseline check $102_1$ transfers to a second extrema counter check $102_3$ which in turn ascertains whether the value of the extrema counter is greater than or equal to either. If eight or more extrema are contained in the extrema file, at least one peak is contained in the data. Therefore, if the value of the extrema counter is greater than or equal to eight, extrema counter check $102_3$ transfers control to maximum index check $102_4$, otherwise control transfers to return no processable peak $102_{10}$.

After sufficient extrema are located to identify at least one peak, classify extrema 102 must identify the pattern of the second curvature extrema and determine which of the second derivative traces in the minimum set have been detected by locate extrema 101 and stored in the extrema file. Pattern recognition means 95 (FIG. 5A) for the extrema of the second derivative is incorporated in classify extrema 102. The empirical rules of pattern recognition means 95 are based upon empirical observations of the relationships between the second derivative extrema for a specific fused peak combination as well as between second derivative extrema for different fused peak combinations.

Specifically, the first peak in the extrema file should be centered at the second location in the extrema file so that processing stars on the second extremum. Thus, maximum index $102_4$ initializes an index counter to the second location in the extrema file. Peak identification $102_5$ uses a series of tests for each value of the index counter to determine where the center of the peak is located. These pattern recognition tests are based upon the characteristics of the traces shown in FIGS. 6A-6D. For each extremum, the minmax variable and the sign of the curvature should be the same so that their product should be a number greater than zero. Thus, the first test in peak identification $102_5$ multiplies the minmax variable and the sign of the extremum and determines whether the product is greater than zero.

If the product of the minmax variable and the sign of the curvature is greater than zero for the second extremum, the peak is properly centered and processing transfers to peak center check $102_6$. If the product of the minmax and the sign of the curvature for the second extremum is less than zero, the extrema in the extrema array are sequentially processed to determine which extremum represents the minimum/maximum. Specifically, after checking the second location in the extrema array, maximum index $102_4$ increments the index counter and checks whether the index counter is less than the value of the extrema counter minus two. Assuming the check is satisfied, control again passes to peak identification $102_5$.

For each extremum after the second, the product of the minmax variable and the sign of the curvature is also checked to determine whether the product is positive. If the product is negative, control passes back to maximum index $102_4$ which increments the index counter. However, if the product is positive, an additional test must be satisfied.

For acceptance of the third extremum, either the magnitude of the curvature of the second extremum must be less than the magnitude of the third extremum multiplied by two and the magnitude of the third extremum must be greater than the magnitude of the four extremum multiplied by two. For acceptance of the four extremum, the fourth extremum must be greater than the third extremum or the fourth extremum must be greater than the fifth extremum. For the fifth extremum, the product of the sign of the fourth extremum and the minmax variable for the fourth extremum must be greater than zero. When one of these tests is satisfied, processing passes from peaked identification $102_5$ to peak center check $102_6$. Alternatively, if maximum index $102_4$ determines that the value of the index counter is greater than the value of extrema counter minus two, maximum index $102_4$ transfer processing to peak center check $102_6$.

Peak center check $102_6$ examines the value of the index counter. If the value of the index counter corresponds to the second extremum in the extrema array, processing passes to extrema check $102_7$. However, if the index counter has a value greater than the location of the second extremum, processing passes to delete extrema $102_8$ which in turn shifts the extrema array so that the extrema corresponding to the value of index counter is the second extremum in the array. This operation deletes all extrema in locations prior to the value of the index counter minus one because these extrema are noise and do not represent a chromatographic peak. The value of extrema counter is also updated to correspond to the number of extrema in the array after the noise is deleted.

First extrema check $102_7$ determines (i) whether the control passed directly from maximum index $102_4$ to peak center check $102_6$, i.e., no processable peak was found, and (ii) whether the value of the extrema counter is less than four. If either of these conditions is true, reinitialize $102_9$ reinitializes the extrema counter, the threshold flag and the array used to store the accurate positions of the extrema for the peak before going to return no processable peak $102_{10}$ which returns control to the main program.

However, if the extrema count is greater than four and a processable peak was detected, extrema check $102_7$ passes control to a second extrema check $102_{11}$ which in turn determines whether the value of the extrema counter is greater than four. If the value of the extrema counter is four, the data in the extrema array represents a resolved peak. Thus, extrema check $102_{11}$ transfers to return resolved peak $102_{12}$ which in turn returns control to the main program.

If the value of the extrema counter is greater than four, second maximum index $102_{13}$ sets the value of the index counter to the location of the third extremum in the extrema file. Peak identified $102_{14}$ uses the pattern recognition rules based upon the trances in FIGS. 6A–6D to analyze the extrema at the location corresponding to the value of the index counter. Processing transfer between maximum index $102_{13}$ and peak identified $102_{14}$ to identify the largest extrema that satisfies the pattern recognition tests of peak identified $102_{14}$.

Specifically, if the magnitude of the curvature of the second extremum is less than the magnitude of the third extremum multiplied by two and the magnitude of the third extremum is greater than the magnitude of the fourth extremum multiplied by two, the extrema are from highly fused peaks of different sign. If the fourth extremum is greater than the third extremum or the fourth extremum is greater than the fifth extremum, the extrema are from highly fused peaks of the same sign. If the product of the sign of the fourth extremum and the minmax array value for the fourth extremum are greater than zero, the extrema represent slightly fused peaks of different signs. If none of these criteria are satisfied, the extrema represent slightly fused peaks of the same sign.

In identify case $102_{15}$, the value of the index counter for the largest extremum, which satisfies one of the pattern recognition tests, is used to generate an integer identifying the fused peaks represented in the extrema file and return-fused peaks $102_{16}$ provides this integer value to the main program. While in this embodiment empirical relationships were determined in pattern recognition 92 (FIG. 5A) and incorporated in analyze data 93 as described above for classify extrema 102, in another embodiment, a neural net is trained, using a procedure similar to that described below, in pattern recognition 92 to determine the fused peak case and then the neural net would be used in classify extrema 102 instead of the empirical pattern recognition rules. Further study is required to implement the neural net analyses. In addition, other pattern classification or recognition means known to those skilled in the art could be adapted for use in pattern recognition means 95 of this invention. For examples of other pattern classification or recognition means, see for example Massart et al., *Chemometrics: a textbook*, Elsevier, Amsterdam (1988).

The identification of the characteristics of the chromatographic data using the extrema of the second time derivative provides an unique capability for analysis of peak data in general. The steps of: (i) data characterization 90 (FIG. 5A) and attribute definition 91; (ii) development of pattern recognition means 95 for the selected attribute; (iii) analysis of raw data using multiple digital filters to locate and identify the second time derivative extrema; and (iv) using the pattern recognition means to classify the extrema can be used in general to characterize raw data so that the individual peaks in the data can be subsequently parameterized.

Moreover, this method of characterizing raw data for further detailed analyses which generates a set of characteristic parameters for each peak represents a significant advancement over the prior art because to assumptions have been made about the baseline. Rather, the raw data is analyzed and identified as being one of a number of possible combinations. Therefore, the results of the analysis are not biased by the prior subtraction of a baseline from the data. This method provides the user with precise information about the relationship between peaks in the raw data so that the user can analyze the peaks in any manner desired without introducing a bias in the data. Prior art methods such as those of Foley and Dorsey, described above, required not only a prior baseline correction, but also assumptions about the relationships of the fused peaks.

After the extrema have been classified by classify extrema 102, processing transfers to measure extrema 103 (FIG. 7). In one embodiment measure extrema 103 precisely determines the location of the zero crossings and the location of the maximum/minimum of the peak. As used herein, the phase "maximum/minumum" means the maximum for a positive peak and the minimum for a negative peak. The precise location of these parameters is necessary, as explained below, to obtain good peak parameter estimates when a neural net is used in calculate parameters 105. Also, if a lookup table is used with a parameter such as signature ratio CRATIO, the accuracy of the value of CRATIO depends upon the accuracy with which the zero crossings and the minimum/maximum are determined. However, measure extrema 103 consumes a significant amount of computation time and therefore offsets the processing speed advantage of neural nets. In another embodiment, measure extrema 102 is not utilized and processing transfers directly from determine case 102 to select data 104.

The integer value provided by determine case 102 is used to identify the maximum/minimum index location in the extrema array. This value is used to identify the index for the raw bunch data which is processed by measure extreme 103. Using the raw data, values of the curvature are calculated using Eq. 8. To find the zero crossings of the curvature, the data bunches that bracket the zero crossing, i.e., one data bunch having a positive value of the curvature and an adjacent second data bunch having a negative value of the curvature are found. After location of data bunches that bracket the zero crossing, three point polynomial interpolation is used to precisely estimate the location, i.e., the time, of the zero crossings. Similarly, a three point polynomial interpolation is used to precisely locate the time and magnitude of the min/max of the curvature. Polynomial interpolation is well known to those skilled in the art. The functions "compute_extrema," "measure_extrema," "slope," and "fit" in attached Microfiche Appendix A, incorporated herein by reference, illustrate one embodiment of measure extrema 103.

An important aspect of measure extrema 103 is the data bunch size used in the calculation. In this embodiment, the size of the data bunches is adjusted so that there are ten data bunches between the zero crossings, i.e., the inflection points of the peak. Empirical experience has demonstrated that about 10 to 20 data bunches across the entire peak are optimal. If fewer data bunches are used, the accuracy of the processing is diminished. If more data bunches are used, the effect of noise is amplified.

The general framework for processing the data described above, which includes (i) multiple digital filters to determine the extrema of the second derivative, (ii) classification of the peak type by analysis of second derivative extrema, and (iii) measurement of the precise location of the second derivative extrema provides information that may be processed in a number of ways so as to generate a set of characterizing peak parameters for each peak detected.

Unlike prior art methods, this sequence of data processing is not dependent upon subtraction of a baseline from the raw data prior to processing. Thus, in contrast to the prior art methods, a wandering or indeterminate baseline does not limit the application of this general framework. Moreover, this processing provides a set of peak parameters that contain characterizing information. Specifically, in one embodiment, the peak height, the time of the peak height, the peak width, as measured by the distance between zero crossings of the second time derivative, and peak skewness, as measured by the signature ratio CRATIO are known.

In one embodiment, as described with respect to FIGS. 8A-8D above, fused peaks are resolved into one or more resolved peaks by select data 104 and each of the resolved peaks is processed in turn by calculate parameters 105. In another embodiment, select data 104 removes any prior peak, for example, peak 114 in FIG. 8D, and then using the data from classify extrema 102 and measure extrema 103 defines a set of raw data corresponding to fused peaks, for example peaks 115 and 116 in FIG. 8D, for processing by calculate parameters 105. The precise processing used by select data 104 is dependent upon the method used in calculate parameters 105 to generate a set of parameters for each peak.

Figure 14:
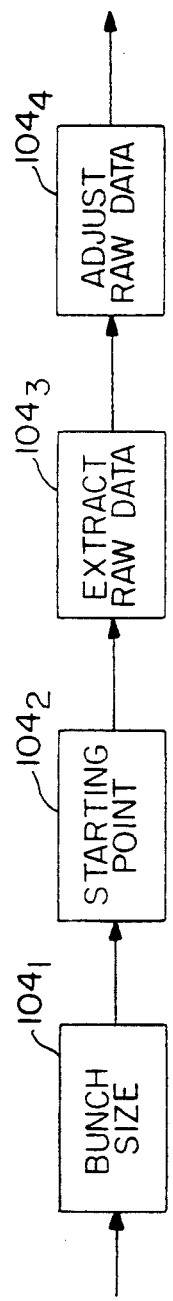
FIG. 14 is a block diagram of select data 104 of this invention.

However, the general structure of select data 104 is independent of the process used in calculate parameters 105 and only the specific implementation of the general structure varies from application to application. As shown in FIG. 14, select data 104 is a multistep process. The process includes the steps of: (i) selection of a data bunch size; (ii) determination of an initial data bunch; (iii) extract data size to correct bunching around the peak maximum/minimum; and (iv) adjusting raw data.

Bunch size $104_1$ (FIG. 14) determines the optimal bunch size for use in calculate parameters 105. As previously described, an optimal number of data bunches between the zero crossings of the second derivative ranges from about six to about twelve. Therefore, in one embodiment bunch size $104_1$ subtracts the first zero crossing of the curvature from the second zero crossing of the curvature and divides the difference by twelve to select the data bunch size.

After the data bunch size is determined, a range of data must be selected so that the time range of the data selected extends generally from the $t_g-5*\sigma$ to $t_g+5*\sigma$ where $\sigma$ is the standard deviation associated with the peaks and $t_9$ is the time of the maximum displacement, i.e., the peak crest, of the gaussian peak. Using this criteria, starting point $104_2$ multiplies the data bunch size from bunch size $104_1$ by a constant, 16 in one embodiment, and subtracts the product from the location of the peak center to define the starting point, i.e., the initial data bunch for the peak analysis.

With the initial data bunch specified, a total number of data bunches are extracted from the raw data by extract raw data $104_3$ so that the total range of data is within about the $\pm 5\sigma$ range. The specific implementation of extract raw data $104_3$ is dependent upon calculate parameters 105. If calculate parameters 105 processes a single peak at a time, extract raw data $104_3$ multiplies the constant used in starting point $104_2$ by two and adds four data bunches to the product. The resulting number represents the number of data bunches, each data bunch having the width defined by bunch size $104_1$, selected by extract raw data $104_3$. For a constant of 16 in starting point $104_2$, thirty-six data bunches are selected from the raw data by extract raw data $104_3$.

If calculate parameters 105 processes a pair of fused peaks, a wider range of data is selected by extract raw data $104_3$. In this embodiment, the constant from starting point $104_2$ is multiplied by four and two is added to the product by extract data $104_3$. Hence, if the constant is again 16, extract raw data $104_3$ selects 66 data bunches each with the width defined in bunch size $104_1$ starting with the bunch defined by starting point $104_2$.

Figure 15:
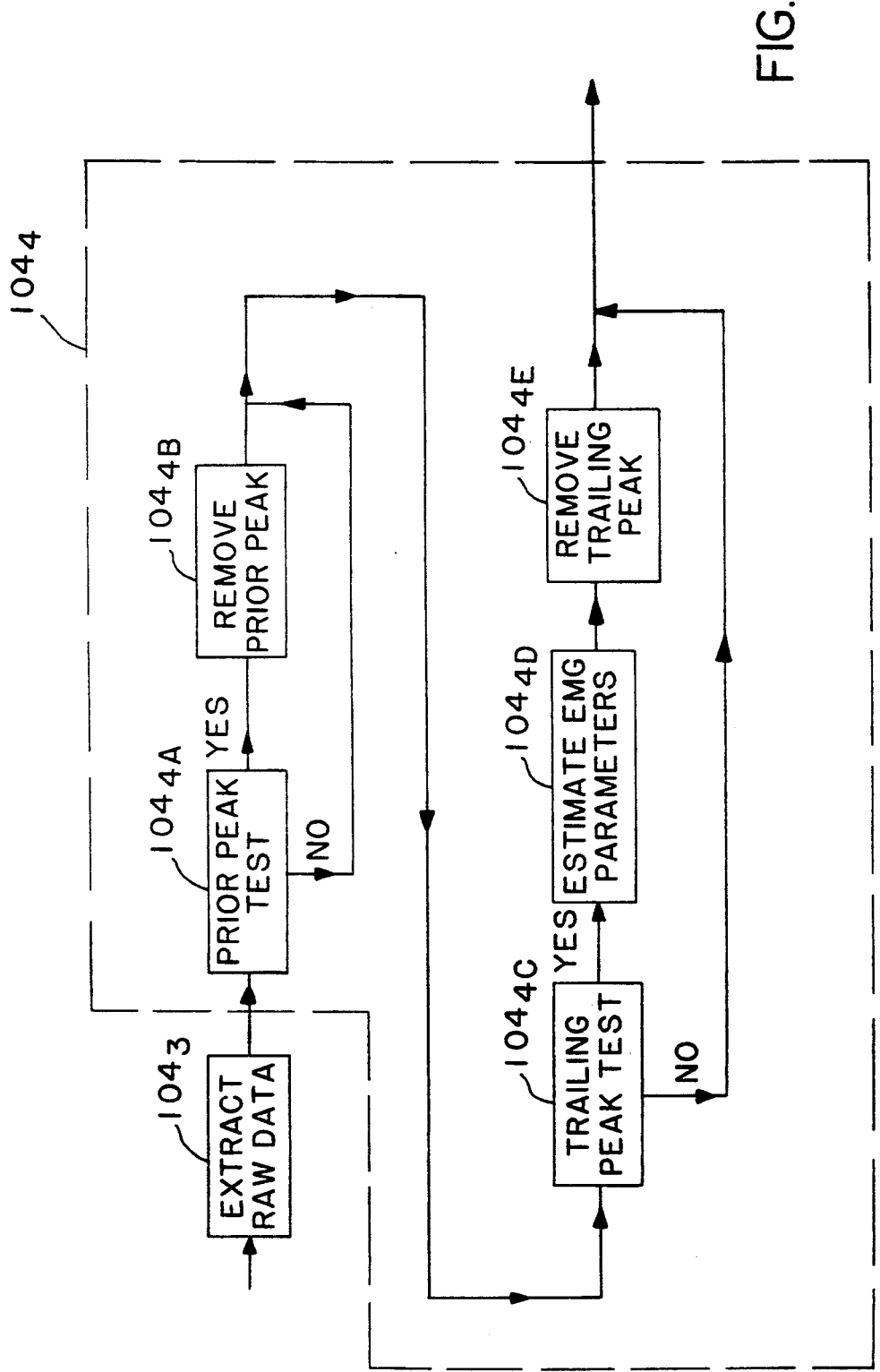
FIG. 15 illustrates one embodiment of adjust raw data $104_4$ of this invention.

The processing used in adjust raw data $104_4$ to remove contributions from adjacent peaks is also directly dependent upon the method use din calculate parameters 105. If calculate parameters 105 characterizes only resolved peaks, adjust raw data $104_4$ (FIG. 14) includes the steps of (1) testing for a prior peak $104_{4A}$ (FIG. 15); (2) removing prior peak $104_{4B}$; (3) testing for a trailing peak $104_{4C}$; (4) estimating trailing peak EMG parameters $104_{4D}$; and (5) removing trailing peak $104_{4E}$.

After each resolved peak is processed by calculate parameters 105 (FIG. 7) in this embodiment, if classify extrema 102 indicated that fused peaks are being processed, prior peak 108 (FIG. 7) sets a prior peak flag. Hence, adjust raw data prior peak test $104_{4A}$ (FIG. 15) checks the prior peak flag to determine whether the peak is preceded by a prior peak. If not prior Peak exists, processing transfers to the trailing peak test $104_{4C}$. If a prior peak exists, the selected raw data is processed by remove prior peak $104_{4B}$. The EMG parameters for the prior peak have been determined. Accordingly, using the EMG parameters and each of the selected data points a trace for the prior peak is calculated and subtracted from the raw data.

Specifically, using the EMG parameters for the prior peak, the EMG function G(t) (see equation 4) is evaluated at each time interval over the time range of the raw data. EMG function G(t) includes an integral that must be evaluated for each time point. However, in a preferred embodiment, a series expansion given in M. Abramowitz and I. A. Stegun, Editors, *Handbook of Mathematical Functions*, Applied Mathematical Series No. 55, National Bureau of Standards, Washington D.C., p. 932, (1964) is used to Equation 4 to evaluate the integral. The series expansion for the integral is:

$$\frac{1}{\sqrt{2\pi}} \int_{-\infty}^{z} e^{-\frac{y^2}{2}} dy = \quad (9)$$

$$1 - \frac{1}{\sqrt{2\pi}} e^{-\frac{z^2}{2}} (b_1 t + b_2 t^2 + b_3 t^3 + b_4 t^4 + b_5 t^5) + \epsilon(X)$$

$$t = \frac{1}{1 + pz} \qquad |\epsilon(X)| < 7.5 \times 10^{-8}$$

$p = 0.2316419 \qquad z > 0$ $b_1 = 0.319381530 \qquad b_4 = -1.821255978$ $b_2 = -0.356563782 \qquad b_5 = 1.330274429$ $b_3 = 1.781477937$ for $z < 0$ $$\frac{1}{\sqrt{2\pi}} \int_{-\infty}^{z} e^{-\frac{y^2}{2}} dy =$$

$$\frac{1}{\sqrt{2\pi}} e^{-\frac{z^2}{2}} (b_1 t + b_2 t^2 + b_3 t^3 + b_4 t^4 + b_5 t^5) + \epsilon(X)$$

After the contribution of the prior peak is removed from the selected raw data, processing passes to trailing peak test $104_{4C}$. Trailing peak test $104_{4C}$ tests the integer returned by classify extrema 102 to ascertian whether a trailing peak is present. If a trailing peak does not exist, the raw data is ready for further processing. However, if a trailing exists, estimate EMG parameters $104_{4D}$ calculates the EMG parameters for the trailing peak.

First, estimate EMG parameters $104_{4D}$ calculates signature ratio CRATIO, as previously described. Recall that signature ratio CRATIO is one of the peak parameters in the set of peak parameters containing characterizing information that was generated by the previous operations/ Table 1 lists the number of the row, i. in Column 1; signature ratio CRATIO in Column 2; and the skewnes, expressed as $\tau/\sigma$, in Column 3. Column 3 through Column 5 are EMG peak definition parameters. As described below, interpolated peaks definition parameters, a second set of parameters, are used in combination with the set of peak parameters containing characterizing information, a first set of parameters, to generate a set of characterizing parameters, a third set of parameters, for each peak. Lookup Table 1 includes a range of values for the signature ratio CRATIO and a set of peak definition parameters, $\tau/\sigma_i$, $sigma_i$, $height_i$, $rtime_i$, for each value of signature ratio $cratio_i$.

TABLE 1

| i | $cratio_i$ | $\tau/\sigma$ | $sigma_i$ | $height_i$ | $rtime_i$ |
|---|---|---|---|---|---|
| 1 | 0.499975 | 0.100000 | 0.491707 | −0.149150 | −0.043384 |
| 2 | 0.495770 | 0.300000 | 0.478256 | −0.166981 | −0.218163 |
| 3 | 0.488131 | 0.500000 | 0.462633 | −0.190488 | −0.345843 |
| 4 | 0.480089 | 0.700000 | 0.448277 | −0.218996 | −0.441499 |
| 5 | 0.470309 | 0.900000 | 0.436728 | −0.250592 | −0.509524 |
| 6 | 0.463733 | 1.100000 | 0.428109 | −0.285412 | −0.565854 |
| 7 | 0.462249 | 1.300000 | 0.420133 | −0.320610 | −0.623333 |
| 8 | 0.456172 | 1.500000 | 0.413130 | −0.355721 | −0.660210 |
| 9 | 0.448825 | 1.700000 | 0.408687 | −0.393306 | −0.683244 |
| 10 | 0.443877 | 1.900000 | 0.404198 | −0.431676 | −0.708442 |
| 11 | 0.435612 | 2.100000 | 0.400068 | −0.472040 | −0.719531 |
| 12 | 0.432274 | 2.300000 | 0.396573 | −0.511801 | −0.739838 |
| 13 | 0.428108 | 2.500000 | 0.393350 | −0.552216 | −0.754311 |
| 14 | 0.425740 | 2.700000 | 0.391009 | −0.596144 | −0.770370 |
| 15 | 0.421326 | 2.900000 | 0.389283 | −0.637783 | −0.776923 |
| 16 | 0.416583 | 3.100000 | 0.386530 | −0.681665 | −0.785714 |
| 17 | 0.416856 | 3.300000 | 0.385099 | −0.724638 | −0.800000 |
| 18 | 0.417341 | 3.500000 | 0.385416 | −0.768505 | −0.812329 |
| 19 | 0.416615 | 3.700000 | 0.383183 | −0.812269 | −0.824657 |

As defined previously, skewness is the ratio of peak half widths at a selected peak height. In this embodiment, the peak half widths were measured at the half-height of the Gaussian peak. Table 1 was generated using 19 different EMG curves. The range of parameters for the EMG curves were selected so that the data in Table 1 bound the EMG curves usually encountered in HPLC.

For a calculated signature ratio, CRATIO, the value of $\tau/\sigma$ is determined by first finding the values $cratio_{i-1}$, $ratio_i$ in Column 2 of Table 1 which bound calculated signature ratio CRATIO. If calculated signature ratio, CRATIO is greater than or equal to 0.5, CRATIO is set to 0.4999 and if CRATIO is less than or equal to 0.41658, CRATIO is set to 0.41658. A fraction, fr, is defined as:

$$fr = \frac{CRATIO - cratio_i}{cratio_{i-1} - cratio_i} \quad (10)$$

where $cratio_i$ and $cratio_{i-1}$ are the values in Table 1 that bracket CRATIO. If fraction, fr, is greater than one, the fraction is set to one.

The estimated skewness parameter, ns, is:

$$ns = (fr) \times (\tau/\sigma_{i-1}) + (1-fr)(\tau/\sigma_i) \quad (11)$$

After estimated skewness, ns, for the trailing peak is determined, the time difference in zero crossings for the trailing peak is converted to an estimated peak width parameter, nw, using the values, $sigma_i$ in the third column of Table 1 and fraction fr, calculated above:

$$nw = ((fr)^*(sigma_{i-1}) + (1-fr)^*(sigma_i))^*(zcross_2 - zcross_1] \quad (12)$$

where
nw = estimated Gaussian standard deviation
$zcross_1$ = time o first zero crossing of second derivative
$zcross_2$ = time of second zero crossing of second derivative Using estimated peak width parameter, nw, estimated peak amplitude parameter, nh, is calculated using the values $height_i$, in Column 4 of Table 1, fraction, fr, and the curvature, mmcurvl, from measure parameters 103 according to:

$$nh = ((fr^*height_{i-1}) + (1-fr)^*height_i)^*nw^*nmcurv1 \quad (13)$$

this expression for the estimated peak amplitude parameter converts the peak width parameters generated in the processing of the data to an EMG amplitude parameter.

The estimated time of the peak amplitude nrt is calculated using values $rtime_i$ in Column 5 of Table 1, the estimated peak width, nw, and time, maxt, of the center of the trailing peak.

$$nrt = (fr^*rtime_{i-1} + (1-fr)^* rtime_i) * mw + maxt \quad (14)$$

Thus, using interpolated peak definition parameters obtained from lookup Table 1 and the set of parameters containing characterizing information for the peak, the EMG parameters for the trailing peak have been completely defined. Using the estimated parameters, nw, ns, nh, nrt, the EMG trace is calculated using the series expansion (Eq. 9) described above in Eq. 4 and subtracted from the raw data.

Adjust raw data $104_4$, in this embodiment, has processed the extracted raw data so that only the data for a single resolved peak remains. This data is analyzed by calculate parameters 105 to determine the EMG parameters that characterize the selected data.

If calculate parameters 105 processes fused peaks, then adjust raw data $104_4$ is similar to the embodiment described above except the trailing peak is not removed from the raw data. Hence, in this embodiment, adjust raw data $104_4$ F(GI. 14) subtracts any contribution from a prior peak and then provides calculate parameters 105 with data corresponding to a pair of fused peaks.

As previously described, calculate parameters 105 (FIG. 7) analyzes the raw data from select data 104 nd generates a set of parameters which characterize each peak in the raw data. Alternatively, calculate parameters 105 can be used to characterize peaks provided by any process that identifies data for a peak. Calculate parameters 105 uses one of (i) a lookup table; (ii) a neural net; (iii) curve fitting; and (iv) combinations of lookup tables. neural nets or curve fits to generate a set of characterizing parameters for each peak. The precise method used in calculate parameters 105 depends upon the accuracy and the computational time desired.

Lookup tables and neural nets are both computationally fast, but the achievable accuracy depends on the accuracy of the input parameters and the detail built into either the lookup table or the neural network. Simplex fits are somewhat slower than lookup tables or neural nets, but such fits provide a high degree of accuracy. As indicated above, calculate parameters 105 may also include a combination of these approaches to achieve a balance between speed and accuracy.

The process described above in which the signature ratio CRATIO was used to estimate the parameters for a trailing peak in select data 104 can be implemented directly in calculate parameters 105. The use of CRATIO and Table 1 is an example of using a lookup table in calculate parameters 105. In fact, the general approach of using a lookup table may be expanded to include generalized functions rather than EMG functions as in Table 1.

The more generalized lookup table in calculate parameters 105 would be, in one embodiment, based upon a convolution integral of an EMG function and an instrument function. The instrument function is determined by passing an eluent directly through the detector directly from the injector and measuring the resulting detector response. Unlike the measurement to determine a threshold level. i.e., a blank chromatographic run, the generation of the instrument function does not include the characteristics of the chromatographic column, but rather only information about the detection and injection systems and the associated electronics. The measured instrument function and an EMG function, as represented by Equation 4 above, would be convolved using a convolution integral to generate a general chromatographic function.

As described with respect to Table 1, a range of general chromatographic functions would be generated, i.e., a number of EMG functions would be convolved with the instrument function. Parameters that characterized each of the generalized chromatographic functions would be implemented in the lookup table. Using a variable GRATIO, equivalent to the CRATIO defined above for only EMG functions, the parameters used to characterize a measured peak would be selected based upon the value of variable GRATIO and interpolation within the lookup table. The use of the generalized lookup table would be totally equivalent to that discussed above with respect to CRATIO. Alternatively, the lookup table for the generalized chromatographic function would provide an initial estimate of parameters for a Simplex analysis, similar to that described below.

The use of a lookup table based upon the signature ratio provides means for characterizing a peak based upon data with the best signal-to-noise ratio, as described previously, because the data used to generate the signature ratio is about the peak crest. In this embodiment, the characterizing parameter set obtained with the lookup table is used to generate a trace for the peak using equation 4. The trace is subtracted from the raw data to generate the baseline estimate.

In one embodiment, calculate parameters 105 uses a neural net to process a series of evenly spaced points in time from select data 104 that generally cover the range of $t_g - 5^*\sigma$ to $t_g + 5^*\tau$. As described below, the neural net has been trained to generate EMG parameters, $\sigma$, $\tau$, $t_g$ and the peak amplitude which best represent an EMG peak. As used herein, the EMG parameters, $\sigma$, $\tau$, $t_g$, h are the characterizing set of parameters. The peak area and other peak characteristics of interest are generated using this set of EMG parameters.

Figure 16:
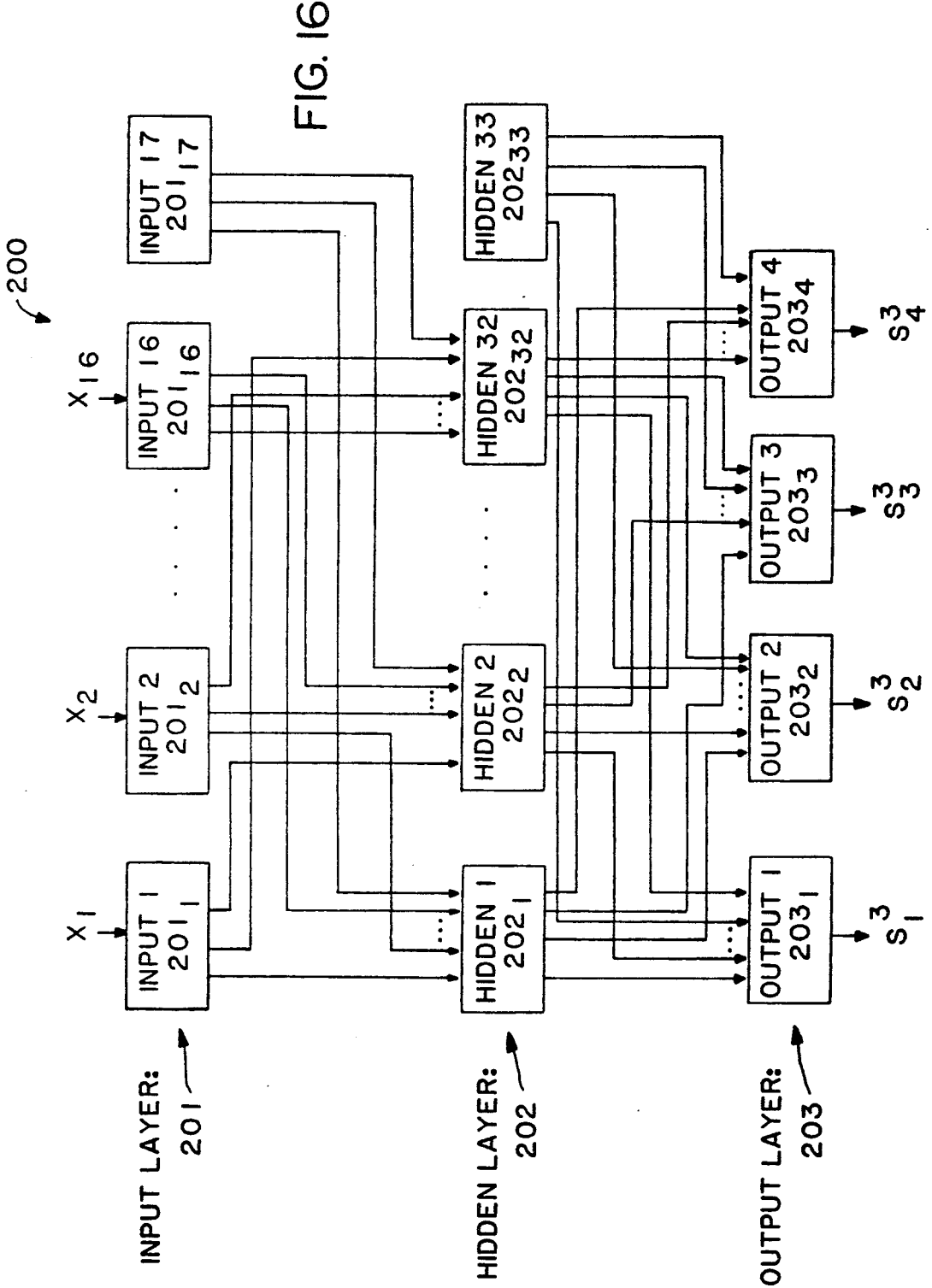
FIG. 16 illustrates a neural net as implemented in this invention.

The neural network used in this invention is an interconnected set of units. Neural network 200 is organized in layers of units as shown in FIG. 16. Neural net 200 has three layers. The first layer consisting of units $201_1$–$201_{17}$ is input layer 201. Input signals $X_1$–$X_{16}$ are applied to units $201_1$–$201_{16}$ respectively. The input signals $X_1$–$X_{16}$ are the curvature for sixteen evenly spaced data bunches which are calculated using Equation 8. Sixteen data bunches plus four additional data bunches are selected from the data bunches identified by select data 104 for calculation of the sixteen curvature values.

Input layer 201 is followed by one or more "hidden" layers, units $202_1$–$202_{33}$ (FIG. 16), and terminated by an output layer 203, units $203_1$–$203_4$. Neural net 200 is illustrative of only one embodiment of this invention and is not intended to limit the scope of the invention. According to the principles of this invention, a neural net with more hidden layers or a neural net with more or fewer units in each layer can be used.

The output signals of each unit in a given layer n of the network are supplied to each unit in the next layer n+1 and no others. However, in every layer except the output layer, there is one unit $201_{17}$, $202_{33}$ with a fixed output signal of one and no input signals. Input signals $X_1$–$X_{16}$ to net 200 are applied to input units $201_1$–$201_{16}$, one value per unit. The output signal of each input unit is just the input signal. All units in the neural net 200, except input units $201_1$–$201_{16}$ and fixed units $201_{17}$, $202_{33}$, transform the set of input signals from the previous layer of the network into a single output signal using a sigmoidal or logistic function.

Specifically, the output signal S of unit j in the nth layer of the network is:

$$S_j^n = \frac{1}{1 + e^{-x}} \quad n = 2, N \quad (15)$$

$$x = \sum_{i=1}^{k} {}^j w_i S_i^{n-1}$$

where
$S_j^n$ is the output signal of the jth unit in the nth layer of the neural network
k is the number of units in the n-1 layer of the neural network
${}^j w_i$ is the weight in the jth unit of the nth layer for output signal $S_i^{n-1}$ from the ith unit in the n-1 layer
N is the number of layers in the network.

Thus, each input signal $S_i^{n-1}$ from layer n-1 of the network is assigned a unique weight function ${}^j w_i$. The information content of neural net 200 is carried in the values of weights ${}^j w_i$.

When input signals $X_1$–$X_6$ (FIG. 16) are applied to neural net 200, signals propagate through the net a layer at a time until signals reach output layer 203. The amplitude range of output signals from a output layer 203 is between zero and one, but typically this is a more limited domain than is desirable. Therefore, each output unit signal $S_j^N$ is scaled so that the resulting output signal $V_j$ falls within the range of $-0.9*$ MV and $0.9*$ MV where MV is the maximum value of the peak parameter. Constant MV was selected based upon empirical experience with neural nets and the analysis of chromatographic data. Scaling of data over a selected range is a method known to one skilled in the art of data analysis.

Specifically $$V_j = (S_n^N - 0.5) * MV_j * \quad (16)$$

where
$V_j$ is the output signal for the jth unit in layer N of the neural net
$MW_j$ is selected so that $-0.9$ MV $\leq V_j \leq 0.9$ MV for parameter j.

Prior to using neural net 200 to process sixteen evenly spaced second time derivative values, net 200 was first trained, i.e., the weights in neural net 200 were defined.

Briefly, the strategy used was to randomly select $\sigma$, $\tau$, and $t_g$ parameters for an EMG curve. Using the selected values of $\sigma$, $\tau$, and $t_g$, as described below, sixteen values of the second derivative of the EMG function were calculated at evenly spaced time intervals which had been selected to bracket the maximum/minimum of the EMG function. The 16 calculated values were supplied to the input units of the neural network and the neural network processed the input values to produce an estimate of the EMG parameters used to generate the input data.

The estimated EMG parameters were compared with the actual EMG parameters and the neural network weights adjusted to minimize the error between the parameters generated by the network and the parameters used to calculate the second derivatives. Historically, this process is referred to as learning by back-propogating errors. See for example, D. Rumelhart, G. Hinton, and R. Williams, "Learning representations by back-propogating errors," Nature 323, pp. 533–536 (1986). The back propagation was repeated approximately one million times until the output signals of neural net 200 matched the desired output signals to within the desired accuracy for a specified large number of test cases.

Specifically, in one embodiment, the following procedure was used to train neural net 200 to generate EMG parameters from sixteen evenly spaced time values of the second time derivative of an EG function. Values for $\sigma$, $\tau$, and $t_g$ were randomly selected. The values for each parameter were selected from a domain having the range of that EMG variable. The algorithm used to generate the random values for the EMG parameters also prescaled $\sigma$ and $\tau$ so that the time between inflection points on either side of the EMG peak was between 6 and 12, and prescaled $t_g$ to range within $\pm 1$. Specifically, $$h = 25{,}000 \quad (17)$$

$$\sigma = 2 + \frac{RAND}{32{,}768}$$

$$\frac{\tau}{\sigma} = (3.7)\left(\frac{RAND}{32{,}768}\right) + 0.1$$

$$t_g = 10 + \left(\frac{RAND}{32{,}768}\right)$$

where RAND is a random number between 0 and 32,768. This scaling generates a set of parameters within the range required to generate an EMG peak.

After the random values of the EMG parameters have been generated, the EMG function, G(t) in Equation (4) was evaluated using the generated parameters and integer time values. For the above scaling, the time values were 0, 1, 2, ..., 29. Again G(t) (Equation 4) was evaluated using the series expansion described above. The digital filter for the curvature, G"(t), which is proportional to the second time derivative of the EMG function, was evaluated at time points 2, 3, ..., 27.

After curvature G"(t) was calculated for each time t, a value of $t_m$ was found so that $G''(t_m)$ is $\leq G''(t)$ for all t in the range $(t_g-5*\sigma) \leq t \leq (t_g+5*\sigma)$. $G''(t_m)$ was the curvature corresponding to the maximum/minimum of the EMG function. After the time $t_m$ was defined, the value of the second derivative $G''(t_m)$ was used to normalize the 16 values of G" consisting of $G''(t_m-6)$, $G''(tm-5)$, ..., $G''(t_m+9)$. Specifically $$G''(t) = \frac{0.4 \times G''(t)}{G''(t_m)}, t = t_m - 6, t_m - 5, \ldots, t_m + 9 \quad (18)$$

The input signals to neural net 200 are $$X_i = G''(t) + 0.5, \quad i = 0 \quad t = t_m - 6 \quad (19)$$
$$i = 1 \quad t = t_m - 5$$
$$\cdot \quad \cdot$$
$$\cdot \quad \cdot$$
$$i = 15 \quad t = t_m + 9$$

The above sequence of steps are used to generate the input signals to the neural net in general. Therefore, when input signals to a neural net are described, the signals are equivalent to the expressions in Equations 18 and 19.

Prior to providing the first set of inputs signals to neural net 200, all the weights in the net must be initialized to a different value, since if two units of the same layer have identical weights on corresponding input signals, the units will continue to have the same output signals and weights throughout the training process. The initial weights were relatively small since the networks ability to learn is restricted if the unit output signal is too close to either zero or one. The initial weights were randomly chosen to be within the range of −0.1 to 0.1.

In the previous description, output signal $S_j^N$ was scaled to generate signal $V_j$. In the training process, the unscaled output unit signals $S_j^N$ are computed. The target output values $EMG_j$, i.e., the randomly selected EMG parameters, are scaled to the unscaled output unit signal domain by the transformation:

$$S_j^{EMG} = \left(\frac{EMG}{2 \cdot EMG^{MAX}}\right) + 0.5 \quad (20)$$

$j = 1, 2, 3, 4$ where

-continued $EMG_1 = \frac{h}{G''(t_m)} \quad EMG_1^{MAX} = 8.0$ $EMG_2 = \sigma - 2 \quad EMG_2^{MAX} = 4.0$ $EMG_3 = \tau/\sigma \quad EMG_3^{MAX} = 4.0$ $EMG_4 = t_g - t_m \quad EMG_4^{MAX} = 4.0$ Accordingly, using the above expression, each target value $EMG_j$ is converted to an output unit signal $S_m^{EMG}$ which corresponds to the unscaled output signal $S_j^N$ from that output unit.

For each output unit, an adjustment factor is defined as $$\Delta_j = (S_j^{EMG} - S_j^N) \cdot S_j^n \cdot (i - S_j^N) \quad (21)$$

$j = 1, 2, 3, 4$

Adjustment factor $\Delta_j$ represents the difference of the unit output target value $S_j^{EMG}$ minus neural net 200 unit output value $S_j^N$ times the first derivative of the logistic function.

Adjustment factor $\Delta_j$ is used to adjust the weights $j^N w_i$ for the signals $S_i^{N-1}$ input to output unit j. The adjustment is accomplished by computing a correction term $CT_j^m$ to be added to the weight $_1^N w_n^m$ corresponding to the signal $S_i^{N-1}$. Correction term $CT_j^m$ is:

$$CT_j^m = \text{LEARN} \cdot \Delta_j \cdot S_i^{N-1} + \text{MOMEMTUM} \cdot CT_j m-1 \quad (22)$$

and the new weight for the next iteration m+1 is $$j^N w_i^{m+1} = j^N w_i^m + Ct_i^m \quad (23)$$

where
m = iteration in training net for the set of EMG parameters
i = 1, 2, 3, ..., 33
N = 3 and
j = 1, 2, 3, 4

MOMENTUM is a constant which in one embodiment was 0.9. MOMENTUM tends to keep changing the weight in the same direction as in the prior iteration of the training. LEARN is also a constant, 0.25 in one embodiment, which determines the extent to which the error in the current iteration influences the new weight. LEARN is roughly equivalent to the step size in a steepest descent optimization algorithm.

After the weights in the output unit shave been adjusted, the weights in the hidden layer units are corrected. This correction is done in several steps. First, it is necessary to calculate another adjustment factor $\delta_j$. In general, adjustment factor $\delta_j$ is defined as:

$$\delta_j^{m+1} = \left(\sum_{k=1}^{s} k^n (w_j^{m+1} \Delta_k) \cdot (S_j^{n-1}(1 - S_j^{n-1})\right) \quad (24)$$

where
s is the number of units in row n
k is the index indicating the unit in row n
m+1 is the index indicating the iteration
j is the index indicating the unit in row n-1
$\Delta_k$ is the correction term for k units in row n
$\delta_j$ is the correction term for unit j in row n-1

$k^n w_j^{m+1}$ is the weight in unit kin row n for the signal from the unit j in row n-1 on the m+1 interaction of training with a specified set of EMG in put signals Adjustment factor $\delta_j$ is used in Equation 25 to calculate the correction terms $CT_j$ for the weights in each of the unit sin a hidden layer and then the new weight is calculated using Equation 26.

$$CT_j^m = LEARN \cdot \delta_j \cdot S_n^{n-1} + MOMENTUM \cdot CT_j^{m-1} \quad (25)$$

$$j^n w_i^{m+1} = j^n w_i^m + CT_i^m \quad (26)$$

Approximately one million EMG cases with randomly chosen values of $\tau$, $\tau$, and $t_g$ were used to train neural net 200. After this training, neural net 200 provided EMG parameter estimates that were good to about within 1to 2l when presented with EMG curves having parameters within the range of parameters used in the training. The weights for the neural net are given in Microfiche Appendix A, which is incorporated herein by reference. The particular structure of the neural net in this embodiment is not essential to the invention. Greater or fewer units can be used in the input and hidden layers and more hidden layers can be included.

An important aspect of the neural net is to prescale the amplitude of the input data so that the input units of the neural net receive values ranging from 0.1 to 0.9. Also, the width of the input data is scaled so that the inflection points of the EMG curve fall within the time frame of the neural net input units because this scaling assures that the net processes data with the best signal-to-noise ratio.

With the neural net 200 trained as described above, net 200 in calculate parameters 105 can be used to estimate a set of parameters, which characterize an EMG resolved peak. Neural net 200 is effectively an interconnected array of level sensitive switches, i.e., each unit in the net is a level sensitive switch that generates a selected level output signal which is a weighted function of the input signals to the switch. The selected output level is determined by the training of the net. As described above, select data unit 104 (FIGS. 7, 14) has defined twenty data bunches in the time range $t_m - 8t_i$ to $t_m + 11t_i$ where $t_m$ is the time of the maximum/minimum of the peak and $t_i$ is the width of each data bunch. The second time derivative for each data bunch, except the first two and the last two data bunches, is evaluated using Equation 8. Hence, sixteen second time derivatives are calculated at evenly spaced time intervals. The ith input signal $X_i$ to neural net 200 is:

$$X_i = \frac{0.4 \cdot G''(t)}{G''(t_m)} + 0.5 \quad i = 0, \quad t = t_m - 6t_i \quad (27)$$

$$i = 1, \quad t = t_m - 5t_i$$

$$\cdot \quad \cdot$$
$$\cdot \quad \cdot$$
$$\cdot \quad \cdot$$

$$i = 15, \quad t = t_m + 9t_i$$

This scaling of the second derivative assures that all input signals to the neural net are between 0.1 and 0.9.

After the scaling, the input values are applied to the neural net and the neural net generates the four output signals $V_0, V_1, V_2, V_3$.

The peak amplitude h is $$h = V_o \cdot G''(t_m) \quad (28)$$

The time $t_g$ is $$t_g = (t_m - 8t_i) + t_i \cdot (8 + V_3) \quad (29)$$
$$= t_m + V_3 \cdot t_i$$

where $V_3$ is the scaled output signal from output unit $203_3$.

The standard deviation, $\sigma$, is $$\sigma = (t_i) \cdot (V_1 + 2) \quad (30)$$

and the skewness, $\tau/\sigma$, is $$\frac{\tau}{\sigma} = V_2 \quad (31)$$

Finally, the peak area A is $$A = \sigma \cdot h \cdot \sqrt{2\pi} \quad (32)$$

In addition to the lookup tables and the neural nets as described above, calculated parameters 105 also uses in another embodiment a Simplex fitting procedure to generate a set of parameters for each of the peaks detected as described above. Simplex fitting procedures are well known in the prior art and so only the general procedure utilized is described herein. For a more detailed discussion of Simplex analyses see, for example, William H. Press et al., *Numerical Recipes in C, the Art of Scientific Computing*, Cambridge University Press, Cambridge, England (1988) and M. A. Sharaf et al., *Chemometrics*, John Wiley & Sons, New York, 1986.

The number of parameters, vertices, used in the Simplex analysis depends upon whether a single peak is analyzed or whether a pair of fused peaks is analyzed. For a single peak, a four vertex Simplex procedure is used while for a pair of fused peaks up to an eight vertex Simplex procedure may be used. In the embodiment in Microfiche Appendix A, a seven vertex Simplex fit was used. The same EMG parameter $\tau$ was used for both fused peaks in a fused peak sequence.

To describe the general Simplex procedure implemented in calculate parameters 105 a simple example is used. This example is not intended to limit the scope of the invention to the embodiment shown, but rather is intended to illustrate the general process. Since the general process utilizes a multidimensional space, the general process is not amenable to a two- or three-dimensional presentation.

Figure 18:
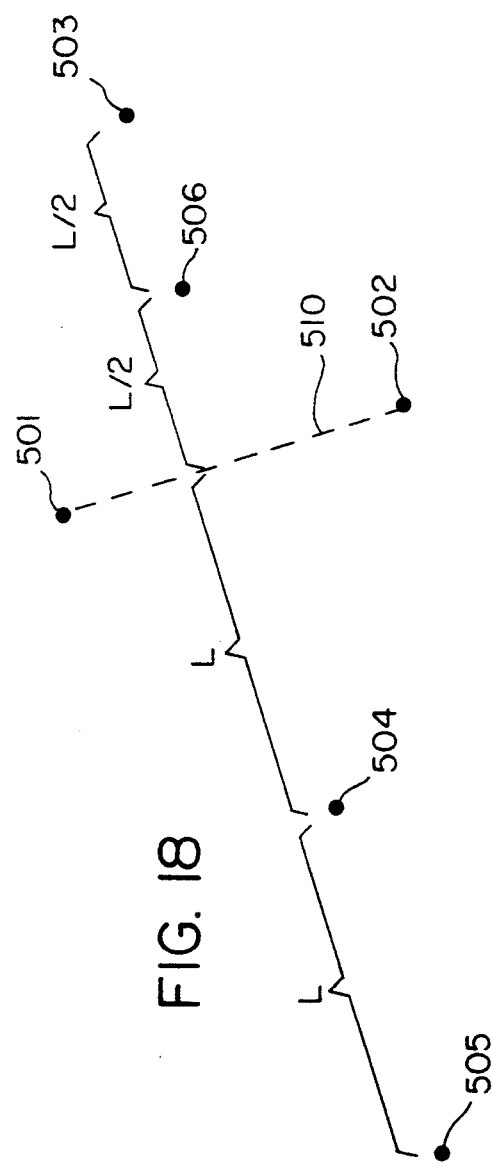
FIG. 18 is a graphical representation of the Simplex fit used in this invention.
Figure 17:
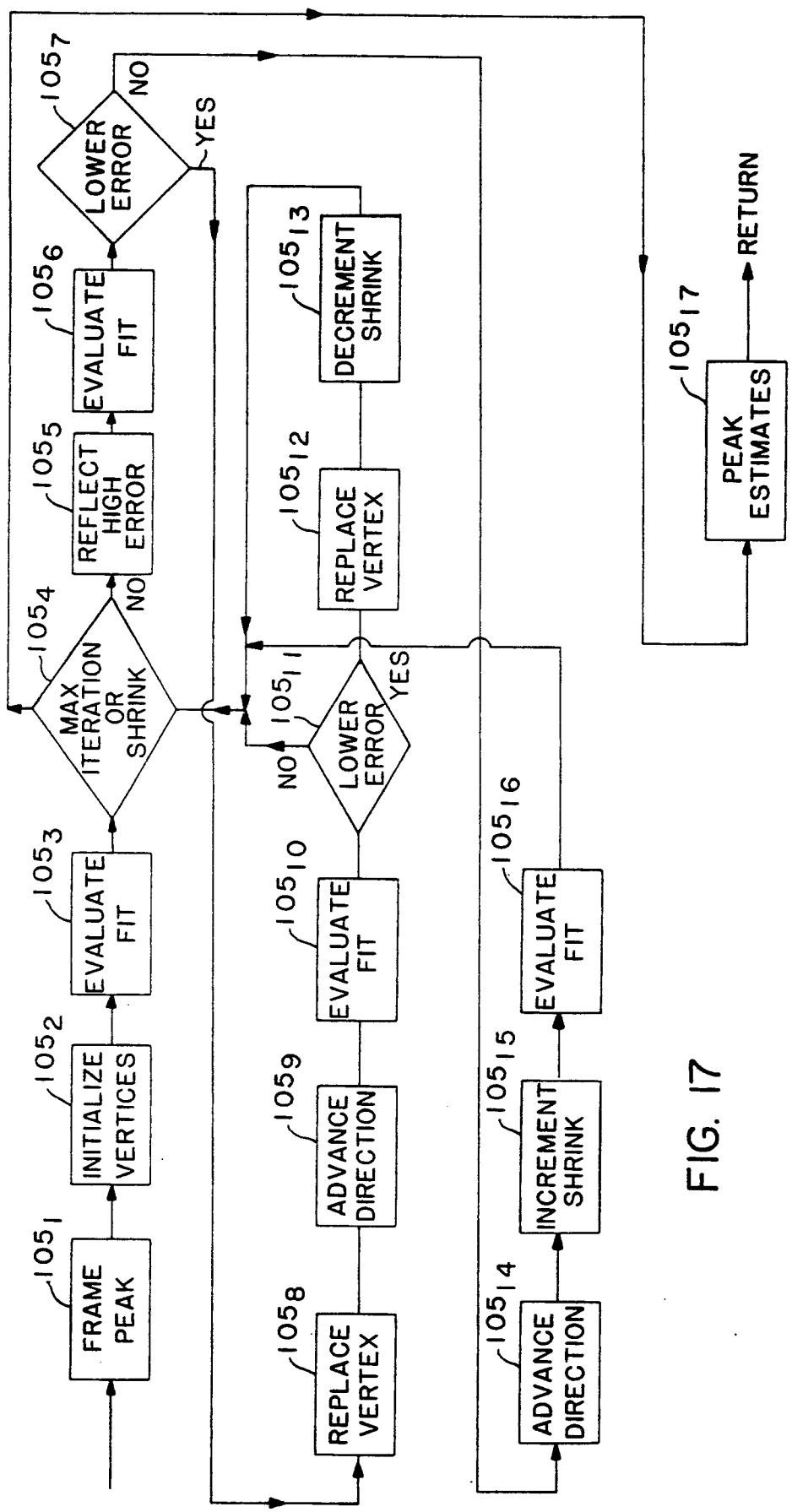
FIG. 17 is a flow diagram for the Simplex fit used in this invention.

A process flow diagram for the Simplex process is illustrated in FIG. 17. Initially frame peak $105_1$ defines the width of the peak in terms of the number of data points used in the Simplex process. After frame peak $105_1$, initialize vertices $105_2$ defines the initial estimates for the set of peak parameters used in the Simplex process. After the initialization of the set of parameters, a first evaluate fit $105_3$ estimates the peak shape with the EMG function defined in Equation 4 using the estimated parameters. The estimated peak shape is subtracted from the raw data provided by select data 104 to produce a difference value at each data point. A straight line is fit to the differences between the raw data and the estimated peak shape. The straight line is found using Eq. 7. A least squares analysis of the fit of the line to the difference data is used to generate an error estimate for each of the vertices. FIG. 18 illustrates three vertices 501, 502, and 503 which are estimates for the parameters of interest. In FIG. 18, vertex 503 has the highest error in evaluate fit $105_3$ (FIG. 17).

The next step in the analysis is to proceed iteratively to find the best fit to the data. Accordingly max iteration or shrink $105_4$ initializes the number of iterations at zero and the shrink at zero. Max iteration or shrink $105_4$ in one embodiment, continues the Simplex process until either the shrink reaches 12 or the number of iterations reaches 1,000. After initialization of the iteration and shrink parameters, reflect error $105_5$ first locates the vertex with the maximum error, e.g., point 503 in FIG. 18, and reflects high error vertex 503 through plane 510 defined by vertices 501, 502, Vertex 504 represents the reflected image of point 503.

A first evaluate fit $105_6$ (FIG. 17) uses new vertex, point 504, and recalculates the least square error for the straight line fit as described above. The new error estimate is checked against the original error estimate by lower error $105_7$ and if the new error estimate for vertex 504 is lower than the error estimate for original vertex 503, replace vertex $105_8$ stores vertex 504 and the associated error value.

Advance direction $105_9$ then takes another step in the same direction as from point 503 to 504. Specifically, vertex 504 is projected a distance equal to 2L from plane 510 to vertex 505, as shown in FIG. 18. After advance direction $105_9$ (FIG. 17), a third evaluate fit $105_{10}$ is performed to generate the error for vertex 505. If the error associated with vertex 505 is less than the error associated with vertex 504, a second lower error test $105_{11}$ passes control to second replace vertex $105_{12}$. After replace vertex $105_{12}$, decrement shrink $105_{13}$ decrements the shrink by one which indicates a plex expansion. Decrement shrink $105_{13}$ passes control to max iteration or shrink $105_4$.

If the error associated with vertex 505 is greater than the error associated with vertex 504, lower error $105_{11}$ passes control to max iteration or shrink $105_4$. Max iteration or shrink $105_4$ determines whether either the maximum number of iterations or the shrink has been met and if not begins a repeat of the process with reflect high error $105_5$.

If after evaluate fit $105_6$, the error associated with vertex 504 is greater than for the error for vertex 503, lower error $105_7$ transfers to a second advance direction $105_{14}$ which moves the high error vertex only half the distance to plane 510 formed through points 501, 502. The new vertex is vertex 506. The shrink count is incremented by increment shrink $105_{15}$ and then a third evaluate fit $105_{16}$ determines the least square error corresponding to vertex 506. After evaluate fit $105_{16}$, control returns to max iteration or shrink $105_4$.

This Simplex process usually continues until the maximum number of the shrink ,12 in one embodiment, is reached and at their time max iteration or shrink $105_4$ passes control to peak estimates $105_{17}$ which retrieves the best estimates of the four EMG parameters which characterize the chromatographic peak and performs a baseline adjustment to the raw data for the best straight line fit that has been found corresponding to the four EMG parameters. Therefore, unlike prior art methods which used a prior determination of the baseline and then performed all subsequent analyses, the baseline determination according to the principles of this invention is not made until the final step in the process which defines the set of parameters for each peak.

In the Simplex curve fitting, a family of curves is generated in determining the best fit to the data. For each curve fit, a value of the EMG characterizing set of parameters $\sigma$, $\tau$, $t_g$, h are estimated. If the skewness is changed, for example, to obtain a better curve fit, each of the other EMG parameters also changes. Moreover, the change in the EMG parameters is complex function, i.e., the characterizing EMG parameters are not either linearly related or related in a way that once the change in one of the EMG parameters is known, the change in the other EMG parameters is easily ascertained. This interaction of the EMG peak characterizing parameters makes the curve fitting complex and requires the generation of the family of curves described above.

However, as previously described, the first set of parameters generated by the process and apparatus of this invention, i.e., the amplitude of the peak crest, the time of the peak crest, a measure of the peak width, and a measure of the peak skewness contain characterizing information about the measured peak. Unfortunately, this first set of parameters is not the EMG characterizing set of parameters. Nevertheless, a reversible transformation can map the EMG characterizing set of parameters $\sigma$, $\tau$, $t_g$, h into a transformed set of parameters which include the observed retention time $R_T$ (i.e., the time of the peak crest), the square root of second moment of the measured peak $\sqrt{M_2}$, the observed amplitude of the peak crest, $h_{act}$ (this amplitude is the amplitude that would be measured on a chromatogram at the observed retention time) and the $\tau/\sigma$ ratio. Here, a reversible transformation means that either the EMG parameters can be mapped into the transformed parameters or the transformed parameters can be mapped into the EMG parameters. For a description of the second moment of the measured peak, see, for example, J. Foley and M. dorsey, "Equation for Calculation of Chromatographic Figures of Merit for Ideal and Skewed Peaks," *Anal. Chem.* 55, 730–737 (1983).

One advantage of such a transformation is that the observed retention time and the observed amplitude of the peak crest are known, i.e., are in the first set of parameters generated, and do not change. Moreover, the square root of the second moment of the measured peak does not change with changes in the $\tau/\sigma$ ratio. Thus, the transformation reduces the characterization process from determining the four unknown EMG parameters to essentially finding the $\tau/\sigma$ ratio that gives the best fit to the measured data. Further, the transformed variables are linear. The linear relationships further simply the curve fit process.

In one embodiment the transformation is:

$$\sigma = \frac{\sqrt{M_2}}{\sqrt{(\tau/\sigma)^2 + 1}} \tag{33}$$

$$h = h_{act} * (e^{\frac{(RT-t_g)^2}{2\sigma^2}})$$

$$t_g = R_T - (sgn(\tau/\sigma)) * \sigma *$$

$$(C_0 + (C_1 + (C_2 + (C_3 (C_4 + (C_5 + (C_6 + (C_7 +$$

$$C_8 * \tau/\sigma) * \tau/\sigma) * \tau/\sigma) * \tau/\sigma) * \tau/\sigma) * \tau/\sigma) * \tau/\sigma) * \tau/\sigma)$$

-continued where $sgn(\tau/\sigma) = -1$ when $\tau/\sigma < 0$
$\phantom{sgn(\tau/\sigma)} = +1$ when $\tau/\sigma > 0$ $C_0 = -0.00595515 \quad C_5 = -0.0421305$ $C_1 = 1.09834 \quad C_6 = 0.0136128$ $C_2 = -0.528622 \quad C_7 = -0.00207816$ $C_3 = 0.121979 \quad C_8 = 0.0001255$ $C_4 = 0.0422954$ To obtain the coefficient $C_0$ to $C_8$ for the polynomial fit, the first derivative with respect to time of an EMG function (see Equation 4) with a fixed h, $\sigma$ and $t_g$ and varying values of $\tau/\sigma$ were synthesized. Approximately 30-40 different $\tau/\sigma$ values were used. The zero crossing of each of the synthesized first time derivatives was precisely determined. Recall that the time of the first derivative zero crossing is the retention time $R_T$. After calculation of the retention time a table of $\tau/\sigma$ vs. $(R_T - t_g)/\sigma$ was prepared. The coefficients $C_0$ to $C_8$ were determined by doing a polynomial fit in $\tau/\sigma$ to this table.

It is anticipated that curve fits using the transformed variables will be significantly faster than curve fits using the EMG parameters. Further, it is anticipated that the accuracy of the transformed variable curve fitting process will be at least as good as the accuracy of the Simplex process used to estimate the EMG characterizing parameters.

The lookup table, the neural net or the Simplex fit may be used in any number of combinations to generate estimates of the set of parameters for each peak detected. For example, a neural net could be initially used to estimate the set of characterizing parameters for the raw data from selected data 104 and these characterizing parameters could be initial estimate provided to the Simplex fit. Alternatively, lookup table could be used to provide the initial estimates for the Simple fit.

In yet another embodiment, a combination of neural networks could be used to refine the estimates for the set of characterizing parameters. To demonstrate one application of a combination of the neural networks, lookup tables and Simplex fittings, data, as shown in FIG. 19, is used. This data has an initial resolved peak 301 (FIG. 19A) and then a set of four fused peaks 302, 303, 304, 305 wherein the first pair 302, 303 (FIG. 19B) are highly fused peaks of the same sign, the second pair 303, 304 (FIG. 19C) are slightly fused peaks of the same sign, and the third pair 304, 305 (FIG. 19D) are also slightly fused peaks of the same sign.

For resolved peak 301, locate extrema 101 (FIG. 7) detects each of the four extrema of the curvature and places data describing the extrema in the extrema file, as previously described. Classify data 102, upon determining that the extrema file includes four extrema with a baseline as one of the extrema, indicates that a resolved peak has been found. Measure extrema 103 precisely locates the peak crest and the inflection points for the resolved peak, as previously described. Select raw data 104 provides twenty data bunches for analysis by calculate parameters 105.

Figure 20:
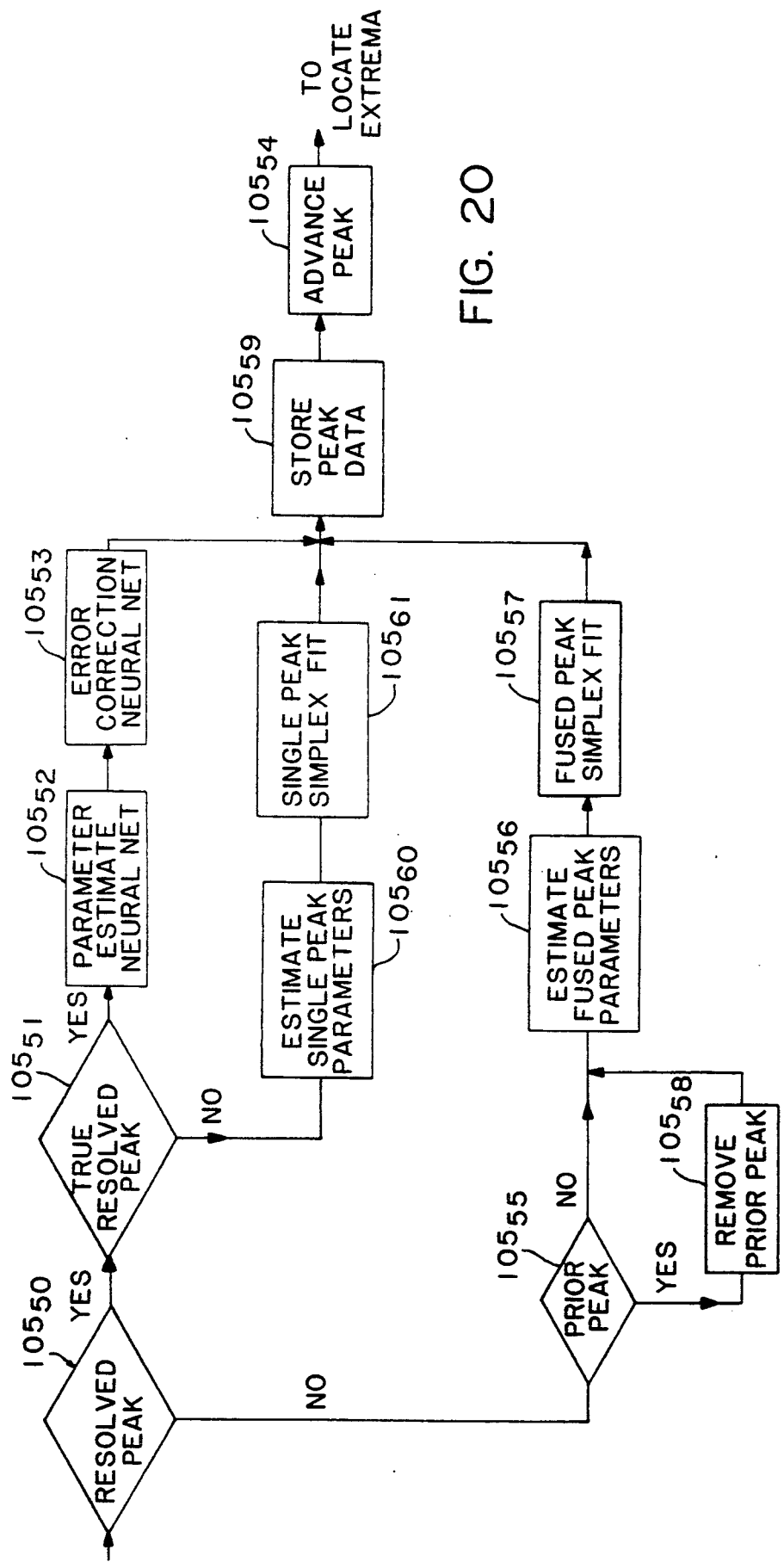
FIG. 20 is a flow diagram for one embodiment of calculate parameters 105 according to the principles of this invention.

Resolved peak $105_{50}$ (FIG. 20) in calculate parameters 105 first tests the integer output from classify extrema 102 to ascertain whether a resolved peak has been detected. Since peak 301 is a resolved peak, resolved peak $105_{50}$ passes control to true resolved peak $105_{51}$. True resolved peak $105_{51}$ determines that the peak is a true resolved peak, i.e., the peak is not the last peak in a sequence of fused peaks. Since peak 301 is a true resolved peak, processing is passed to a parameter estimate neural net $105_{52}$.

In this embodiment, parameter estimate neural net $105_{52}$ has been trained to generate a set of EMG characterizing parameters for a resolved peak when sixteen evenly spaced curvature values are applied to the net, as previously described. Thus, neural net $105_{52}$ generates a set of four EMG peak parameters for resolved peak 301 using the data from select data 104 as described above. After neural net $105_{52}$ completes processing, an error correction neural net $105_{53}$ which has sixteen input units, a hidden layer with thirty-three units, and an output layer of four units as in parameter estimate neural net $105_{52}$ is used.

Error correction neural net $105_{53}$ has been trained to generate error estimates for the set of characterizing parameters generated by parameter estimate neural net $105_{52}$. The weights in error correction neural net $105_{53}$ were defined using a process similar to that described above. However, for neural net $105_{53}$, a first set of EMG parameters were randomly selected and a second set of EMG parameters were also randomly generated. The traces generated by using Equation 4 and the two sets of EMG parameters were subtracted to produce an error file. The curvature of the error file was supplied as input data to neural net $105_{53}$ and in turn neural net $105_{53}$ generated corrections for the first set of randomly generated EMG parameters. The weight sin neural net $105_{53}$ were adjusted by back propagation of error, as previously described, using the known error file generated by subtraction of the two traces.

In this embodiment, the output signals $V_0$, $V_1$, $V_2$, $V_3$ from neural net $105_{52}$ are used to define EMG parameters h, $t_g\sigma$, and $\tau/\sigma$ as follows;

$$h = V_0 * G'(t_m) \quad (34)$$

$$\sigma = 2 + V_1$$

$$\frac{\tau}{\sigma} = V_2$$

$$t_g = 8 + V_3$$

These parameters are used in Equation 4 to generate an EMG function value for each of the twenty data bunches identified by select data 104. An error array of twenty values is defined by subtracting the raw data value for each bunch from the associated value of the EMG function value. Sixteen curvature values are generated from the error array using Equation 8. The sixteen curvature values are applied to error correction neural net $105_{53}$ which in turn generates four correction values $Y_0 Y_1$, $Y_2$, $Y_3$. The EMG estimated parameters are:

$$\begin{aligned}
h &= (V_0 - Y_0) * G'(t_m)/t_i^{min} \\
t_g &= (t_m - 8t_i) + t_i * (8 + V_3 - Y_3) \\
&= t_M + t_i * (V_3 - Y_3) \\
\sigma &= t_m * (V_1 - Y_1 + 2) \\
\frac{\tau}{\sigma} &= V_2 - Y_2
\end{aligned} \quad (35)$$

After the determination of the above set of parameters for resolved peak 301, the parameters describing resolved peak 301 are stored by store peak data $105_{59}$ for further analysis, as described below. Advance peak $105_{54}$ shifts the data for resolved peak 301 output of the extrema files and initializes the extrema counter so that it is ready to begin analysis for a second peak.

Locate extrema 101 (FIG. 7) continues to analyze the data bunches and when the eighth extremum is detected and stored in the extrema file, classify extrema 102 analyzes the extrema file. Classify extrema 102 ascertains that extrema in the extrema file represent highly fused peaks of the same sign. Based upon the integer from classify extrema 102, select data 104 prepares 66 data bunches for processing by calculate parameters 105. Calculate parameters 105 ascertains from the integer provided by classify extrema 102 that the peaks are fused and therefore resolved peak $105_{50}$ (FIG. 20) passes control to prior peak $105_{55}$. Since first peak 302 (FIG. 19B) of pair 302, 303 is being analyzed, the prior peak flag is not set so that prior peak $105_{55}$ (FIG. 20) transfers to estimate fused peak $105_{55}$ (FIG. 20) transfers to estimate fused peak parameters $105_{56}$. In estimate fused peak parameters $105_{56}$ signature ratio CRATIO, as defined above, for first peak 302 is used with Table 1 and Equations 10-14 to estimate the EMG parameters for the first peak. Subsequently, the same signature ratio CRATIO along with the parameters from measure extrema 103 for peak 303 are used to estimate the set of EMG parameters for peak 303 using Table 1 and Equations 10-14. Hence, estimate parameters $105_{56}$ generates two sets of EMG parameters.

Simplex fit $105_{57}$ performs a Simplex fit for the eight vertices and generates a best fit estimate of EMG parameters and a baseline estimate for peak 302. In another embodiment, a selected EMG parameter or selected EMG parameters for each peak in a pair of fused peaks could be taken as the same value. When the same parameter value is used for both of the peaks in the fused peak pair, the number of vertices in the Simplex fit is reduced by one for each of such parameter values.

The set of parameters from Simplex fit $105_{57}$ is added to the stored peak data file by store peak data $105_{59}$. Advance peak $105_{54}$ eliminates the four extrema for first peak 302 from the extrema file and resets the extrema counter appropriately. In addition, advance peak $105_{54}$ sets the prior peak flag.

Figure 19C:
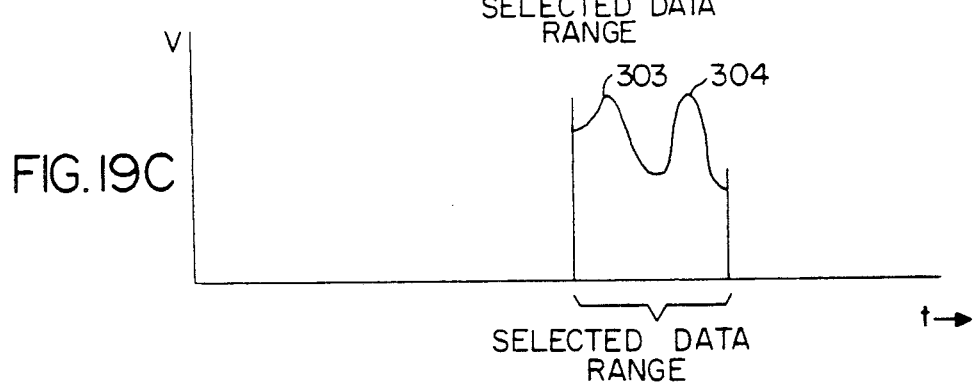
Figure 19D:
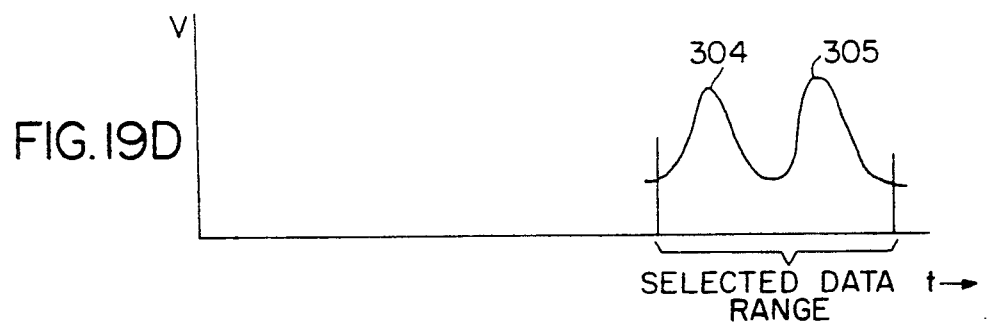

Locate extrema 101 (FIG. 7) continues to add additional extremum to the extrema file until eight extrema are in the file for peaks 303, 304 (FIG. 19C). Classify extrema 102 analyzes the extrema file and identifies the extrema as representing a pair of lightly fused peaks of the same sign. Select data 104 (FIG. 7) again identifies 66 data bunches for processing by calculate parameters 105 because classify extrema 102 classified the extrema as representing fused peaks. Resolved peak $105_{50}$ (FIG. 20) in calculate parameters 105 passes control to prior peak $105_{55}$. The prior peak flag was set by advance peak $105_{54}$. Prior peak $105_{55}$ passes control to remove prior peak $105_{58}$. The parameters for peak 302 were stored by store peak data $105_{59}$. The parameters for peak 302 are used with Equation 4 in remove prior peak $105_{58}$ to estimate the contribution of peak 302 to the data bunches provided by select data 104 for peaks 303, 304 (FIG. 19C). Remove prior peak $105_{58}$ subtracts the contribution of peak 302 from the raw data so that only data representing second and third peaks 303, 304 remains. Estimate parameters $105_{56}$ and Simplex fit $105_{57}$ generate a best fit set of parameters for second peak 303 in a manner similar to that described above. After store peak data $105_{59}$ saves the data describing peak 303, advance peak $105_{54}$ removes the extrema for the second peak 303 form the extrema files, initializes the extrema counter appropriately, and again resets the prior peak flag.

Locate extrema 101 (FIG. 7) then continues to find extrema until the baseline is detected. Determine case 102 analyzes the extrema files and identifies the third pair of peaks 304, 305 (FIG. 19D) as slightly fused peaks of the same sign. The process described above for the second pair of peaks 303, 304 is repeated for peaks 304, 305.

Figure 19E:
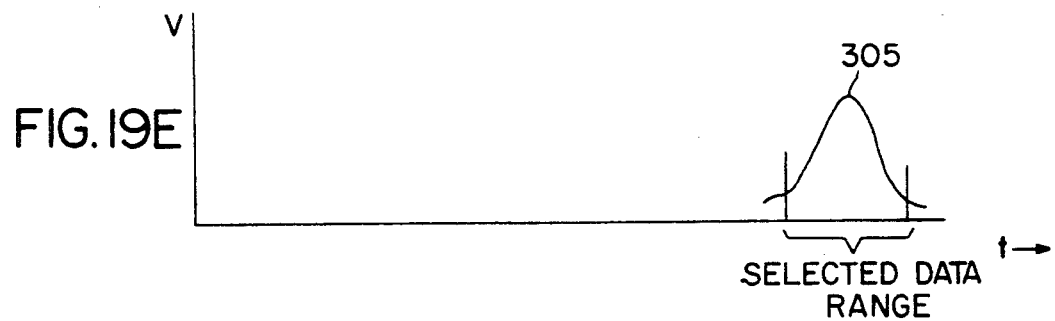

After peak 304 is characterized and control is passed to locate extrema 101, locate extrema 101 passes control to classify extrema 102 which identifies the extrema file data as a resolved peak. In calculate parameters 105, resolved peak $105_{50}$ (FIG. 20) transfers processing to true resolved peak $105_{51}$. However, the prior peak flag is set and true resolved peak $105_{51}$ transfers control to estimate single peak parameters $105_{60}$. Estimate single peak parameters $105_{60}$ uses signature ratio CRATIO and Equations 10-14 to estimate a set of parameters for peak 305 (FIG. 19E). Also, any contribution of peak 304 to peak 305 is removed using the known parameters for peak 304 in a manner similar to that previously described for remove prior peak $105_{58}$. Simplex fit $105_{61}$ performs a four vertex Simplex analysis and generates a best fit set of EMG parameters for peak 305.

After the set of parameters for the final peak is estimated, in one embodiment, the stored peak data is further analyzed to refine the peaks. In this embodiment, for each peak, the stored data describing the peaks is used in the EMG function (Eq. 4) to generate data that is subtracted from the raw data so as to remove contributions from adjacent peaks and hence generate data for a single peak. Then, using the stored set of parameters as initial estimates, a final four vertice Simplex fit is done on this data to provide a best estimate set of parameters for the peak and the baseline.

While the embodiment described herein provides accurate analyses in a reasonable computational time, other embodiments could use all neural nets, all lookup tables, all Simplex analyses, or other curve fitting analyses. The precise combination of methods used in calculate parameters would be determined by the accuracy and computational time limitations. The embodiments described herein are illustrative only and are not intended to limit the scope of this invention.

What is claimed is:

1. A neural net system for characterizing a peak superimposed on a baseline comprising:
    a source of data signals representing said peak superimposed on said baseline;
    an input layer comprising a plurality of input units operatively coupled to said source of data signals, each input unit generating an output signal in response to an input signal from respective ones of said data signals;
    at least one hidden layer comprising a plurality of hidden units operatively coupled to said input units, each hidden unit generating an output signal in response to a plurality of output signals from said input units which is a weighted function of said output signals from said input units; and
    an output layer comprising a plurality of output units operatively coupled to said plurality of hidden units, each output unit generating an output signal in response to a plurality of output signals from said hidden units wherein the output signals from an output unit represent best estimates of a set of parameters which characterize said peak, said set of parameters from said output unit being determined without prior baseline correction to said data signals.

2. The system of claim 1 further comprising:

means, operatively coupled to said source of data signals and to said input units, for differentiating each of said data signals; and means for providing said differentiated data signals as input signals to said input units.

3. The system of claim 2 wherein means for differentiating said data signals calculates the second derivative with respect to time of said data signals.

4. The system of claim 1 wherein each of said output unit output signals comprises a weighted function of said plurality of hidden unit output signals.

5. The system of claim 1 in which said output signals from said output units include at least one observable parameter comprising observed retention time.

6. The system of claim 1 in which said output signals from said output units algebraically transformed into exponentially modified gaussian parameters.

7. The system of claim 6 in which said exponentially modified gaussian parameters include at least $\delta$, the standard derivation of the gaussian function.

8. The system of claim 6 in which said exponentially modified gaussian parameters include at least $\tau$, the time constant of the exponential decay function.

9. The system of claim 6 in which said exponentially modified gaussian parameters include at least $t_g$, the time of maximum amplitude of Gaussian function.

10. The system of claim 6 in which said exponentially modified gaussian parameters include at least h, the peak vertical amplitude of the peak.

11. The system of claim 1 in which the amplitude of said data signals to said input layer are prescaled.

12. The system of claim 1 in which the width of said data signals to said input layer are prescaled.

13. The system of claim 1 in which said output signals from said output units include at least one observable parameter comprising observed peak height.

14. The system of claim 1 in which said output signals from said output units include at least one observable parameter comprising the square root of the second moment of the measured peak.

15. The system of claim 1 in which said output signals from said output units include at least one observable parameter comprising the ratio of the exponential decay constant to the gaussian peak width.

* * * * *